(12) United States Patent
Wang et al.

(10) Patent No.: US 11,468,983 B2
(45) Date of Patent: *Oct. 11, 2022

(54) TIME-DEPENDENT NAVIGATION OF TELEPRESENCE ROBOTS

(71) Applicant: InTouch Technologies, Inc., Santa Barbara, CA (US)

(72) Inventors: Yulun Wang, Goleta, CA (US); Charles S. Jordan, Santa Barbara, CA (US); Tim Wright, Santa Barbara, CA (US); Michael Chan, Santa Barbara, CA (US); Marco Pinter, Santa Barbara, CA (US); Kevin Hanrahan, Santa Barbara, CA (US); Daniel Sanchez, Summerland, CA (US); James Ballantyne, Santa Barbara, CA (US); Cody Herzog, Santa Barbara, CA (US); Blair Whitney, Santa Barbara, CA (US); Fuji Lai, Goleta, CA (US); Kelton Temby, Goleta, CA (US); Eben Christopher Rauhut, Watertown, MA (US); Justin H. Kearns, Los Angeles, CA (US); Cheuk Wah Wong, Bedford, MA (US); Timothy Sturtevant Farlow, Billerica, MA (US)

(73) Assignees: TELADOC HEALTH, INC., Purchase, NY (US); IROBOT CORPORATION, Bedford, MA (US)

(*) Notice: Subject to any disclaimer, the term of this patent is extended or adjusted under 35 U.S.C. 154(b) by 148 days.

This patent is subject to a terminal disclaimer.

(21) Appl. No.: 16/817,497

(22) Filed: Mar. 12, 2020

(65) Prior Publication Data
US 2020/0356101 A1  Nov. 12, 2020

Related U.S. Application Data

(63) Continuation of application No. 15/721,067, filed on Sep. 29, 2017, now Pat. No. 10,591,921, which is a (Continued)

(51) Int. Cl.
*G16H 40/67* (2018.01)
*G05D 1/02* (2020.01)
(Continued)

(52) U.S. Cl.
CPC ............ *G16H 40/67* (2018.01); *B25J 9/1689* (2013.01); *B25J 11/009* (2013.01); (Continued)

(58) Field of Classification Search
CPC .... G16H 40/67; G05D 1/0011; G05D 1/0088; G05D 1/0214; G05D 1/0217;
(Continued)

(56) References Cited

U.S. PATENT DOCUMENTS 3,821,995 A  7/1974 Aghnides
4,107,689 A  8/1978 Jellinek
(Continued)

FOREIGN PATENT DOCUMENTS

AU  1216200 A  5/2000
CA  2289697 A1  11/1998
(Continued)

OTHER PUBLICATIONS

Paulos et al., "Social Tele-Embodiment Understanding Presence", Autonomous Robots, vol. 11, Issue 1, Kluwei Academic Publishers, Jul. 2001, pp. 87-95.
(Continued)

*Primary Examiner* — Yuen Wong
(74) *Attorney, Agent, or Firm* — Kory D. Christensen

(57) ABSTRACT

A telepresence robot may include a drive system, a control system, an imaging system, and a mapping module. The
(Continued)

mapping module may access a map of an area and tags associated with the area. In various embodiments, each tag may include tag coordinates and tag information, which may include a tag annotation. A tag identification system may identify tags within a predetermined range of the current position and the control system may execute an action based on an identified tag whose tag information comprises a telepresence robot action modifier. The telepresence robot may rotate an upper portion independent from a lower portion. A remote terminal may allow an operator to control the telepresence robot using any combination of control methods, including by selecting a destination in a live video feed, by selecting a destination on a map, or by using a joystick or other peripheral device.

18 Claims, 43 Drawing Sheets

Related U.S. Application Data continuation of application No. 15/139,073, filed on Apr. 26, 2016, now Pat. No. 9,785,149, which is a continuation of application No. 13/958,413, filed on Aug. 2, 2013, now Pat. No. 9,323,250, which is a continuation-in-part of application No. 13/360,579, filed on Jan. 27, 2012, now Pat. No. 8,718,837.

(60) Provisional application No. 61/437,433, filed on Jan. 28, 2011.

(51) Int. Cl.
   B25J 9/16      (2006.01)
   B25J 11/00     (2006.01)
   G06T 11/00     (2006.01)
   G05D 1/00      (2006.01)

(52) U.S. Cl.
   CPC ......... G05D 1/0011 (2013.01); G05D 1/0088 (2013.01); G05D 1/028 (2013.01); G05D 1/0214 (2013.01); G05D 1/0217 (2013.01); G05D 1/0259 (2013.01); G05D 1/0261 (2013.01); G05D 1/0274 (2013.01); G06T 11/00 (2013.01); G05D 1/024 (2013.01); G05D 2201/0206 (2013.01)

(58) Field of Classification Search
   CPC .. G05D 1/0259; G05D 1/0261; G05D 1/0274; G05D 1/028; G05D 1/024; G05D 2201/0206; B25J 9/1689; B25J 11/009; G06T 11/00
   See application file for complete search history.

(56) References Cited

U.S. PATENT DOCUMENTS

| | | |
|---|---|---|
| 4,213,182 A | 7/1980 | Eichelberger et al. |
| 4,413,693 A | 11/1983 | Derby |
| 4,471,354 A | 9/1984 | Smith |
| 4,519,466 A | 5/1985 | Shiraishi |
| 4,553,309 A | 11/1985 | Hess et al. |
| 4,572,594 A | 2/1986 | Schwartz |
| 4,625,274 A | 11/1986 | Schroeder |
| 4,638,445 A | 1/1987 | Mattaboni |
| 4,652,204 A | 3/1987 | Arnett |
| 4,669,168 A | 6/1987 | Tamura et al. |
| 4,679,152 A | 7/1987 | Perdue |
| 4,697,278 A | 9/1987 | Fleischer |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | Georg et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Cran et al. |
| 5,006,988 A | 4/1991 | Borenstein et al. |
| 5,040,116 A | 8/1991 | Evans, Jr. et al. |
| 5,051,906 A | 9/1991 | Evans, Jr. et al. |
| 5,073,749 A | 12/1991 | Kanayama |
| 5,084,828 A | 1/1992 | Kaufman et al. |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matse et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey et al. |
| 5,374,879 A | 12/1994 | Pin et al. |
| 5,375,195 A | 12/1994 | Johnston |
| 5,400,068 A | 3/1995 | Ishida et al. |
| 5,413,693 A | 5/1995 | Redepenning |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David et al. |
| 5,442,728 A | 8/1995 | Kaufman et al. |
| 5,462,051 A | 10/1995 | Oka et al. |
| 5,474,434 A | 12/1995 | Wada |
| 5,486,853 A | 1/1996 | Baxter et al. |
| 5,510,832 A | 4/1996 | Garcia |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,598,208 A | 1/1997 | McClintock |
| 5,600,573 A | 2/1997 | Hendricks et al. |
| 5,617,539 A | 4/1997 | Ludwig et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |

(56) References Cited

U.S. PATENT DOCUMENTS

| | | |
|---|---|---|
| 5,675,229 A | 10/1997 | Thorne |
| 5,682,199 A | 10/1997 | Lankford |
| 5,684,695 A | 11/1997 | Bauer |
| 5,701,904 A | 12/1997 | Simmons et al. |
| 5,734,804 A | 3/1998 | Bergner |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Colens |
| 5,793,365 A | 8/1998 | Tang et al. |
| 5,801,755 A | 9/1998 | Echerer |
| 5,802,494 A | 9/1998 | Kuno |
| 5,836,872 A | 11/1998 | Kenet et al. |
| 5,838,575 A | 11/1998 | Lion |
| 5,844,599 A | 12/1998 | Hildin |
| 5,857,534 A | 1/1999 | DeVault et al. |
| 5,867,494 A | 2/1999 | Krishnaswamy et al. |
| 5,867,653 A | 2/1999 | Aras et al. |
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,936,679 A | 8/1999 | Kasahara et al. |
| 5,949,758 A | 9/1999 | Kober |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman, Jr. |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,140 A | 12/1999 | Carter |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,091,219 A | 7/2000 | Maruo et al. |
| 6,113,343 A | 9/2000 | Goldenberg et al. |
| 6,133,944 A | 10/2000 | Braun et al. |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,292,714 B1 | 9/2001 | Okabayashi |
| 6,304,050 B1 | 10/2001 | Skaar et al. |
| 6,314,631 B1 | 11/2001 | Pryor |
| 6,317,652 B1 | 11/2001 | Osada |
| 6,317,953 B1 | 11/2001 | Pryor |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,342,915 B1 | 1/2002 | Ozaki et al. |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,411,055 B1 | 6/2002 | Fujita et al. |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,445,964 B1 | 9/2002 | White et al. |
| 6,449,762 B1 | 9/2002 | McElvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,480,762 B1 | 11/2002 | Uchikubo et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury, Jr. et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 | 5/2003 | Granot et al. |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,604,022 B2 | 8/2003 | Parker et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,667,592 B2 | 12/2003 | Jacobs et al. |
| 6,674,259 B1 | 1/2004 | Norman et al. |
| 6,684,129 B2 | 1/2004 | Salisbury, Jr. et al. |
| 6,691,000 B2 | 2/2004 | Nagai et al. |
| 6,693,585 B1 | 2/2004 | MacLeod |
| 6,710,797 B1 | 3/2004 | McNelley et al. |
| 6,724,823 B2 | 4/2004 | Rovati et al. |
| 6,728,599 B2 | 4/2004 | Wang et al. |
| 6,763,282 B2 | 7/2004 | Glenn et al. |
| 6,764,373 B1 | 7/2004 | Osawa et al. |

(56) References Cited

U.S. PATENT DOCUMENTS

| | | |
|---|---|---|
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,856,662 B2 | 2/2005 | Glass et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe et al. |
| 6,957,712 B2 | 10/2005 | Song et al. |
| 6,958,706 B2 | 10/2005 | Chaco et al. |
| 6,965,394 B2 | 11/2005 | Gutta et al. |
| 6,990,112 B1 | 1/2006 | Brent et al. |
| 6,995,664 B1 | 2/2006 | Darling |
| 7,007,235 B1 | 2/2006 | Hussein et al. |
| 7,011,538 B2 | 3/2006 | Chang |
| 7,015,934 B2 | 3/2006 | Toyama et al. |
| RE39,080 E | 4/2006 | Johnston |
| 7,030,757 B2 | 4/2006 | Matsuhira et al. |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,292 B1 | 10/2006 | Seeger et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Lift et al. |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,222,000 B2 | 5/2007 | Wang et al. |
| 7,227,334 B2 | 6/2007 | Yang et al. |
| 7,256,708 B2 | 8/2007 | Rosenfeld et al. |
| 7,262,573 B2 | 8/2007 | Wang et al. |
| 7,283,153 B2 | 10/2007 | Provost et al. |
| 7,289,883 B2 | 10/2007 | Wang et al. |
| 7,292,257 B2 | 11/2007 | Kang et al. |
| 7,292,912 B2 | 11/2007 | Wang et al. |
| 7,305,114 B2 | 12/2007 | Wolff et al. |
| 7,317,685 B1 | 1/2008 | Flott et al. |
| 7,321,807 B2 | 1/2008 | Laski |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,363,121 B1 | 4/2008 | Chen et al. |
| 7,382,399 B1 | 6/2008 | McCall et al. |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'Rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,467,211 B1 | 12/2008 | Herman et al. |
| 7,483,867 B2 | 1/2009 | Ansari et al. |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,584,020 B2 | 9/2009 | Bruemmer et al. |
| 7,587,260 B2 | 9/2009 | Bruemmer et al. |
| 7,587,512 B2 | 9/2009 | Ta et al. |
| 7,590,060 B2 | 9/2009 | Miceli |
| 7,593,030 B2 | 9/2009 | Wang et al. |
| 7,599,290 B2 | 10/2009 | Dos Remedios et al. |
| 7,620,477 B2 | 11/2009 | Bruemmer |
| 7,624,166 B2 | 11/2009 | Foote et al. |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,647,320 B2 | 1/2010 | Mok et al. |
| 7,657,560 B1 | 2/2010 | DiRienzo |
| 7,668,621 B2 | 2/2010 | Bruemmer |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 | 4/2010 | Dawson |
| 7,719,229 B2 | 5/2010 | Kaneko et al. |
| 7,737,993 B2 | 6/2010 | Kaasila et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |
| 7,774,158 B2 | 8/2010 | Domingues Goncalves et al. |
| 7,801,644 B2 | 9/2010 | Bruemmer et al. |
| 7,813,836 B2 | 10/2010 | Wang et al. |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,861,366 B2 | 1/2011 | Hahm et al. |
| 7,873,448 B2 | 1/2011 | Takeda et al. |
| 7,885,822 B2 | 2/2011 | Akers et al. |
| 7,890,210 B2 | 2/2011 | Choi et al. |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |

(56) References Cited

U.S. PATENT DOCUMENTS

| | | |
|---|---|---|
| 7,956,894 B2 | 6/2011 | Akers et al. |
| 7,957,837 B2 | 6/2011 | Ziegler et al. |
| 7,974,738 B2 | 7/2011 | Bruemmer et al. |
| 7,982,763 B2 | 7/2011 | King |
| 7,982,769 B2 | 7/2011 | Jenkins et al. |
| 7,987,069 B2 | 7/2011 | Rodgers et al. |
| 8,073,564 B2 | 12/2011 | Bruemmer et al. |
| 8,077,963 B2 | 12/2011 | Wang et al. |
| 8,116,910 B2 | 2/2012 | Walters et al. |
| 8,126,960 B2 | 2/2012 | Obradovich et al. |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Wang et al. |
| 8,212,533 B2 | 7/2012 | Ota |
| 8,234,010 B2 | 7/2012 | Thompson et al. |
| 8,265,793 B2 | 9/2012 | Cross et al. |
| 8,271,132 B2 | 9/2012 | Nielsen et al. |
| 8,287,522 B2 | 10/2012 | Moses et al. |
| 8,292,807 B2 | 10/2012 | Perkins et al. |
| 8,301,193 B1 | 10/2012 | Lynch et al. |
| 8,320,534 B2 | 11/2012 | Kim et al. |
| 8,340,654 B2 | 12/2012 | Bratton et al. |
| 8,340,819 B2 | 12/2012 | Mangaser et al. |
| 8,348,675 B2 | 1/2013 | Dohrmann |
| 8,355,818 B2 | 1/2013 | Nielsen et al. |
| 8,374,171 B2 | 2/2013 | Cho et al. |
| 8,384,755 B2 | 2/2013 | Wang et al. |
| 8,400,491 B1 | 3/2013 | Panpaliya et al. |
| 8,401,229 B2 | 3/2013 | Hassan-Shafique et al. |
| 8,401,275 B2 | 3/2013 | Wang et al. |
| 8,423,284 B2 | 4/2013 | O'Shea |
| 8,451,731 B1 | 5/2013 | Lee et al. |
| 8,462,192 B2 | 6/2013 | O'Connell |
| 8,463,435 B2 | 6/2013 | Herzog et al. |
| 8,489,234 B2 | 7/2013 | Rew et al. |
| 8,503,340 B1 | 8/2013 | Xu |
| 8,515,577 B2 | 8/2013 | Wang et al. |
| 8,527,094 B2 | 9/2013 | Kumar et al. |
| 8,531,502 B2 | 9/2013 | Cheng et al. |
| 8,532,860 B2 | 9/2013 | Daly |
| 8,610,786 B2 | 12/2013 | Ortiz |
| 8,612,051 B2 | 12/2013 | Norman et al. |
| 8,620,077 B1 | 12/2013 | Grundmann et al. |
| 8,621,213 B2 | 12/2013 | Logan et al. |
| 8,632,376 B2 | 1/2014 | Dooley et al. |
| 8,639,797 B1 | 1/2014 | Pan et al. |
| 8,670,017 B2 | 3/2014 | Stuart et al. |
| 8,712,120 B1 | 4/2014 | Reicher et al. |
| 8,712,162 B2 | 4/2014 | Kirsch |
| 8,718,837 B2 | 5/2014 | Wang et al. |
| 8,726,454 B2 | 5/2014 | Gilbert, Jr. et al. |
| 8,836,751 B2 | 9/2014 | Ballantyne et al. |
| 8,849,679 B2 | 9/2014 | Wang et al. |
| 8,849,680 B2 | 9/2014 | Wright et al. |
| 8,861,750 B2 | 10/2014 | Roe et al. |
| 8,897,920 B2 | 11/2014 | Wang et al. |
| 8,902,278 B2 | 12/2014 | Pinter et al. |
| 8,935,005 B2 | 1/2015 | Rosenstein et al. |
| 8,965,578 B2 | 2/2015 | Versteeg et al. |
| 8,965,579 B2 | 2/2015 | Wang et al. |
| 8,983,772 B2 | 3/2015 | Lee |
| 9,001,207 B1 | 4/2015 | Webb et al. |
| 9,098,611 B2 | 8/2015 | Pinter et al. |
| 9,147,284 B2 | 9/2015 | Keene et al. |
| 9,219,857 B2 | 12/2015 | Eldon |
| 9,224,181 B2 | 12/2015 | Pinter et al. |
| 9,323,250 B2 | 4/2016 | Wang et al. |
| 9,361,021 B2 | 6/2016 | Jordan et al. |
| 9,469,030 B2 | 10/2016 | Wang et al. |
| 9,571,789 B2 | 2/2017 | Pinter et al. |
| 9,776,327 B2 | 10/2017 | Pinter et al. |
| 9,785,149 B2 | 10/2017 | Wang et al. |
| 9,902,069 B2 | 2/2018 | Farlow et al. |
| 9,974,612 B2 | 5/2018 | Pinter et al. |
| 10,061,896 B2 | 8/2018 | Jordan et al. |
| 10,334,205 B2 | 6/2019 | Pinter et al. |
| 10,591,921 B2 | 3/2020 | Wang et al. |
| 10,603,792 B2 | 3/2020 | Lai et al. |
| 10,658,083 B2 | 5/2020 | Jordan et al. |
| 2001/0002448 A1 | 5/2001 | Wilson et al. |
| 2001/0010053 A1 | 7/2001 | Ben-Shachar et al. |
| 2001/0020200 A1 | 9/2001 | Das et al. |
| 2001/0034475 A1 | 10/2001 | Flach et al. |
| 2001/0034544 A1 | 10/2001 | Mo |
| 2001/0037163 A1 | 11/2001 | Mlard |
| 2001/0048464 A1 | 12/2001 | Barnett |
| 2001/0051881 A1 | 12/2001 | Filler |
| 2001/0054071 A1 | 12/2001 | Loeb |
| 2001/0055373 A1 | 12/2001 | Yamashita |
| 2002/0013641 A1 | 1/2002 | Nourbakhsh et al. |
| 2002/0015296 A1 | 2/2002 | Howell et al. |
| 2002/0027597 A1 | 3/2002 | Sachau |
| 2002/0027652 A1 | 3/2002 | Paromtchik et al. |
| 2002/0033880 A1 | 3/2002 | Sul et al. |
| 2002/0038168 A1 | 3/2002 | Kasuga et al. |
| 2002/0044201 A1 | 4/2002 | Mexander et al. |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0085030 A1 | 7/2002 | Ghani |
| 2002/0086262 A1 | 7/2002 | Rainey |
| 2002/0091659 A1 | 7/2002 | Beaulieu et al. |
| 2002/0095238 A1 | 7/2002 | Ahlin et al. |
| 2002/0095239 A1 | 7/2002 | Wallach et al. |
| 2002/0098879 A1 | 7/2002 | Rheey |
| 2002/0104094 A1 | 8/2002 | Alexander et al. |
| 2002/0106998 A1 | 8/2002 | Presley et al. |
| 2002/0109770 A1 | 8/2002 | Terada |
| 2002/0109775 A1 | 8/2002 | White et al. |
| 2002/0111988 A1 | 8/2002 | Sato |
| 2002/0113813 A1 | 8/2002 | Yoshimine |
| 2002/0120362 A1 | 8/2002 | Lathan et al. |
| 2002/0128985 A1 | 9/2002 | Greenwald |
| 2002/0130950 A1 | 9/2002 | James et al. |
| 2002/0133062 A1 | 9/2002 | Arling et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183894 A1 | 12/2002 | Wang et al. |
| 2002/0184674 A1 | 12/2002 | Xi et al. |
| 2002/0186243 A1 | 12/2002 | Ellis et al. |
| 2002/0198626 A1 | 12/2002 | Imai et al. |
| 2003/0016726 A1 | 1/2003 | Pavlidis |
| 2003/0021107 A1 | 1/2003 | Howell et al. |
| 2003/0030397 A1 | 2/2003 | Simmons |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0053662 A1 | 3/2003 | Evoy et al. |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0112823 A1 | 6/2003 | Collins et al. |
| 2003/0114736 A1 | 6/2003 | Reed et al. |
| 2003/0114962 A1 | 6/2003 | Niemeyer |
| 2003/0120714 A1 | 6/2003 | Wolff et al. |
| 2003/0126361 A1 | 7/2003 | Slater et al. |
| 2003/0135097 A1 | 7/2003 | Wiederhold et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |

(56) References Cited

U.S. PATENT DOCUMENTS

| | | |
|---|---|---|
| 2003/0179223 A1 | 9/2003 | Ying et al. |
| 2003/0180697 A1 | 9/2003 | Kim et al. |
| 2003/0195662 A1 | 10/2003 | Wang et al. |
| 2003/0199000 A1 | 10/2003 | Valkirs et al. |
| 2003/0206242 A1 | 11/2003 | Choi |
| 2003/0212472 A1 | 11/2003 | Mckee |
| 2003/0216833 A1 | 11/2003 | Mukai et al. |
| 2003/0216834 A1 | 11/2003 | Allard |
| 2003/0220541 A1 | 11/2003 | Salisbury et al. |
| 2003/0220715 A1 | 11/2003 | Kneifel et al. |
| 2003/0231244 A1 | 12/2003 | Bonilla et al. |
| 2003/0232649 A1 | 12/2003 | Gizis et al. |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0008138 A1 | 1/2004 | Hockley et al. |
| 2004/0010344 A1 | 1/2004 | Hiratsuka et al. |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | Mclurkin et al. |
| 2004/0027243 A1 | 2/2004 | Carrender |
| 2004/0041904 A1 | 3/2004 | Lapalme et al. |
| 2004/0064080 A1 | 4/2004 | Cruz et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0140404 A1 | 7/2004 | Ohta et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0176118 A1 | 9/2004 | Strittmatter et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0236830 A1 | 11/2004 | Nelson et al. |
| 2004/0240981 A1 | 12/2004 | Dothan et al. |
| 2004/0241981 A1 | 12/2004 | Doris et al. |
| 2004/0252966 A1 | 12/2004 | Holloway et al. |
| 2004/0260790 A1 | 12/2004 | Balloni et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027400 A1 | 2/2005 | Wang et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225448 A1 | 10/2005 | Schenker |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | Mcgee et al. |
| 2005/0264649 A1 | 12/2005 | Chang et al. |
| 2005/0267826 A1 | 12/2005 | Levy et al. |
| 2005/0278446 A1 | 12/2005 | Bryant |
| 2005/0283414 A1 | 12/2005 | Fernandes et al. |
| 2005/0286759 A1 | 12/2005 | Zitnick et al. |
| 2006/0004582 A1 | 1/2006 | Claudatos et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1* | 3/2006 | Wen .............. G06K 9/00335 382/103 |
| 2006/0056837 A1 | 3/2006 | Vapaakoski |
| 2006/0058921 A1* | 3/2006 | Okamoto ........... G05D 1/0214 700/255 |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |

(56) References Cited

U.S. PATENT DOCUMENTS

| | | |
|---|---|---|
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Machi |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0184274 A1 | 8/2006 | Sakai et al. |
| 2006/0189393 A1 | 8/2006 | Edery |
| 2006/0195569 A1 | 8/2006 | Barker |
| 2006/0200518 A1 | 9/2006 | Sinclair et al. |
| 2006/0224781 A1 | 10/2006 | Tsao et al. |
| 2006/0247045 A1 | 11/2006 | Jeong et al. |
| 2006/0248210 A1 | 11/2006 | Kenoyer |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0008321 A1 | 1/2007 | Gallagher et al. |
| 2007/0016328 A1 | 1/2007 | Ziegler et al. |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0061041 A1 | 3/2007 | Zweig |
| 2007/0064092 A1 | 3/2007 | Sandbeg et al. |
| 2007/0070069 A1 | 3/2007 | Samarasekera et al. |
| 2007/0078566 A1 | 4/2007 | Wang et al. |
| 2007/0093279 A1 | 4/2007 | Janik |
| 2007/0109324 A1 | 5/2007 | Lin |
| 2007/0112700 A1 | 5/2007 | Den haan et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0129849 A1 | 6/2007 | Zini et al. |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0156286 A1 | 7/2007 | Yamauchi |
| 2007/0165106 A1 | 7/2007 | Groves et al. |
| 2007/0170886 A1 | 7/2007 | Plishner |
| 2007/0171275 A1 | 7/2007 | Kenoyer |
| 2007/0176060 A1 | 8/2007 | White et al. |
| 2007/0182811 A1 | 8/2007 | Rockefeller et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0234492 A1 | 10/2007 | Svendsen et al. |
| 2007/0238963 A1 | 10/2007 | Kaminaga et al. |
| 2007/0250212 A1 | 10/2007 | Halloran et al. |
| 2007/0255115 A1 | 11/2007 | Anglin et al. |
| 2007/0255155 A1 | 11/2007 | Drew et al. |
| 2007/0255706 A1 | 11/2007 | Iketani et al. |
| 2007/0262884 A1 | 11/2007 | Goncalves et al. |
| 2007/0271122 A1 | 11/2007 | Zaleski |
| 2007/0273751 A1 | 11/2007 | Sachau |
| 2007/0279483 A1 | 12/2007 | Beers et al. |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2007/0299316 A1 | 12/2007 | Haslehurst et al. |
| 2008/0004904 A1 | 1/2008 | Tran |
| 2008/0009969 A1 | 1/2008 | Bruemmer et al. |
| 2008/0011904 A1 | 1/2008 | Cepollina et al. |
| 2008/0021834 A1 | 1/2008 | Holla et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'andrea et al. |
| 2008/0056933 A1 | 3/2008 | Moore et al. |
| 2008/0059238 A1 | 3/2008 | Park et al. |
| 2008/0065268 A1 | 3/2008 | Wang et al. |
| 2008/0082211 A1 | 4/2008 | Wang et al. |
| 2008/0086236 A1 | 4/2008 | Saito et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0242220 A1 | 10/2008 | Wilson et al. |
| 2008/0253629 A1 | 10/2008 | Kazuno et al. |
| 2008/0255703 A1 | 10/2008 | Wang et al. |
| 2008/0263451 A1 | 10/2008 | Portele et al. |
| 2008/0263628 A1 | 10/2008 | Norman et al. |
| 2008/0267069 A1 | 10/2008 | Thielman et al. |
| 2008/0267578 A1 | 10/2008 | Zhang et al. |
| 2008/0269949 A1 | 10/2008 | Norman et al. |
| 2008/0281467 A1 | 11/2008 | Pinter |
| 2008/0285886 A1 | 11/2008 | Allen |
| 2008/0306375 A1 | 12/2008 | Sayler et al. |
| 2008/0316368 A1 | 12/2008 | Fritsch et al. |
| 2009/0021572 A1 | 1/2009 | Garudadri et al. |
| 2009/0022131 A1 | 1/2009 | Rusanen et al. |
| 2009/0022377 A1 | 1/2009 | Matsue et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0051756 A1 | 2/2009 | Trachtenberg et al. |
| 2009/0055019 A1 | 2/2009 | Stiehl et al. |
| 2009/0055023 A1 | 2/2009 | Walters et al. |
| 2009/0070135 A1 | 3/2009 | Parida et al. |
| 2009/0079812 A1 | 3/2009 | Crenshaw et al. |
| 2009/0086013 A1 | 4/2009 | Thapa |
| 2009/0089085 A1 | 4/2009 | Schoenberg |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0125584 A1 | 5/2009 | Agrawala et al. |
| 2009/0141146 A1 | 6/2009 | Guidash |
| 2009/0144425 A1 | 6/2009 | Marr et al. |
| 2009/0146882 A1 | 6/2009 | Halivaara et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0201372 A1 | 8/2009 | O'doherty et al. |
| 2009/0210090 A1 | 8/2009 | Takemitsu et al. |
| 2009/0234499 A1 | 9/2009 | Nielsen et al. |
| 2009/0237317 A1 | 9/2009 | Rofougaran |
| 2009/0240371 A1 | 9/2009 | Wang et al. |
| 2009/0248200 A1 | 10/2009 | Root |
| 2009/0259339 A1 | 10/2009 | Wright et al. |
| 2009/0278912 A1 | 11/2009 | Carter |
| 2009/0323648 A1 | 12/2009 | Park et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |

(56) References Cited

U.S. PATENT DOCUMENTS

| | | |
|---|---|---|
| 2010/0030378 A1 | 2/2010 | Choi et al. |
| 2010/0030578 A1 | 2/2010 | Siddique et al. |
| 2010/0037418 A1 | 2/2010 | Hussey et al. |
| 2010/0041998 A1 | 2/2010 | Postel |
| 2010/0051596 A1 | 3/2010 | Diedrick et al. |
| 2010/0054566 A1 | 3/2010 | Toda |
| 2010/0063636 A1 | 3/2010 | Matsumoto et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073455 A1 | 3/2010 | Iwabuchi et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0118112 A1 | 5/2010 | Nimri et al. |
| 2010/0128104 A1 | 5/2010 | Fabregat et al. |
| 2010/0131103 A1 | 5/2010 | Herzog et al. |
| 2010/0145479 A1 | 6/2010 | Griffiths |
| 2010/0153317 A1 | 6/2010 | Lee |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0217438 A1 | 8/2010 | Kawaguchi et al. |
| 2010/0228249 A1 | 9/2010 | Mohr et al. |
| 2010/0238323 A1 | 9/2010 | Englund |
| 2010/0243344 A1 | 9/2010 | Wyrobek et al. |
| 2010/0253775 A1 | 10/2010 | Yamaguchi et al. |
| 2010/0268383 A1 | 10/2010 | Wang et al. |
| 2010/0278086 A1 | 11/2010 | Pochiraju et al. |
| 2010/0286905 A1* | 11/2010 | Goncalves ........... G05D 1/0234 701/532 |
| 2010/0287006 A1 | 11/2010 | Cannon et al. |
| 2010/0299391 A1 | 11/2010 | Demarta et al. |
| 2010/0301679 A1 | 12/2010 | Murray et al. |
| 2010/0315352 A1 | 12/2010 | Hamamura et al. |
| 2010/0323783 A1 | 12/2010 | Nonaka et al. |
| 2010/0331052 A1 | 12/2010 | Watanabe |
| 2011/0022705 A1 | 1/2011 | Yellamraju et al. |
| 2011/0032373 A1 | 2/2011 | Forutanpour et al. |
| 2011/0050841 A1 | 3/2011 | Wang et al. |
| 2011/0071672 A1 | 3/2011 | Sanders et al. |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0077852 A1 | 3/2011 | Ragavan et al. |
| 2011/0107374 A1 | 5/2011 | Roberts et al. |
| 2011/0153198 A1 | 6/2011 | Kokkas et al. |
| 2011/0167151 A1 | 7/2011 | Nishiyama |
| 2011/0169832 A1 | 7/2011 | Brown et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |
| 2011/0218674 A1 | 9/2011 | Stuart et al. |
| 2011/0228112 A1 | 9/2011 | Kaheel et al. |
| 2011/0231050 A1 | 9/2011 | Goulding |
| 2011/0231796 A1 | 9/2011 | Vigil |
| 2011/0245973 A1 | 10/2011 | Wang et al. |
| 2011/0246015 A1 | 10/2011 | Cummings et al. |
| 2011/0246929 A1 | 10/2011 | Jones et al. |
| 2011/0249079 A1 | 10/2011 | Santamaria et al. |
| 2011/0280551 A1 | 11/2011 | Sammon |
| 2011/0288417 A1 | 11/2011 | Pinter et al. |
| 2011/0288682 A1 | 11/2011 | Pinter et al. |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0010518 A1 | 1/2012 | Sarel |
| 2012/0023506 A1 | 1/2012 | Maeckel et al. |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1 | 5/2012 | Krishnaswamy |
| 2012/0143906 A1 | 6/2012 | Sibbold et al. |
| 2012/0154509 A1 | 6/2012 | Erb |
| 2012/0162472 A1 | 6/2012 | Amling et al. |
| 2012/0176525 A1 | 7/2012 | Garin et al. |
| 2012/0182392 A1 | 7/2012 | Kearns et al. |
| 2012/0185095 A1 | 7/2012 | Rosenstein et al. |
| 2012/0191246 A1 | 7/2012 | Roe et al. |
| 2012/0191464 A1 | 7/2012 | Stuart et al. |
| 2012/0197464 A1 | 8/2012 | Wang et al. |
| 2012/0203731 A1 | 8/2012 | Nelson et al. |
| 2012/0215380 A1 | 8/2012 | Fouillade et al. |
| 2012/0215830 A1 | 8/2012 | Anguiano |
| 2012/0218374 A1 | 8/2012 | Matula et al. |
| 2012/0220372 A1 | 8/2012 | Cheung et al. |
| 2012/0242865 A1 | 9/2012 | Vartanian et al. |
| 2012/0245957 A1 | 9/2012 | Mathison |
| 2012/0291809 A1 | 11/2012 | Kuhe et al. |
| 2012/0316676 A1 | 12/2012 | Fouillade et al. |
| 2013/0002794 A1 | 1/2013 | Hines et al. |
| 2013/0035790 A1 | 2/2013 | Olivier et al. |
| 2013/0044180 A1 | 2/2013 | Shintani |
| 2013/0065604 A1 | 3/2013 | Werner et al. |
| 2013/0097264 A1 | 4/2013 | Bangalore et al. |
| 2013/0100269 A1 | 4/2013 | Tashiro et al. |
| 2013/0113871 A1 | 5/2013 | Ballantyne et al. |
| 2013/0141519 A1 | 6/2013 | Sayeed et al. |
| 2013/0158720 A1 | 6/2013 | Zywicki et al. |
| 2013/0166137 A1 | 6/2013 | Ahn et al. |
| 2013/0179067 A1 | 7/2013 | Trowbridge et al. |
| 2013/0198321 A1 | 8/2013 | Martin et al. |
| 2013/0246084 A1 | 9/2013 | Parmanto et al. |
| 2013/0250938 A1 | 9/2013 | Anandakumar et al. |
| 2013/0275922 A1 | 10/2013 | Pinter et al. |
| 2013/0304301 A1 | 11/2013 | Rakshit |
| 2013/0325244 A1 | 12/2013 | Wang et al. |
| 2014/0009561 A1 | 1/2014 | Sutherland et al. |
| 2014/0015914 A1 | 1/2014 | Delaunay |
| 2014/0047022 A1 | 2/2014 | Chan et al. |
| 2014/0085543 A1 | 3/2014 | Hartley et al. |
| 2014/0128103 A1 | 5/2014 | Joao et al. |
| 2014/0135990 A1 | 5/2014 | Stuart et al. |
| 2014/0139616 A1 | 5/2014 | Pinter et al. |
| 2014/0155755 A1 | 6/2014 | Pinter et al. |
| 2014/0207286 A1 | 7/2014 | Wang et al. |
| 2014/0254896 A1 | 9/2014 | Zhou et al. |
| 2014/0267549 A1 | 9/2014 | Pinter et al. |
| 2015/0055838 A1 | 2/2015 | Taylor et al. |
| 2015/0077502 A1 | 3/2015 | Jordan et al. |
| 2015/0081338 A1 | 3/2015 | Lai et al. |
| 2015/0088310 A1 | 3/2015 | Pinter et al. |
| 2015/0296177 A1 | 10/2015 | Pinter et al. |
| 2015/0314449 A1 | 11/2015 | Wang et al. |
| 2016/0229058 A1 | 8/2016 | Pinter et al. |
| 2016/0283685 A1 | 9/2016 | Jordan et al. |
| 2016/0358276 A1 | 12/2016 | Stephenson |
| 2017/0023944 A1 | 1/2017 | Wang et al. |
| 2017/0106738 A1 | 4/2017 | Gillett |
| 2017/0127019 A1 | 5/2017 | Pinter et al. |
| 2017/0144299 A1 | 5/2017 | Lafaye et al. |
| 2018/0099412 A1 | 4/2018 | Pinter et al. |
| 2018/0263703 A1 | 9/2018 | Pinter et al. |
| 2019/0066839 A1 | 2/2019 | Jordan et al. |
| 2020/0009736 A1 | 1/2020 | Pinter et al. |
| 2020/0128208 A1 | 4/2020 | Pinter et al. |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |

(56) References Cited

FOREIGN PATENT DOCUMENTS

| | | |
|---|---|---|
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 466492 A2 | 1/1992 |
| EP | 488673 A2 | 6/1992 |
| EP | 0981905 B1 | 1/2002 |
| EP | 1262142 A2 | 12/2002 |
| EP | 1304872 A1 | 4/2003 |
| EP | 1536660 A2 | 6/2005 |
| EP | 1573406 A2 | 9/2005 |
| EP | 1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1536660 A3 | 4/2008 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 A2 | 12/2010 |
| EP | 2300930 A1 | 3/2011 |
| EP | 2342651 A1 | 7/2011 |
| EP | 1279081 B1 | 1/2012 |
| GB | 2431261 A | 4/2007 |
| JP | H07-194609 A | 8/1995 |
| JP | H07-213753 A | 8/1995 |
| JP | H07-248823 A | 9/1995 |
| JP | H07-257422 A | 10/1995 |
| JP | H08-84328 A | 3/1996 |
| JP | H08-166822 A | 6/1996 |
| JP | H08-320727 A | 12/1996 |
| JP | H09-267276 A | 10/1997 |
| JP | H10-79097 A | 3/1998 |
| JP | H10-288689 A | 10/1998 |
| JP | H11-220706 A | 8/1999 |
| JP | 2000-032319 A | 1/2000 |
| JP | 2000-049800 A | 2/2000 |
| JP | 2000-079587 A | 3/2000 |
| JP | 2000-196876 A | 7/2000 |
| JP | 2001-088124 A | 4/2001 |
| JP | 2001-125641 A | 5/2001 |
| JP | 2001-147718 A | 5/2001 |
| JP | 2001-179663 A | 7/2001 |
| JP | 2001-188124 A | 7/2001 |
| JP | 2001-198865 A | 7/2001 |
| JP | 2001-198868 A | 7/2001 |
| JP | 2001-199356 A | 7/2001 |
| JP | 2002-000574 A | 1/2002 |
| JP | 2002-046088 A | 2/2002 |
| JP | 2002-101333 A | 4/2002 |
| JP | 2002-112970 A | 4/2002 |
| JP | 2002-235423 A | 8/2002 |
| JP | 2002-305743 A | 10/2002 |
| JP | 2002-321180 A | 11/2002 |
| JP | 2002-355779 A | 12/2002 |
| JP | 2004-181229 A | 7/2004 |
| JP | 2004-524824 T | 8/2004 |
| JP | 2004-261941 A | 9/2004 |
| JP | 2004-289379 A | 10/2004 |
| JP | 2005-028066 A | 2/2005 |
| JP | 2005-059170 A | 3/2005 |
| JP | 2005-111083 A | 4/2005 |
| JP | 2006-035381 A | 2/2006 |
| JP | 2006-508806 A | 3/2006 |
| JP | 2006-109094 A | 4/2006 |
| JP | 2006-224294 A | 8/2006 |
| JP | 2006-246438 A | 9/2006 |
| JP | 2007-007040 A | 1/2007 |
| JP | 2007-081646 A | 3/2007 |
| JP | 2007-232208 A | 9/2007 |
| JP | 2007-316966 A | 12/2007 |
| JP | 2009-125133 A | 6/2009 |
| JP | 2010-064154 A | 3/2010 |
| JP | 2010-532109 A | 9/2010 |
| JP | 2010-246954 A | 11/2010 |
| KR | 10-2006-0037979 A | 5/2006 |
| KR | 10-2009-0012542 A | 2/2009 |
| KR | 10-2010-0019479 A | 2/2010 |
| KR | 10-2010-0139037 A | 12/2010 |
| KR | 10-2011-0102585 A | 9/2011 |
| WO | 93/06690 A1 | 4/1993 |
| WO | 97/42761 A1 | 11/1997 |
| WO | 1998/51078 A1 | 11/1998 |
| WO | 99/67067 A1 | 12/1999 |
| WO | 2000/025516 A1 | 5/2000 |
| WO | 2000/033726 A1 | 6/2000 |
| WO | 01/31861 A1 | 5/2001 |
| WO | 2003/077745 A1 | 9/2003 |
| WO | 2004/008738 A1 | 1/2004 |
| WO | 2004/012018 A2 | 2/2004 |
| WO | 2004/075456 A2 | 9/2004 |
| WO | 2006/012797 A1 | 2/2006 |
| WO | 2006/044847 A2 | 4/2006 |
| WO | 2006/078611 A2 | 7/2006 |
| WO | 2007/041295 A2 | 4/2007 |
| WO | 2007/041038 A3 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | 2010/033666 A1 | 3/2010 |
| WO | 2010/047881 A1 | 4/2010 |
| WO | 2010/062798 A1 | 6/2010 |
| WO | 2010/065257 A1 | 6/2010 |
| WO | 2010/120407 A1 | 10/2010 |
| WO | 2011/028589 A2 | 3/2011 |
| WO | 2011/028589 A3 | 4/2011 |
| WO | 2011/097130 A2 | 8/2011 |
| WO | 2011/097132 A2 | 8/2011 |
| WO | 2011/109336 A2 | 9/2011 |
| WO | 2011/097132 A3 | 12/2011 |
| WO | 2011/149902 A2 | 12/2011 |
| WO | 2012/061932 A1 | 5/2012 |
| WO | 2013/097264 A1 | 7/2013 |
| WO | 2013/176762 A1 | 11/2013 |

OTHER PUBLICATIONS

Paulos et al., "Ubiquitous Tele-Embodiment Applications and Implications", International Journal of Human Computer Studies, vol. 46, No. 6, Jun. 1997, pp. 861-877.

Paulos, Eric John Canny, "Video of PRoP 2 at Richmond Field Station", www.prop.org Printout of Home Page of Website and two-page Transcript of the audio portion of said PRoP Video, May 2001, 2 pages.

PictureTel Corporation, "PictureTel Live200 for Windows NT Product Guide", 1997, 63 pages.

Pin et al., "A New Family of Omnidirectional and Holonomic Wheeled Platforms for Mobile Robots", IEEE Transactions an Robotics and Automation, vol. 10, No. 4, Aug. 1994, pp. 480-489.

Piquepaille, Roland, "This Blog and its RSS Feed Are Moving", Roland Piquepaille's Technology Trends, How new technologies are modifying our way of life, Oct. 31, 2004, 2 pages.

West et al., "Design of Ball Wheel Mechanisms for Omnidirectional Vehicles with Full Mobility and Invariant Kinematics", Journal of Mechanical Design, vol. 119, Jun. 1997, pp. 153-161.

Yamasaki et al., "Applying Personal Robots and Active Interface to Video Conference Systems", 6th International Conference on Human Computer Interaction, vol. B, 1995, pp. 243-248.

(56) References Cited

OTHER PUBLICATIONS

Yamauchi, Brian, "PackBot: A Versatile Platform for Military Robotics", Proceedings of SPIE for Military Robotics, 2004, pp. 228-237.
Yong et al., "Robot Task Execution with Telepresence Using Virtual Reality Technology", 1998 International Conference on Mechatronic Technology, Nov. 30-Dec. 2, 1998, pp. 1-8.
Zambroski, James, "CMU, Pitt Developing 'Nursebot'", available online at <http://www.cs.cmu.edu/~nursebot/web/press/tribunereview.html>, Oct. 27, 2000, 3 pages.
Radvision, "Making Sense of Bandwidth the Netsense Way", Network Congestion in Unmanaged Networks Bandwidth Estimation and Adaptation Techniques, White Paper, Radvision's Netsense Technology, 2010, 7 pages.
Reynolds et al., "Review of Robotic Telemedicine Utilization in Intensive Care Units (ICUs)", 11th Annual ATA Symposium, Tampa, Florida, 2011, 1 page.
Roach, Adam, "Automatic Call Back Service in SIP", Internet Engineering Task Force, Internet Draft, Category Informational, Mar. 2000, 8 pages.
Rovetta et al., "A New Telerobotic Application: Remote Laparoscopic Surgery Using Satellites and optical fiber Networks for Data Exchange", International Journal of Robotics Research, vol. 15, No. 3, Jun. 1, 1996, pp. 267-279.
Roy et al., "Towards Personal Service Robots for the Elderly", Workshop on Interactive Robots and Entertainment (WIRE 2000), available online at <http://www.ri.cmu.edu/pb_files/pub2/roy_nicholas_2000_1/roy_nicholas_2000_1.pdf>, vol. 25, Apr. 30-May 1, 2000, 7 pages.
Sachs et al., "Virtual Visit: Improving Communication for Those Who Need it Most", Studies in Health Technology and Informatics, vol. 94, Medicine Meets Virtual Reality 11, 2003, pp. 302-308.
Salemi et al., "MILO: Personal Robot Platform", IEEE/RSJ International Conference on Intelligent Robots and Systems, Aug. 2005, pp. 4089-4094.
Sandt et al., "Perceptions for a Transport Robot in Public Environments", Proceedings of the 1997 IEEE/RSJ International Conference on Intelligent Robots and Systems, vol. 1, Sep. 7-11, 1997, pp. 360-365.
Sawyer, Robert J., "Inventing the Future: 2000 Years of Discovery", available online at <http://www.sfwriter.com/pritf.htm>, Jan. 2, 2000, 2 pages.
Schaeffer et al., "Care-O-BotTM: The Concept of a System for Assisting Elderiy or Disabled Persons in Home Environments", Proceedings of the 24th Annual Conference of the IEEE Industrial Electronics Society, vol. 4, 1998, pp. 2476-2481.
Schraft et al., "Care-O-bot™: The Concept of a System for Assisting Elderly or Disabled Persons in Home Environments", IEEE Proceedings of the 24th Annual Conference of the Industrial Electronics Society, IECON '98, Aug. 31-Sep. 4, 1998, pp. 2476-2481.
Schultz et al., "Web Interfaces for Mobile Robots in Public Places", IEEE Robotics & Automation Magazine, vol. 7, No. 1, Mar. 2000, pp. 48-56.
Shimoga et al., "Touch and Force Reflection for Telepresence Surgery", Proceedings of the 16th Annual International Conference of the IEEE Engineering in Medicine and Biology Society, Nov. 1994, pp. 1049-1050.
Siegwart et al., "Interacting Mobile Robots on the Web", Proceedings of the 1999 IEEE International Conference on Robotics and Automation, May 1999, pp. 1-7.
Simmons et al., "Xavier: An Autonomous Mobile Robot on the Web", IEEE Robotics and Automation Magazine, 1999, pp. 43-48.
Stephenson, Gary, "Dr. Robot Tested at Hopkins", available online at <http://www.hopkinsmedicine.org/press/2003/august/030805.htm>, Aug. 5, 2003, 2 pages.
Stoianovici et al., "Robotic Tools for Minimally Invasive Urologic Surgery", Complications of Urologic Laparoscopic Surgery: Recognition, Management and Prevention, Dec. 2002, 17 pages.
Suplee, Curt, "Mastering the Robot", The Washington Post, Washington Post Staff Writer, Sep. 17, 2000, 5 pages.

Tahboub et al., "Dynamics Analysis and Control of a Holonomic Vehicle With Continuously Variable Transmission", Transactions of the ASME, Journal of Dynamic Systems, Measurement and Control, vol. 124, Mar. 2002, pp. 118-126.
Telepresence Research, Inc., "The Telepresence Mobile Robot System", available online at <http://www.telepresence.com/telepresence-research/TELEROBOT/>, Feb. 20, 1995, 3 pages.
Tendick et al., "Human-Machine Interfaces for Minimally Invasive Surgery", Proceedings of the 19th Annual International Conference of the IEEE Engineering in Medicine and Biology Society, vol. 6, Oct. 30-Nov. 2, 1997, pp. 2771-2776.
Theodosiou et al., "MuLVAT: A Video Annotation Tool Based on XML-Dictionaries and Shot Clustering", 19th International Conference, Artificial Neural Networks—ICANN 2009, Part II, Sep. 14-17, 2009, pp. 913-922.
Thrun et al., "Probabilistic Algorithms and the Interactive Museum Tour-Guide Robot Minerva", International Journal of Robotics Research, vol. 19, 2000, pp. 1-35.
Time, Lists, "Office Coworker Robot", Best Inventions of 2001, available online at <http://content.time.com/time/specials/packages/article/0,28804,1936165_1936255_1936640,00.html>, Nov. 19, 2001, 2 pages.
Tipsuwan et al., "Gain Adaptation of Networked Mobile Robot to Compensate QoS Deterioration", 28th Annual Conference of the Industrial Electronics Society, vol. 4, Nov. 5-8, 2002, pp. 3146-3151.
Tsui et al., "Exploring Use Cases for Telepresence Robots", 6th ACM/IEEE International Conference on Human-Robot Interaction (HRI), Mar. 2011, pp. 11-18.
Tyrrell et al., "Teleconsultation in Psychology: The Use of Videolinks for Interviewing and Assessing Elderly Patients", Age and Ageing, vol. 30, No. 3, May 2001, pp. 191-195.
Tzafestas et al., "VR-Based Teleoperation of a Mobile Robotic Assistant: Progress Report", Technical Report DEMO 2000/13, Institute of Informatics and Telecommunications, National Center for Scientific Research Demokritos, Nov. 2000, pp. 1-23.
UMASS Lowell Robotics Lab, "Robotics Lab @ UMASS Lowell", Brochure, 2011, 2 pages.
Urquhart, Kim, "InTouch's Robotic Companion 'Beams Up' Healthcare Experts", Medical Device Daily, vol. 7, No. 39, Feb. 27, 2003, pp. 1-7.
Video Middleware Cookbook, "H.350 Directory Services for Multimedia", 2 pages.
Weaver et al., "Monitoring and Controlling Using the Internet and Java", Proceedings of the 25th Annual Conference of the IEEE Industrial Electronics Society, vol. 3, 1999, pp. 1152-1158.
Weiss et al., "PEBBLES: A Personal Technology for Meeting Education, Social and Emotional Needs of Hospitalised Children", Personal and Ubiquitous Computing, vol. 5, No. 3, Aug. 2001, pp. 157-168.
Wu, et al., "Eulerian Video Magnification for Revealing Subtle Changes in the World", ACM Transactions on Graphics, vol. 31, 2012, 15 pages.
Jouppi, et al., "BiReality: Mutually-lmmersive Telepresence", 2004, 8 pages.
Screenshot Showing Google Date for Lemaire Telehealth Manual, screenshot retrieved on Dec. 18, 2014, 1 page.
Appeal from the U.S. District Court for the Central District of California in case No. 11-cv-9185, Judge Percy Anderson, Joint Appendix, vol. I of IV, Jun. 24, 2013, pp. A1-A6357.
Appeal from the U.S. District Court for the Central District of California in case No. 11-cv-9185, Judge Percy Anderson, Joint Appendix, vol. II of IV, Jun. 24, 2013, pp. A6849-A10634.
Appeal from the U.S. District Court for the Central District of California in case No. 11-cv-9185, Judge Percy Anderson, Joint Appendix, vol. III of IV, Jun. 24, 2013, pp. A10654-A15517.
Appeal from the U.S. District Court for the Central District of California in case No. 11-cv-9185, Judge Percy Anderson, Joint Appendix, vol. IV of IV, Jun. 24, 2013, pp. A15677-A18127.
Appeal from the U.S. District Court for the Central District of California in No. 11-CV-9185, Judge Percy Anderson, May 39, 2014, pp. 1-48.

(56) References Cited

OTHER PUBLICATIONS

Civil Minutes-General: Case No. CV 11-9185PA (AJWx), *InTouch Tech., Inc.* v. *VGO Commons, Inc.*, Sep. 10, 2012, 7 pages.
Defendant VGO Communications, Inc.'s Invalidity Contentions Pursuant to the Feb. 27, 2012 Civil Minute Order, May 2, 2012, 143 pages.
Defendant-Counterclaimant VGO Communications, Inc.'s Supplemental Invalidity Contentions Pursuant to the Feb. 27, 2012 Civil Minute Order, May 14, 2012, 228 pages.
"Google translation of: Innovations Report", From research project to television star: Care-O-bot in ZDF series, available online at <http://www.innovations-report.de/specials/printa.php?id=5157>, Sep. 28, 2001, 2 pages.
"Magne Charge", Smart Power for Electric Vehicles, Aug. 26, 1997, 2 pages.
"More Online Robots: Robots that Manipulate", available online at <http://ford.ieor.berkeley.edu/ir/robots_a2.html>, Retrieved on Nov. 23, 2010, Aug. 2001, 2 pages.
"MPEG File Format Summary", available online at <http://www.fileformat.info/format/mpeg/egff.htm>, Feb. 1, 2001, 8 pages.
"Nomad Scout Language Reference Manual", Nomadic Technologies, Software Version 2.7, Part No. DOC00002, Jul. 12, 1999, 47 pages.
"Nomad Scout User's Manual", Nomadic Technologies, Software Version 2. 7, Part No. DOC00004, Jul. 12, 1999, pp. 1-59.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.
PictureTel Adds New Features and Functionality to Its Award-Winning Live200 Desktop Videoconferencing System, PR Newswire Association, LLC, Gale, Cengage Learning, Jun. 13, 1997, 5 pages.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.
Reply Brief for Plaintiff-Appellant InTouch Technologies, Inc., Appeal from the U.S. District Court for the Central Districl of California in Case No. 11-cv-9185, Judge Percy Anderson, Jun. 14, 2013, 39 pages.
"Robart I, II, III", Spawar, Systems Center Pacific, 1998, 8 pages.
Using your Infrared Cell Phone Camera, available online at <http://www.catsdomain.com/xray/about.htm>, Courtesy of Internet Wayback Machine, Jan. 30, 2010, 4 pages.
Ivanova, Natali, "Master's Thesis: Internet Based Interface for Control of a Mobile Robot", Department of Numerical Analysis and Computer Science, 2003, 59 pages.
Jacobs et al., "Applying Telemedicine to Outpatient Physical Therapy", AMIA, Annual Symposium Proceedings, 2002, 1 page.
Jenkins et al., "Telehealth Advancing Nursing Practice", Nursing Outlook, vol. 49, No. 2, Mar. 2001, pp. 100-105.
Johanson, Mathias, "Supporting Video-Mediated Communication Over the Internet", Depailment of Computer Engineering, Chalmers University of Technology, Gothenburg, Sweden, 2003, 222 pages.
ACM Digital Library Record, "Autonomous Robots vol. 11 Issue 1", available online at <http://dl.acm.org/citation.cfm?id=591550&picked=prox&cfid=360891374&cftoken=35225929>, Jul. 2001, 2 pages.
Active Media, Inc., "Saphira Software Manual", Saphira Version 5.3, 1997, 105 pages.
Activmedia Robotics, "Pioneer 2/PeopleBot TM", Operations Manual, Version 9, Oct. 2001, 78 pages.
Adams, Chris, "Simulation of Adaptive Behavior (SAB'02)", Mobile Robotics Research Group, The Seventh International Conference, retrieved on Jan. 22, 2014, available online at <http://www.dai.ed.ac.uk/groups/mrg/MRG.html>, Aug. 4-11, 2002, 1 page.
Ando et al., "A Multimedia Self-service Terminal with Conferencing Functions", Robot and Human Communication, Tokyo, Proceedings of 4th IEEE International Workshop, Jul. 5-7, 1995, pp. 357-362.

Android Amusement Corp., "What Marketing Secret Renting Robots from Android Amusement Corp!", (Advertisement), 1982, 1 page.
Apple Inc., "I Phone", iPhone Series, XP002696350, Sep. 21, 2012, pp. 1-29.
Applebome, Peter, "Planning Domesticated Robots for Tomorrow's Household", New York Times, available online at <http://www.theoldrobots.com/images17/dc17.jpg>, Mar. 4, 1982, pp. 21 and 23.
Bar-Cohen et al., "Virtual Reality Robotic Telesurgery Simulations Using MEMICA Haptic System", Proceedings of SPIE's 8th Annual International Symposium on Smart Structures and Materials, Mar. 5-8, 2001, pp. 1-7.
Barrett, Rick, "Video Conferencing Business Soars as Companies Cut Travel; Some Travel Cuts Are Permanent", available online at <http://www.ivci.com/international_videoconferencing_news_videoconferencing_news_19.html>, May 13, 2002, 2 pages.
Bartholomew, "Pharmacy Apothecary", available online at <http://classes.bnf.fr/ema/grands/034.htm>, retrieved on Jul. 26, 2012, 2 pages.
Bauer et al., "Remote Telesurgical Mentoring: Feasibility and Efficacy", IEEE, Proceedings of the 33rd Hawaii International Conference on System Sciences, 2000, pp. 1-9.
Bauer, Jeffrey C., "Service Robots in Health Care: The Evolution of Mechanical Solutions to Human Resource Problems", Bon Secours Health System Inc., Technology Early Warning System(TEWS), Future of Service Robots in Health Care, Jun. 2003, pp. 1-10.
Bischoff, Rainer, "Design Concept and Realization of the Humanoid Service Robot HERMES", Field and Service Robotics, Springer, 1998, pp. 485-492.
Blackwell, Gerry, "Video: A Wireless LAN Killer App?", available online at <http://www.wi-fiplanet.com/columns/article.php/1010261/Video-A-Wireless-LAN-Killer>, Apr. 16, 2002, 4 pages.
Blaer et al., "TopBot: Automated Network Topology Detection With a Mobile Robot", IEEE, Proceedings of the 2003 International Conference on Robotics 7 Automation, Taipei, Taiwan, Sep. 14-19, 2003, pp. 1582-1587.
Bradner, S., "The Internet Standards Process—Revision 3", Network Working Group, Request for Comments: 2026, BCP: 9, Obsoletes: 1602, Category: Best Current Practice, Oct. 1996, pp. 1-36.
Brenner, Pablo, "A technical tutorial on the IEEE 802.11 protocol", Breezecom Wireless Communications, 1997, pp. 1-24.
Breslow et al., "Effect of a Multiple-Site Intensive Care Unit Telemedicine Program on Clinical and Economic Outcome an Alternative Paradigm for Intensivist Starnng", Critical Care Med, vol. 32, No. 1, Jan. 2004, pp. 31-38.
Brooks, Rodney, "A Robust Layered Control System for a Mobile Robot", IEEE, Journal of Robotics and Automation, vol. 2, No. 1, Mar. 1986, pp. 14-23.
Brooks, Rodney Allen, "Remote Presence", Abstracts from Flesh & Machines, How Robots Will Change US, Feb. 2002, pp. 131-147.
Celi et al., "The eICU: It's Not Just Telemedicine", Critical Care Medicine vol. 29, No. 8 (Supplement), Aug. 2001, pp. 183-189.
Cheetham et al., "Interface Development for a Child's Video Conferencing Robot", available online at <www.ryerson.ca/pebbles/publications/paper-iea200hfes-last.pdf>, 2000, 4 pages.
Christensen et al., "BeeSoft User's Guide and Reference", Robots for the Real World™, Real World Interface, Inc ., Sep. 26, 1997, 203 pages.
Chu et al., "Detection of Target Mobile Signal Strength", Technical Development, Motorola Inc, Jan. 1999, pp. 205-206.
Jouppi et al., "BiReality: Mutually-Immersive Telepresence", Proceedings of the 12th Annual ACM International Conference on Multimedia, Oct. 10-16, 2004, pp. 860-867.
Jouppi et al., "First Steps Towards Mutually-lmmersive Mobile Telepresence", Proceedings of the 2002 ACM Conference on Computer Supported Cooperative Work, Nov. 16-20, 2002, pp. 354-363.
Kanehiro et al., "Virtual Humanoid Robot Platform to Develop Controllers of Real Humanoid Robots without Porting", IEEE/RSJ International Conference on Intelligent Robots and Systems, vol. 2, 2001, pp. 1093-1099.
Kaplan et al., "An Internet Accessible Telepresence", Multimedia Systems Journal, vol. 5, 1996, 7 pages.

(56) References Cited

OTHER PUBLICATIONS

Keller et al., "Raven Interface Project", The National Aviary's Teleconferencing Carnegie Mellon University Robot, Interaction and Visual Interface Design, School of Design, Carnegie Mellon University, 2001, 8 pages.

Khatib et al., "Robots in Human Environments", Proceedings International Conference on Control, Automation, Robotics, and Vision ICRACV2000, 1999, 15 pages.

Knight et al., "Active Visual Alignment of a Mobile Stereo Camera Platform", IEEE International Conference on Robotics and Automation, vol. 4, Apr. 24-28, 2000, pp. 3203-3208.

Koenen, Rob, "MPEG-4: a Powerful Standard for Use in Web and Television Environments", (KPN Research), available online at <http://www.w3.org/Architecture/1998/06/Workshop/paper26>, Jul. 1, 1998, 4 pages.

Kurlowicz et al., "The Mini Mental State Examination (MMSE)", Try This: Best Practices in Nursing Care to Older Adults, A series from the Hartford Institute of Geriatric Nursing, Issue No. 3, Jan. 1999, 2 pages.

Kuzuoka et al., "Can the GestureCam be a Surrogate?", Proceedings of the Fourth European Conference on Computer-Supported Cooperative Work, 1995, pp. 181-196.

Lane, Earl, "Automated Aides", Available online at <http://www.cs.cum.edu/nursebot/web/press/nd4380.htm>, Oct. 17, 2000, 4 pages.

Lee et al., "A Novel Method of Surgical Instruction: International Telementoring", World Journal of Urology, vol. 16, No. 6, Dec. 1998, pp. 367-370.

Leifer et al., "VIPRR: A Virtually In Person Rehabilitation Robot", Proceedings of 1997 International Conference on Rehabilitation Robotics, Apr. 14-15, 1997, 4 pages.

Lemaire, Edward, "Using Communication Technology to Enhance Rehabilitation Services: A Solution Oriented User Manual", Institute for Rehabilitation Research and Development, Terry Fox Mobile Clinic, The Rehabilitation Centre, Ottawa, Ontario, Canada, Version 2.0, available online at <http://www.irrd.ca/telehealth/distfile/distman_v2_1.pdf>, 1998-2001, 104 pages.

Library of Congress, "008—Fixed-Length Data Elements (NR)", MARC 21 Format for Classification Data, available online at <http://www.loc.gov/marc/classification/cd008.html>, Jan. 2000, pp. 1-14.

Lim et al., "Control to Realize Human-Like Walking of a Biped Humanoid Robot", IEEE International Conference on Systems, Man, and Cybernetics, 2000, vol. 5, 2000, pp. 3271-3276.

Linebarger et al., "Concurrency Control Mechanisms for Closely Coupled Collaboration in Multithreaded Virtual Environments", Department of Computer Science and Engineering, Lehigh University, vol. 13, 2004, 40 pages.

Long, William F., "Robot Navigation Technology", available online at <http://www.atp.nist.gov/eao/sp950-1/helpmate.htm>, Mar. 1999, 3 pages.

Luna, Nancy, "Robot a New Face on Geriatric Care", ocregister.com, Aug. 6, 2003, 3 pages.

Mack, Michael J., "Minimally Invasive and Robotic Surgery", The Journal of the American Medical Association, vol. 285, No. 5, 2001, pp. 568-572.

Mair, G. M., "Telepresence—The Technology and its Economic and Social Implications", Technology and Society, 1997. 'Technology and Society at a Time of Sweeping Change'. Proceedings, 1997 International Symposium, Jun. 20-21, 1997, pp. 118-124.

Martin, Anya, "Brighter Days Ahead", Assisted Living Today, vol. 9, Nov./Dec. 2002, pp. 19-22.

McCardle et al., "The Challenge of Utilizing New Technology in Design Education", Loughborough University, IDATER 2000, 2000, pp. 122-127.

Meng et al., "E-Service Robot in Home Healthcare", Proceedings of the 2000 IEEE/RSJ, International Conference on Intelligent Robots and Systems, 2000, pp. 832-837.

Metz, Cade, "HP Labs", available online at <http://www.pcmag.eom/article2/0,2817,1130820,00.asp>, Jul. 1, 2003, 4 pages.

Michaud, Anne, "Introducing "Nursebot"", available online at <http://www.cs.cmu.edu/nursebot/web/press/globe 301/index.html>, 2001, 4 pages.

Microsoft Corporation, Inc., "Microsoft NetMeeting 3 Features excerpt from Official Microsoft NetMeeting 3.0 Book", available online at <http://technet.microsoft.com/en-us/library/cc723477.aspx>, 2012, 6 pages.

Minsky, Marvin, "Telepresence", OMNI Magazine, Jun. 1980, 6 pages.

Montemerlo, Reddy Whittaker, "Telepresence: Experiments in Next Generation Internet", available online at <http://www.ri.cmu.edu/creative/archives.htm>, Oct. 20, 1998, 3 pages.

Murphy, Robin R., "Introduction to AI Robotics", A Bradford Book, The MIT Press, Cambridge, Massachusetts, London, England, 2000, 487 pages.

Nakajima et al., "A Multimedia Teleteaching System using an Electronic Whiteboard for Two Way Communication of Motion Videos and Chalkboards", 2nd IEEE International Workshop on Robot and Human Communication, 1993, pp. 436-441.

Nakazato et al., "Group-Based Interface for Content-Based Image Retrieval", Proceedings of the Working Conference on Advanced Visual Interfaces, 2002, pp. 187-194.

Nakazato et al., "ImageGrouper: A Group-Oriented User Interface for Content-Based Image Retrieval and Digital mage Arrangement", Journal of Visual Languages & Computing, vol. 14, No. 4, Aug. 2003, pp. 45-46.

Nersc, "Berkeley Lab's RAGE Telepresence Robot Captures R&D100 Award", Available online at <https://www.nersc.gov/news-publications/news/nersc-center-news/2002/berkeley-lab-s-rage-telepresence-robot-captures-r-and-d100-award/>, Jul. 2, 2002, 2 pages.

Nomadic Technologies Inc., "Nomad XR4000 Hardware Manual", Release 1.0, Mar. 1999, 34 pages.

Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.

North, Michael, "Telemedicine: Sample Script and Specifications for a Demonstration of Simple Medical Diagnosis and Treatment Using Live Two-Way Video on a Computer Network", Greenstar Corporation, 1998, 5 pages.

Ogata et al., "Development of Emotional Communication Robot: WAMOEBA-2R—Experimental Evaluation", Proceedings of the 2000 IEEE/RSJ International Conference on Intelligent Robots and Systems, vol. 1, 2000, pp. 175-180.

Ogata et al., "Emotional Communication Robot: WAMOEBA-2R—Emotion Model and Evaluation Experiments", Proceedings of the International Conference on Humanoid Robots, 2000, pp. 1-16.

Oh et al., "Autonomous Battery Recharging for Indoor Mobile Robots", Proceedings of Australian Conference on Robotics and Automation, 2000, pp. 1-6.

Ojha, Anand K., "An application of Virtual Reality in Rehabilitation", Proceedings of the 1994 IEEE Southeastcon 94. Creative Technology Transfer—A Global Affair, Apr. 1994, pp. 4-6.

Osborn, Jim, "Quality of Life Technology Center", QoLT Research Overview: A National Science Foundation Engineering Research Center, Carnegie Mellon University of Pittsburgh, 2 pages.

Panusopone et al., "Performance comparison of MPEG-4 and H.263+ for streaming video applications", Circuits Systems Signal Processing, vol. 20, No. 3, 2001, pp. 293-309.

Paulos et al., "A World Wide Web Telerobotic Remote Environment Browser", Available online at <http://www.w3.org/Conferences/WWW4/Papers/326/>, 1995, 15 pages.

Paulos et al., "Designing Personal Tele-Embodiment", Proceedings of IEEE International Conference on Robotics and Automation, vol. 4, May 16-20, 1998, pp. 3173-3178.

Paulos, Eric J., "Personal Tele-Embodiment", Dissertation, Doctor of Philosophy in Computer Science in the Graduate Division of the University of California at Berkeley, 2001, 282 pages.

Weiss et al., "Telework and Video-Mediated Communication: Importance of Real-Time, Interactive Communication for Workers with Disabilities", available online at <http://www.telbotics.com/research_3.htm>, retrieved on Nov. 23, 2010, 3 pages.

(56) References Cited

OTHER PUBLICATIONS

Zamrazil, Kristie, "Telemedicine in Texas: Public Policy Concerns", Focus Report, House Research Organization, Texas House of Representatives, No. 76-22, May 5, 2000, pp. 1-16.
Zipperer, Lorri, "Robotic Dispensing System", ISMP Medication Safety Alert!, vol. 4, No. 17, Aug. 25, 1999, 2 pages.
Zorn, Benjamin G., "Ubiquitous Telepresence", Department of Computer Science, University of Colorado, 1996, 13 pages.
Cleary et al., "State of the Art in Surgical Robotics: Clinical Applications and Technology Challenges", Feb. 24, 2002, pp. 1-26.
CMU Course 16X62, "Robot user's manual", (describing the Nomad Scout), Carnegie Mellon University, Feb. 1, 2001, 11 pages.
CNN, "Floating 'Droids' to Roam Space Corridors of the Future", Available online at <http://edition.cnn.com/2000/TECH/space/01/12/psa/>, Jan. 12, 2000, 3 pages.
cnn.com, "Paging Dr.Robot: Machine Helps Doctors with Patients", Sep. 30, 2003, 3 pages.
Crowley, Susan L., "Hello to Our Future", AARP Bulletin, Jan. 2000, 12 pages.
Dalton, Barnaby, "Techniques for Web Telerobotics", PhD Thesis, University of Western Australia, 2001, 243 pages.
Dario et al., "A Robot Workstation for Diagnosis and Physical Therapy", IEEE Catalog No. 88TH0234-5, 1989, pp. 67-72.
Davies, Brian, "Robotics in Minimally Invasive Surgery", IEE Colloquium on Through the Keyhole: Microengineering n Minimally Invasive Surgery, 1995, pp. 1-2.
Davis, Erik, "Telefriend, Meet iRobot, The Smartest Webcam on Wheels", Wired Magazine, Issue 8.09, Available online at <http://www.wired.com/wired/archive/8.09/irobot.html?pg=1&topic=&topic_set=>, Sep. 2000, 3 pages.
Dean et al., "1992 AAAI Robot Exhibition and Competition", Articles, AI Magazine, vol. 14, No. 1, 1993, 15 pages.
Digiorgio, James, "Is Your Emergency Department of the Leading Edge?", Chicago Hospital News, vol. 2, No. 12, 2005, 3 pages.
Dudenhoeffer et al., "Command and Control Architectures for Autonomous Micro-Robotic Forces", FY00 Project Report, Idaho National Engineering and Environmental Laboratory Human Systems Engineering and Sciences Department, Idaho Falls, Apr. 2001, 43 pages.
Elhajj et al., "Real-Time Haptic Feedback in Internet-Based Telerobotic Operation", IEEE International Conference on Electro/Information Technology, available online at <http://www.egr.msu.edu/~ralab-web/cgi_bin/internet-teleoperation.php>, Jun. 2000, 10 pages.
Elhajj et al., "Supermedia in Internet-Based Telerobotic Operations", Management of Multimedia on the InternetLecture Notes in Computer Science, Springer-Verlag Berlin Heidelberg, vol. 2216, Oct. 29-Nov. 1, 2001, pp. 359-372.
Elhajj et al., "Synchronization and Control of Supermedia Transmission via the Internet", Proceedings of 2001 International Symposium on Intelligent Multimedia Video and Speech Processing, May 2-4, 2001, pp. 320-323.
Ellison et al., "Telerounding and Patient Satisfaction Following Surgery", vol. 199, No. 4, Oct. 2004, pp. 523-530.
Evans et al., "The Trackless Robotic Courier", PYXIS HelpMate®, 2007, 3 pages.
Fels et al., "Developing a Video-Mediated Communication System for Hospitalized Children", Telemedicine Journal, vol. 5, No. 2, 1999, 30 pages.
Fetterman et al., "Videoconferencing Over the Internet", 2001, 8 pages.
Fiorini et al., "Health Care Robotics: A Progress Report", IEEE International Conference on Robotics and Automation, Apr. 20-25, 1997, pp. 1271-1276.
Fong, Terrence, "Collaborative Control: A Robot-Centric Model for Vehicle Teleoperation", Doctoral Dissertation, Technical Report CMU-RI-TR-01-34, Robotics Institute, Carnegie Mellon University, Nov. 2001, 197 pages.
Fulbright et al., "SWAMI: An Autonomous Mobile Robot for Inspection of Nuclear Waste of Storage Facilities", Autonomous Robots, vol. 2, 1995, pp. 225-235.
Gaidioz et al., "Synchronizing Network Probes to Avoid Measurement Intrusiveness with the Network Weather Service", Proceedings of the Ninth International Symposium on High-Performance Distributed Computing, 2000, pp. 147-154.
Garner et al., "The Application of Telepresence in Medicine", BT Technology Journal, vol. 15, No. 4, Oct. 1, 1997, pp. 181-187.
Ghiasi et al., "A Generic Web-based Teleoperations Architecture: Details and Experience", Proceedings of SPIE, Telemanipulator and Telepresence Technologies VI, vol. 3840, No. 234, Sep. 19, 1999, 14 pages.
Goldberg et al., "Collaborative Teleoperation via the Internet", IEEE International Conference on Robotics and Automation (ICRA), vol. 2, 2000, pp. 2019-2024.
Goldberg et al., "Desktop Teleoperation via the World Wide Web", IEEE International Conference on Robotics and Automation, vol. 1, May 21-27, 1995, pp. 654-659.
Goldenberg et al., "Telemedicine in Otolaryngology", American Journal of Otolaryngology, vol. 23,No. 1, 2002, pp. 35-43.
Goldman, Lea, "Machine Dreams", available online at <http://www.forbes.com/global/2002/0527/043.html>, May 27, 2002, 5 pages.
Gostai, "Gostai Jazz: Robotic Telepresence", available online at <http://www.robotshop.com/media/files/pdf/gostai-jazz-information-sheet.pdf>, 4 pages.
Gump, Michael D., "Robot Technology Improves VA Pharmacies", U.S. Medicine Informational Central, Jul. 2001, 3 pages.
Al-Kassab et al., "A Review of Telemedicine", Journal of Telemedicine and Telecare, vol. 5, Supplement 1, 1999, pp. 103-106.
Han et al., "Construction of an Omnidirectional Mobile Robot Platform Based on Active Dual-Wheel Caster Mechanisms and Development of a Control Simulator", Journal of Intelligent and Robotic Systems, vol. 29, Issue 3, Nov. 2000, pp. 257-275.
Handley et al., "RFC 2327—SDP: Session Description Protocol", available online at <http://www.faqs.org/rfcs/rfc2327.html>, Apr. 1998, 22 pages.
Hanebeck et al., "ROMAN: A Mobile Robotic Assistant for Indoor Service Applications", IEEE/RSJ International Conference on Intelligent Robots and Systems, vol. 2, Sep. 7-11, 1997, pp. 518-525.
Harmo et al., "Moving Eye-Interactive Telepresence Over Internet With a Ball Shaped Mobile Robot", available online at <http://automation.tkk.fi/files/tervetaas/MovingEye4.pdf>, 2000, 6 pages.
Haule et al., "Control Scheme for Delayed Teleoperation Tasks", IEEE Pacific Rim Conference on Communications, Computers, and Signal Processing, May 17-19, 1995, pp. 157-160.
Hees, William P., "Communications Design for a Remote Presence Robot", CSCI E-131b, Final Project, Jan. 14, 2002, 12 pages.
Herias et al., "Flexible Virtual and Remote Laboratory for Teaching Robotics", Current Developments in Technology-Assisted Education, Jun. 2006, pp. 1959-1963.
Holmberg et al., "Development of a Holonomic Mobile Robot for Mobile Manipulation Tasks", International Journal of Robotics Research, vol. 19, No. 11, Nov. 2000, pp. 1066-1074.
Ishiguro et al., "Integrating a Perceptual Information Infrastructure with Robotic Avatars: A Framework for Tele-Existence", IEEE/RSJ International Conference on Intelligent Robots and Systems, vol. 2, 1999, pp. 1032-1038.
Ishihara et al., "Intelligent Microrobot DDS (Drug Delivery System) Measured and Controlled by Ultrasonics", Intelligent Robots and Systems '91. Intelligence for Mechanical Systems, IEEE/RSJ International Workshop, vol. 2, Nov. 3-5, 1991, pp. 1145-1150.
ITU, "Call Completion Supplementary Services for H.323", ITU-T, Telecommunication Standardization Sector of ITU, H.450.9, Series H: Audiovisual And Multimedia Systems, Nov. 2000, 63 pages.
ITU, "Call Intrusion Supplementary Service for H.323", ITU-T, Telecommunication Standardization Sector of ITU, H.450.11, Series H: Audiovisual and Multimedia Systems, Mar. 2001, 59 pages.
ITU, "Packet-Based Multimedia Communications Systems", ITU-T, Telecommunication Standardization Sector of ITU, H.323, Series H: Audiovisual and Multimedia Systems, Feb. 1998, 128 pages.
ITU, "Transmission of Non-Telephone Signals: A Far End Camera Control Protocol for Videoconferences Using H.224", ITU-T, Telecommunication Standardization Sector of ITU, H.281, Nov. 1994, 12 pages.

(56) References Cited

OTHER PUBLICATIONS

Paulos, Eric John, "Personal Tele-Embodiment", OskiCat Catalog Record, UCB Library Catalog, 2001, 3 pages.
Paulos et al., "Personal Tele-Embodiment", Chapter 9 in Goldberg, et al., ed. "Beyond webcams", MIT Press, Jan. 4, 2002, pp. 155-167.
Paulos, Eric John, "Personal Tele-Embodiment", Introductory and cover pages from 2001 Dissertation including Contents table, together with e-mails relating thereto from UC Berkeley Libraries, as shelved at UC Berkeley Engineering Library (Northern Regional library Facility), May 8, 2002, 25 pages (including 4 pages of e-mails).
Paulos et al., "PRoP: Personal Roving Presence", ACM:CHI Proceedings of CHI '98, 1998, 8 pages.

\* cited by examiner

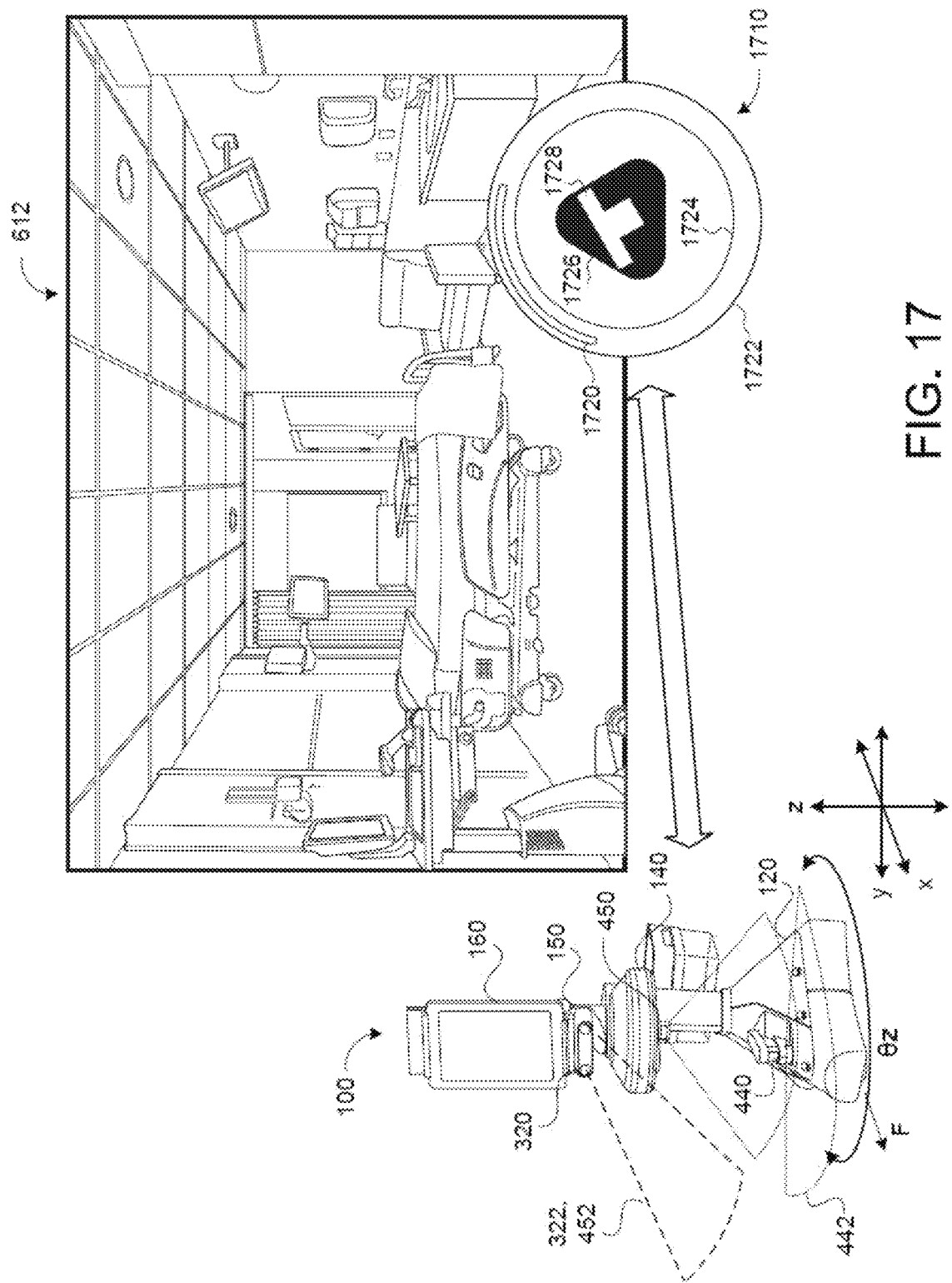

TIME-DEPENDENT NAVIGATION OF TELEPRESENCE ROBOTS

CROSS REFERENCE TO RELATED APPLICATIONS

This application is a continuation of U.S. patent application Ser. No. 13/958,413, filed Aug. 2, 2013, which is a continuation-in-part of U.S. patent application Ser. No. 13/360,579 filed on Jan. 27, 2012, which claims priority under 35 U.S.C. § 119(e) to U.S. Provisional Application No. 61/437,433 filed on Jan. 28, 2011, all of which are hereby incorporated by reference in their entireties. In addition, U.S. Patent Publication No. 2007/0199108 and U.S. Pat. No. 6,535,793 are also incorporated herein by reference in their entireties.

TECHNICAL FIELD

This disclosure relates to mobile telepresence robots.

BACKGROUND

A robot is generally an electro-mechanical machine guided by a computer or electronic programming. Telepresence robots and autonomous vehicle robots have the capability to move around in their environment and are not fixed to one physical location. An example of a telepresence robot that is in common use today is an automated guided vehicle or automatic guided vehicle (AGV). An AGV is generally a telepresence robot that follows markers or wires in the floor, or uses a vision system or lasers for navigation. Telepresence robots can be found in industry, military and security environments. They also appear as consumer products, for entertainment or to perform certain tasks like home assistance.

SUMMARY

One aspect of the disclosure provides a telepresence robot system including a drive system configured to move the telepresence robot according to drive instructions; a control system in communication with the drive system, the control system configured to generate drive instructions to cause the drive system to move the telepresence robot along a navigation path; a mapping module in communication with the control system, the mapping module configured to access a map data source, the map data source including a map representative of robot-navigable areas of a robot operating surface and a plurality of time-dependent navigation tags, each time-dependent navigation tag being a data structure comprising spatial coordinates locatable relative to the map and tag information having a time-dependent robot action modifier, wherein the spatial coordinates are associated with robot-navigable areas of the operating surface, a positioning system in communication with the control system configured to provide positioning information associated with a current position; a tag identification system configured to identify at least one time-dependent navigation tag associated with the navigation path of the telepresence robot; and wherein the telepresence robot system is configured to be triggered to perform at least one of various actions (e.g., plan a navigation path, sound an alarm that the telepresence robot is approaching, fire an actuator to move the robot, for example, drive the robot, turn the head of the robot, etc.) based, at least in part, on the time-dependent action modifier associated with an identified time-dependent navigation tag.

In some embodiments, the telepresence robot system may include a navigation system configured to generate a navigation path, the navigation path comprising a sequence of coordinates from a current position on the map to a desired position on the map, wherein the navigation system is configured to be triggered to plan the navigation path based, at least in part, on the time-dependent action modifier associated with an identified time-dependent navigation tag and wherein the navigation system is configured to generate the navigation path by generating a plurality of potential navigation paths, wherein each potential navigation path has an associated cost based on the time-dependent action modifiers associated with the time-dependent navigation tags along the respective potential navigation path and selecting the navigation path from the plurality of potential navigation path based on the associated cost.

Other aspects of the disclosure provide a telepresence robot system including a local terminal and a remote telepresence robot. The local terminal may include an electronic display, a processor, and a memory in communication with the processor, the memory comprising instructions executable by the processor. The executable instructions may be configured to cause the processor to retrieve at least a portion of a plan view map representative of robot-navigable areas of a robot operating surface; retrieve at least one of a plurality of tags, each of the plurality of tags comprising tag coordinates describing the relative location of the tag and tag information, which may include a tag annotation; receive a video feed from an imaging system of a remote telepresence robot; receive positioning information; display the video feed from the imaging system of the remote telepresence robot; display the plan view map with an indication of a current position of the telepresence robot on the plan view map; display a rendition of the tag annotation of the at least one tag on at least one of the plan view map and the video feed using the tag coordinates; and transmit one or more commands to the remote telepresence robot.

In some embodiments, the instructions executable by the processor are further configured to cause the processor to determine a distortion (e.g., a coordinate transformation between a two-dimensional coordinate system and a three-dimensional coordinate system) between the plan view map and the video feed received from the imaging system of the remote telepresence robot; apply the distortion to the tag coordinates of the at least one tag to determine corresponding video coordinates and perspective data describing a location and perspective of the at least one tag relative to the video feed; and display a three-dimensional rendition of the tag annotation of the at least one tag overlaid on the video feed using the tag video coordinates.

In some embodiments, the three-dimensional rendition of the tag annotation may be dynamically re-rendered based on the current position of the remote telepresence robot and a perspective of the at least one tag relative to the video feed.

In some embodiments, the three-dimensional rendition of the tag annotation may be overlaid on the video feed with respect to an object detected in the video feed.

In some embodiments, the three-dimensional rendition of the tag annotation may be overlaid along a wall detected in the video feed.

In some embodiments, the tag information of the at least one tag comprises a telepresence robot action modifier and the robot action modifier may be configured to provide execution instructions to a control system of the telepresence robot to execute a first action in response to the telepresence robot being within a predetermined range of the tag coordinates of the at least one tag.

In some embodiments, the instructions executable by the processor are further configured to cause the processor to transmit the execution instruction to the control system of the telepresence robot when the telepresence robot is within a predetermined range of the tag coordinates of the at least one tag.

In some embodiments, the robot action modifier further comprises instructions regarding one of a time and a location on the plan view map that the control system of the telepresence robot should execute the first action.

In some embodiments, the instructions executable by the processor are further configured to cause the processor to receive a sequence of coordinates relative to the plan view map forming a path along which the remote telepresence robot has traveled; store the sequence of coordinates forming the path as a path tag comprising tag coordinates and tag information, which may include a tag annotation; retrieve the path tag when the remote telepresence robot arrives within a predetermined distance of the tag coordinates; and display a rendition of the tag annotation of the path tag on at least one of the plan view map and the video feed using the tag coordinates.

In some embodiments, the telepresence robot system local terminal further comprises at least one user input device and the sequence of coordinates forming the path may be provided by the user input device.

In some embodiments, the sequence of coordinates forming the path may be provided by the remote telepresence robot.

In some embodiments, the telepresence robot system further comprises a communication system configured to facilitate communication between the telepresence robot system local terminal and the remote telepresence robot.

In some embodiments, the local terminal further comprises at least one user input device and the user input device may be configured to allow a user to provide an indication of a desired destination of the remote telepresence robot on at least one of the plan view map and the video feed from the imaging system of the remote telepresence robot; and the command transmitted to the remote telepresence robot comprises the desired destination.

In some embodiments, the sequence of coordinates forming the robot path may be based at least in part on tagging information associated with the at least one tag.

In some embodiments, the instructions executable by the processor are further configured to cause the processor to determine a sequence of coordinates relative to the plan view map to create a robot path between the current position of the remote telepresence robot and the desired destination of the remote telepresence robot and the command transmitted to the remote telepresence robot comprises the sequence of coordinates forming the robot path.

In some embodiments, the instructions executable by the processor are further configured to cause the processor to display the sequence of coordinates forming the robot path overlaid on the plan view map.

In some embodiments, the instructions executable by the processor are further configured to cause the processor to determine a distortion (e.g., a coordinate transformation between a two-dimensional coordinate system and a three-dimensional coordinate system) between the plan view map and the video feed received from the imaging system of the remote telepresence robot; apply the distortion to the sequence of coordinates forming the robot path to determine corresponding video coordinates and perspective data describing a location and perspective of the sequence of coordinates relative to the video feed; and display a three-dimensional rendition of the sequence of coordinates forming the robot path overlaid on the video feed.

In some embodiments, the three-dimensional rendition of the sequence of coordinates forming the robot path may be overlaid on the video feed with respect to a floor detected in the video feed.

In some embodiments, the instructions executable by the processor are further configured to cause the processor to receive a sequence of coordinates relative to the plan view map from a navigation system of the remote telepresence robot, the sequence of coordinates forming a robot path between the current position of the remote telepresence robot and a desired destination of the remote telepresence robot; and display the sequence of coordinates forming the robot path overlaid on the plan view map.

In some embodiments, the instructions executable by the processor are further configured to cause the processor to determine a distortion (e.g., a coordinate transformation between a two-dimensional coordinate system and a three-dimensional coordinate system) between the plan view map and the video feed received from the imaging system of the remote telepresence robot; apply the distortion to the sequence of coordinates forming the robot path to determine corresponding video coordinates and perspective data describing the location and perspective of the sequence of coordinates relative to the video feed; and display a three-dimensional rendition of the sequence of coordinates forming the robot path overlaid on the video feed.

In some embodiments, the three-dimensional rendition of the sequence of coordinates forming the robot path may be overlaid on the video feed with respect to a floor detected in the video feed.

In some embodiments, the tag information comprises information regarding one of: an availability of a wireless communication signal, a speed the remote telepresence robot should travel, a location of a point of interest, a location of a person, a location of a docking station, a location of a rest area, a location of a glass wall, a location of a ramp, a location of an object, an optimal route to navigate a tight area, an optimal rout to navigate a congested area, and an action a remote telepresence robot should execute.

In some embodiments, the tag information may relate to a position, a path, and/or a volume, and the control system may be configured to execute an action relative to the position, the path, and/or the volume.

In some embodiments, the instructions executable by the processor are further configured to cause the processor to receive coordinates on the plan view map of an obstacle detected by a sensor system of the remote telepresence robot.

In some embodiments, the plan view map and the plurality of tags are stored remotely.

In some embodiments, the plan view map and the plurality of tags are stored within the remote telepresence robot.

In some embodiments, the instructions executable by the processor are further configured to cause the processor to determine a distortion (e.g., a coordinate transformation between a two-dimensional coordinate system and a three-dimensional coordinate system) between the plan view map and the video feed received from the imaging system of the remote telepresence robot; and generate a hybrid map view comprising a blended view of the plan view map and the video feed from the imaging system of the remote telepresence robot.

In some embodiments, the hybrid map view comprises a three-dimensional representation of the plan view map overlaid on the video feed.

In some embodiments, the telepresence robot system local terminal further comprises at least one user input device and the instructions executable by the processor are further configured to cause the processor to receive a request via the at least one input device for a rendered look ahead for a virtual location of the remote telepresence robot on the plan view map; determine a distortion (e.g., a coordinate transformation between a two-dimensional coordinate system and a three-dimensional coordinate system) between the plan view map and the video feed received from the imaging system of the remote telepresence robot; and generate a virtual three-dimensional video feed based on a virtual location of the remote telepresence robot; and display the virtual three-dimensional video feed based on the virtual location of the remote telepresence robot.

In some embodiments, the tag information of the at least one tag comprises a set of coordinates with respect to the plan view map defining a protected region, and the tag annotation of the at least one tag may be configured to indicate the presence of a protected region.

In some embodiments, the instructions executable by the processor are further configured to cause the processor to receive a request to create a new tag; associate tag coordinates describing a relative location of the new tag and tag information, which may include a tag annotation with the new tag; and display a rendition of the tag annotation of the new tag on at least one of the plan view map and the video feed using the tag coordinates.

In some embodiments, the request to create the new tag may be generated by the remote telepresence robot.

In some embodiments, the request to create the new tag may be automatically generated based on a detected object in the video feed.

In some embodiments, the new tag may be a temporary tag configured to expire once the detected object is no longer present in the video feed.

In some embodiments, the object may be a person and the tag information of the new tag comprises identification information associated with the person.

In some embodiments, the object may be a person and the tag information of the new tag comprises potential actions the remote telepresence robot can execute with respect to the person.

In some embodiments, the request to create the new tag may be generated by a user input device in communication with the telepresence robot system local terminal.

In some embodiments, the request to create the new tag is made with respect to the video feed.

In some embodiments, the request to create the new tag is made with respect to the plan view map.

In some embodiments, the request to create a new tag is made with respect to the current position of the remote telepresence robot.

In some embodiments, the tag information comprises information regarding one of: an availability of a wireless communication signal, a speed the remote telepresence robot should travel, a location of a point of interest, a location of a person, a location of a docking station, a location of a rest area, a location of a glass wall, a location of a ramp, a location of an object, an optimal route to navigate a tight area, an optimal rout to navigate a congested area, and an action a remote telepresence robot should execute.

In other embodiments, a telepresence robot may communicate with a remote terminal. The telepresence robot may include a drive system configured to move the telepresence robot according to drive instructions; a control system in communication with the drive system, the control system configured to generate drive instructions to cause the drive system to move the telepresence robot; an imaging system in communication with the control system; a mapping module in communication with the control system, the mapping module configured to access a map data source, the map data source comprising a plan view map representative of robot-navigable areas of a robot operating surface; and a plurality of tags, each tag being a data structure comprising tag coordinates describing the relative location of the tag and tag information, which may include a tag annotation; a positioning system in communication with the control system configured to provide a current position with respect to the plan view map; a tag identification system configured to identify at least one tag relevant to a navigation path of the telepresence robot; and a communication system configured to facilitate communication between the control system and a remote terminal, and the control system may be configured to execute an action based on an identified tag whose tag information comprises a telepresence robot action modifier.

In some embodiments, the tagging information for the identified tag comprises instructions regarding one of a time and a location on the plan view map that the control system should execute the action.

In some embodiments, the control system may be configured to transmit a video feed from the imaging system to the remote terminal via the communication system and the control system may be configured to receive an indication of a desired destination on the plan view map from the remote terminal via the communication system.

In some embodiments, the telepresence robot may further comprise: a plurality of sensors configured to identify obstacles in the vicinity of the telepresence robot and an obstacle avoidance system in communication with the plurality of sensors and in communication with the control system, where the control system may be further configured to generate additional drive instructions to avoid obstacles in the vicinity of the telepresence robot.

In some embodiments, the plurality of sensors comprises at least one of a proximity sensor, a contact sensor, an odometry sensor, and a three-dimensional image sensor.

In some embodiments, the plurality of sensors may comprise a three-dimensional image sensor that forms a point cloud, including a three-dimensional occupancy of obstacles, and the drive instructions may be configured to avoid the three-dimensional occupancy of the obstacles.

In some embodiments, the telepresence robot may further comprise: a map generation system in communication with the control system, the map generation system configured to autonomously create the plan view map of the robot operating surface, where the control system generates drive instructions to cause the telepresence robot to move throughout the robot operating surface and obtain a plurality of measurements, and the map generation system uses the plurality of measurements to generate the plan view map.

In some embodiments, the telepresence robot may further comprise a navigation system configured to generate a navigation path comprising a sequence of coordinates from the current position on the plan view map to the desired destination on the plan view map.

In some embodiments, the telepresence robot may transmit coordinates relative to the plan view map of a detected obstacle to the remote terminal via the communication system.

In some embodiments, the sequence of coordinates forming the navigation path may be based at least in part on tagging information associated with the identified tag.

In some embodiments, the navigation system is configured to generate the navigation path by selecting a navigation path from a plurality of potential navigation paths, and the tags relevant to the navigation path of the telepresence robot are associated with the plurality of potential navigation paths, and the navigation system is configured to select the navigation path based at least in part on the identified relevant tags.

In some embodiments, the sequence of coordinates forming the navigation path is transmitted via the communication system to the remote terminal.

In some embodiments, the telepresence robot may be configured to create a new tag using the sequence of coordinates forming the navigation path, such that the new tag comprises the sequence of coordinates, tagging information related to the navigation path, and a tag annotation related to the navigation path.

In some embodiments, the tag information of each of the plurality of tags comprises information regarding one of: an availability of a wireless communication signal, a speed the remote telepresence robot should travel, a location of a point of interest, a location of a person, a location of a docking station, a location of a rest area, a location of a glass wall, a location of a ramp, a location of an object, an optimal route to navigate a tight area, an optimal rout to navigate a congested area, and an action a remote telepresence robot should execute.

In some embodiments, the control system may be further configured to receive a navigation path from the current position on the plan view map to the desired destination on the plan view map and the control system may be further configured to generate drive instructions to cause the drive system to move the telepresence robot to the desired destination based on the navigation path.

In some embodiments, the communication system may be configured to detect a disruption in communication between the telepresence robot and a remote terminal, wherein the control system may be further configured to continue to generate drive instructions to cause the telepresence robot to autonomously move to the desired destination during the disruption in communication.

In some embodiments, the map data source may be stored remotely, such that the mapping module may be configured to access the map data source via the communication system.

In some embodiments, the map data source may be stored within the telepresence robot, such that the mapping module may be configured to access an internal map data source.

In some embodiments, the internal map data source may be synced with a remotely stored map data source.

In some embodiments, the positioning system may be further configured to provide a robot pose relative to the plan view map.

In some embodiments, the telepresence robot may be configured to create a new tag by: associating tag coordinates describing the relative location of the new tag with respect to one of the plan view map and a video feed generated by the imaging system; associating tag information with the new tag; and associating a tag annotation with the new tag.

In some embodiments, the new tag may be created in response to the telepresence robot detecting an object in the video feed.

In some embodiments, the object may be a person and the tag information of the new tag comprises identification information associated with the person.

In some embodiments, the object may be a person and the tag information of the new tag comprises potential actions the remote telepresence robot can execute with respect to the person.

In some embodiments, the tag information comprises information regarding one of: an availability of a wireless communication signal, a speed the remote telepresence robot should travel, a location of a point of interest, a location of a person, a location of a docking station, a location of a rest area, a location of a glass wall, a location of a ramp, a location of an object, an optimal route to navigate a tight area, an optimal rout to navigate a congested area, and an action a remote telepresence robot should execute.

In some embodiments, the telepresence robot system may further comprise: an RFID reader in communication with the positioning system, where the positioning system associates a plurality of RFID chips with a corresponding plurality of coordinates on the plan view map, and the positioning system may be configured to determine the current position of the telepresence robot based at least in part on the location of one or more RFID chips within range of the RFID reader.

Various methods of control may be employed in the present systems and methods. For example, a telepresence robot system local terminal may comprise: an electronic display; a processor in communication with the electronic display interface; a memory in communication with the processor, the memory comprising instructions executable by the processor configured to cause the processor to: retrieve at least a portion of a plan view map representative of robot-navigable areas of a robot operating surface; receive a video feed from an imaging system of the remote telepresence robot at a first perspective; receive a current position from a positioning system of the remote telepresence robot with respect to a plan view map; display the video feed from the imaging system of the remote telepresence robot; display the plan view map with an indication of the current position of the telepresence robot on the plan view map; transmit a command to the remote telepresence robot; and a user input device in communication with the processor, the user input device configured to allow a user to select a movement for a remote telepresence robot, the selection of the movement comprising selecting a destination of the remote telepresence robot with respect to the video feed; with respect to the plan view map; and by incrementally advancing the remote telepresence robot in one of at least four possible directions relative to the current position of the remote telepresence robot.

In some embodiments, the selection of the movement comprises selecting an alternative perspective of the video feed by selecting a point within the video feed. This mode would likely be used for intermediate distances to get to locations within view on the video feed.

In some embodiments, selection of the movement comprises selecting an alternative perspective of the video feed by selecting a point on the plan view map. This mode would likely be used for farther distances (e.g., down hallways, between rooms, etc.) to locations not within view on the video feed. In some embodiments, selection of the movement comprises using a joystick or meta joystick in manual control. This mode would likely be used for micro/finer adjustments, e.g., within a room in close proximity to humans/patients.

In some embodiments, the selection of the movement comprises selecting an alternative perspective of the video feed by incrementally panning or tilting the imaging system while the remote telepresence robot remains in the current position.

In some embodiments, wherein the selection of the movement may relate to rotating one of a lower portion of the remote telepresence robot and an upper portion of the remote telepresence robot.

In some embodiments, there will be a way to switch between modes, e.g. multi-modal user interface wherein one can select to control either head/imaging system movement or movement of the base/lower portion of the remote presence robot.

In some embodiments when control of head/imaging system movement is selected there may be options to select either position-based box-zoom head motion via mouse or velocity-based head motion via mouse.

In some embodiments when control of base/lower portion of the remote presence robot is selected there may be options to select from one of the following: (1) click-on-map, i.e. top down map view and click on target destination or select from destination list; (2) click-on-video, i.e. position-based control that enables click on location in the video and robot drives there; (3) joystick or meta joystick, e.g., mouse velocity-based control or arrows specifying forward, left, right, etc.

In some embodiments the functionality/information needed to be accessed by user at all times while robot base is moving includes: (1) remote view, i.e., where the robot is headed (view should be large enough to provide meaningful visual information for user to operate safely); (2) for supervisory control modes, potential need for override capability to cancel/abort operation as needed.

In some embodiments, the instructions executable by the processor are further configured to cause the processor to receive a selection of a destination of the remote robot from the user input device; determine a sequence of coordinates relative to the plan view map to create a navigation path between the current position of the remote telepresence robot and the selected destination of the remote telepresence robot; and transmit a command to the remote telepresence robot comprising the sequence of coordinates forming the navigation path.

In some embodiments, the instructions executable by the processor are further configured to cause the processor to display the sequence of coordinates forming the navigation path overlaid on the plan view map.

In some embodiments, the instructions executable by the processor are further configured to cause the processor to: determine a distortion between the plan view map and the video feed received from the imaging system of the remote telepresence robot (e.g., a coordinate transformation between a two-dimensional coordinate system and a three-dimensional coordinate system); apply the distortion to the sequence of coordinates forming the navigation path to determine corresponding video coordinates and perspective data describing the location and perspective of the sequence of coordinates relative to the video feed; and display a three-dimensional rendition of the sequence of coordinates forming the navigation path overlaid on the video feed.

In some embodiments, the three-dimensional rendition of the sequence of coordinates forming the navigation path may be overlaid on the video feed with respect to a floor detected in the video feed.

In some embodiments, the instructions executable by the processor are further configured to cause the processor to receive a selection of a destination of the remote robot from the user input device; transmit destination coordinates relative to the plan view map to the remote telepresence robot, the destination coordinates corresponding to the selected destination; receive a sequence of coordinates relative to the plan view map from a navigation system of the remote telepresence robot, the sequence of coordinates forming a navigation path between the current position of the remote telepresence robot and the desired destination of the remote telepresence robot; and display the sequence of coordinates forming the navigation path overlaid on the plan view map.

In some embodiments, the instructions executable by the processor are further configured to cause the processor to determine a distortion between the plan view map and the video feed received from the imaging system of the remote telepresence robot (e.g., a coordinate transformation between a two-dimensional coordinate system and a three-dimensional coordinate system); apply the distortion to the sequence of coordinates forming the navigation path to determine corresponding video coordinates and perspective data describing the location and perspective of the sequence of coordinates relative to the video feed; and display a three-dimensional rendition of the sequence of coordinates forming the navigation path overlaid on the video feed.

In some embodiments, the three-dimensional rendition of the sequence of coordinates forming the navigation path may be overlaid on the video feed with respect to a floor detected in the video feed.

In some embodiments, the instructions executable by the processor are further configured to cause the processor to receive coordinates on the plan view map of an obstacle detected by a sensor system of the remote telepresence robot.

In some embodiments, the plan view map is stored remotely.

In some embodiments, the plan view map is stored within the remote telepresence robot.

In some embodiments, the instructions executable by the processor are further configured to cause the processor to determine a distortion between the plan view map and the video feed received from the imaging system of the remote telepresence robot (e.g., a coordinate transformation between a two-dimensional coordinate system and a three-dimensional coordinate system); and generate a hybrid map view comprising a blended view of the plan view map and the video feed from the imaging system of the remote telepresence robot.

In some embodiments, the hybrid map view comprises a three-dimensional representation of the plan view map overlaid on the video feed.

In some embodiments, the instructions executable by the processor are further configured to cause the processor to receive a request via the input device for a rendered look-ahead for a virtual location of the remote telepresence robot on the plan view map determine a distortion between the plan view map and the video feed received from the imaging system of the remote telepresence robot (e.g., a coordinate transformation between a two-dimensional coordinate system and a three-dimensional coordinate system); and generate a virtual three-dimensional video feed based on a virtual location of the remote telepresence robot; and display the virtual three-dimensional video feed based on the virtual location of the remote telepresence robot.

In some embodiments, a robot may be configured to unwind and/or to control an upper portion and a lower portion independently in order to appear human-like. For example, a telepresence robot may comprise: an upper portion; a lower portion rotatably connected to the upper portion; a drive system configured to move the telepresence robot according to drive instructions; a control system in communication with the drive system, the control system configured to generate drive instructions to cause the drive system to move the telepresence robot; a rotation system configured to rotate the robot from a first heading to a second heading by rotating the upper portion and the lower portion independently.

In some embodiments, the rotation system may be configured to rotate the robot toward a second heading by rotating the upper portion of the robot toward the second heading; detecting that the upper portion of the robot has reached a panning limit of the upper portion of the robot relative to the lower portion of the robot; begin rotating the lower portion of the robot toward the second heading at the panning limit of the upper portion of the robot; detect that the upper portion of the robot has reached the second heading; and continue rotating the lower portion of the robot toward the second heading while simultaneously counter-rotating the upper portion of the robot, such that the upper portion of the robot maintains the second heading.

In some embodiments, the panning limit may be reached when the upper portion cannot physically rotate anymore with respect to the lower portion of the robot.

In some embodiments, the panning limit may be reached when the upper portion is misaligned with respect to the lower portion a predefined number of rotation degrees.

In some embodiments, the panning limit may be a function of the number of degrees the upper portion is misaligned with respect to the lower portion and the length of time the upper portion has been misaligned with respect to the lower portion.

In some embodiments, the rotation system may be configured to rotate the robot toward a second heading by rotating the upper portion of the robot toward the second heading at a first rotational velocity; rotating the lower portion of the robot toward the second heading at a second rotation velocity; detect that the upper portion of the robot has reached the second heading; and continue rotating the lower portion of the robot toward the second heading while simultaneously counter-rotating the upper portion of the robot, such that the upper portion of the robot maintains the second heading.

In some embodiments the telepresence robot may further comprise an imaging system in communication with the control system and a positioning system in communication with the control system configured to provide a current position of the robot relative to a plan view map and a current alignment of the upper portion with respect to the plan view map, where the control system may be configured to transmit a video feed from the imaging system, the current position of the robot, and the current alignment of the upper portion to a remote terminal, such that the remote terminal can determine a distortion between the plan view map and the video feed received from the imaging system of the remote telepresence robot (e.g., a coordinate transformation between a two-dimensional coordinate system and a three-dimensional coordinate system); apply the distortion to a tag having coordinates associated with the plan view map in order determine corresponding video coordinates and perspective data describing the location and perspective of the tag relative to the video feed; and display a three-dimensional rendition of the tag overlaid on the video feed using the video coordinates.

The above described embodiments are described from the perspective of a robot and/or a local terminal. It should be apparent to one of skill in the art that the embodiments described above could be implemented as systems, adapted as methods performed by a system, or embodied in a computer-readable medium that could be executed by a system. For example, a method for changing a heading of a robot may comprise transmitting a heading to a control system of a robot, the control system of the robot in communication with a drive system configured to move the robot according to drive instructions and rotating an upper portion of the robot toward the heading independently from the lower portion of the robot.

In some embodiments, a method for controlling a remote telepresence robot may comprise retrieving at least a portion of a plan view map representative of robot-navigable areas of a robot operating surface; retrieving at least one of a plurality of tags, each of the plurality of tags comprising tag coordinates describing the relative location of the tag and tag information; receiving a video feed from an imaging system of a remote telepresence robot; receiving positioning information associated with a current position of the remote telepresence robot; displaying, via an electronic display, the video feed from the imaging system of the remote telepresence robot; displaying, via the electronic display, a rendition of the tag information of the at least one tag on the video feed using the tag coordinates; and transmitting a command to the remote telepresence robot. A method for controlling a telepresence robot, comprising retrieving at least a portion of a plan view map; retrieving at least one of a plurality of tags, each tag being a data structure comprising tag coordinates describing the relative location of the tag and tag information; determining a current position relative to the plan view map; identifying at least one tag of the plurality of tags relevant to a navigation path of the telepresence robot; executing an action based on the identified tag whose tag information comprises a telepresence action modifier.

In some embodiments, a method for controlling a telepresence robot may comprise retrieving at least a portion of a plan view map representative of robot-navigable areas of a robot operating surface; receiving a video feed from an imaging system of the remote telepresence robot at a first perspective; receiving positioning data associated with a current position of the remote telepresence robot; displaying the video feed from the imaging system of the remote telepresence robot; and transmitting a command to the remote telepresence robot; and receiving a plurality of movement selections from a user input device movement, the movement selections made (1) with respect to the video feed; (2) with respect to the plan view map; and/or (3) by incrementally advancing the remote telepresence robot in a direction relative to the current position of the remote telepresence robot.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 17 is a schematic view of an example user interface that includes an augmented overlay corresponding to a telepresence robot.

Like reference symbols in the various drawings indicate like elements.

DETAILED DESCRIPTION

Figure 1:
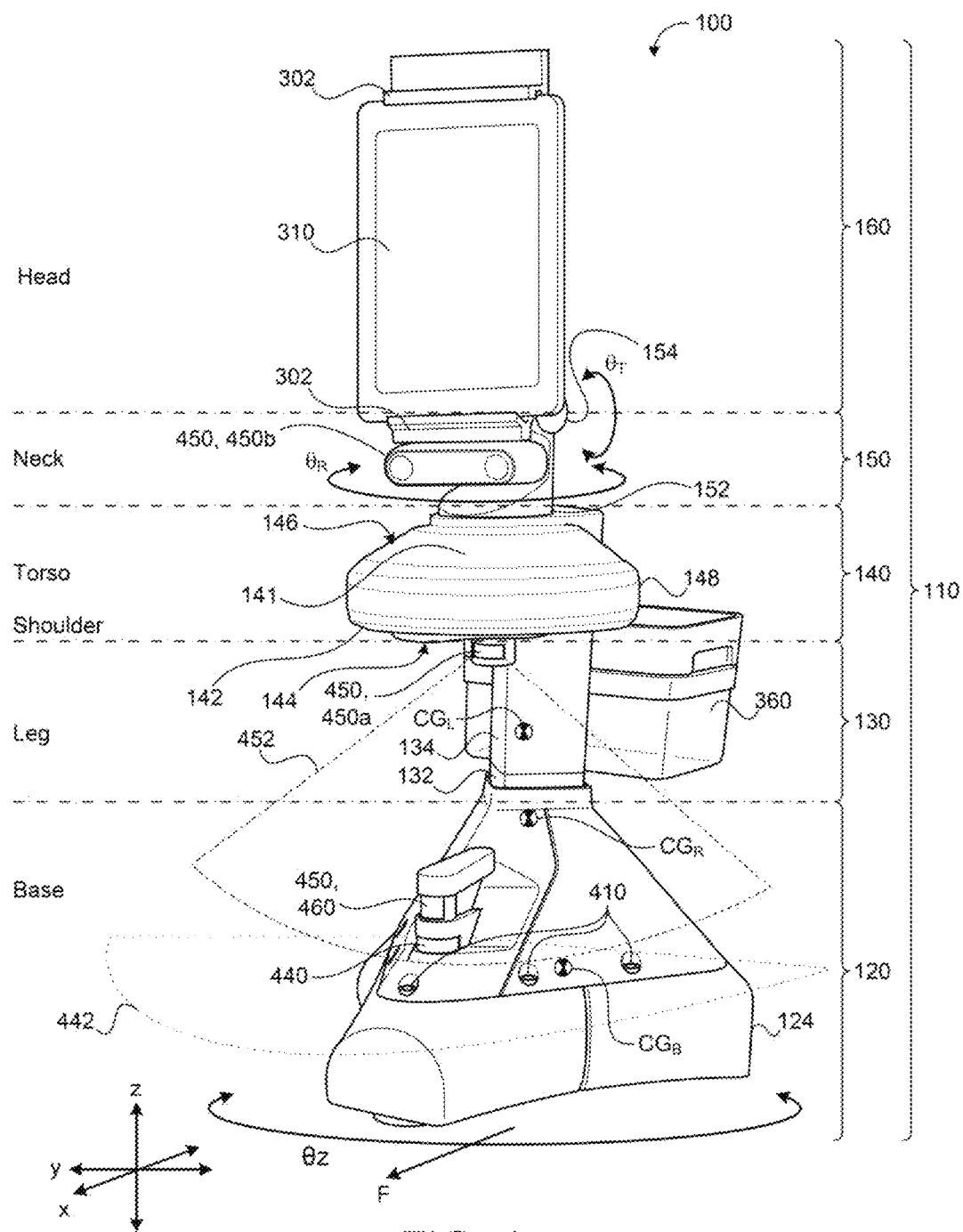
FIG. 1 is a perspective view of an example telepresence robot.

Autonomous driven, self-navigating robots, such as autonomous vehicles and telepresence robots, manage encounters and interactions with obstacles and other points of interest (POI) through their autonomous travels. In one embodiment of the present invention, autonomous vehicles travel trafficked routes (e.g. local roads and interstate highways and freeways) using GPS and maps having tags including POI that trigger a robot behavior routine. Such routines guide the self-navigating robot in response to the POI (e.g. turning the vehicle onto an alternate street or highway to circumvent a traffic jam by electing an alternate route during peak traffic hours), thereby efficiently and effectively traveling autonomously from a start point and to a defined end point on a map. Telepresence robots similarly manage encounters and interactions with obstacles and other POI throughout their autonomous travels through areas of frequent or occasional high traffic volumes, such as, for example, the navigable spaces of office buildings and hospitals. Telepresence robots can interact or interface with humans to provide a number of services, such as a physician or healthcare worker providing remote medical consultation, home assistance, commercial assistance, and more. In the example of home assistance, a telepresence robot can assist elderly people with everyday tasks, including, but not limited to, maintaining a medication regime, mobility assistance, communication assistance (e.g., video conferencing, telecommunications, Internet access, etc.), home or site monitoring (inside and/or outside), person monitoring, and/or providing a personal emergency response system (PERS). For commercial assistance, the telepresence robot can provide videoconferencing (e.g., in a hospital setting), a point of sale terminal, an interactive information/marketing terminal, etc.

Referring to FIGS. 1-3B, in some implementations, a telepresence robot 100 includes a robot body 110 (or chassis) that defines a forward drive direction F. The robot 100 also includes a drive system 200 (FIG. 4D), an interfacing module 300, and a sensor system 400, each supported by the robot body 110 and in communication with a controller 500 (FIG. 5) that coordinates operation and movement of the robot 100. A power source 105 (e.g., battery or batteries) can be carried by the robot body 110 and in electrical communication with, and deliver power to, each of these components, as necessary.

The robot body 110, in the examples shown, includes a base 120, at least one leg 130 extending upwardly from the base 120, and a torso 140 supported by the at least one leg 130. The base 120 may support the drive system 200. The robot body (lower portion) 110 also includes a neck 150 supported by the torso 140. The neck 150 supports a head (upper portion) 160, which supports at least a portion of the interfacing module 300. The base 120 includes enough weight (e.g., by supporting the power source 105 (batteries) to maintain a low center of gravity $CG_B$ of the base 120 and a low overall center of gravity $CG_R$ of the robot 100 for maintaining mechanical stability.

Referring to FIGS. 2 and 4A-4C, in some implementations, the base 120 defines a trilaterally symmetric shape (e.g., a triangular shape from the top view). For example, the base 120 may include a base chassis 122 that supports a base body 124 having first, second, and third base body portions 124a, 124b, 124c corresponding to each leg of the trilaterally shaped base 120 (see e.g., FIG. 4A). Each base body portion 124a, 124b, 124c can be movably supported by the base chassis 122 so as to move independently with respect to the base chassis 122 in response to contact with an object. The trilaterally symmetric shape of the base 120 allows bump detection 360° around the robot 100. Each base body portion 124a, 124b, 124c can have an associated contact sensor (e.g., capacitive sensor, read switch, etc.) that detects movement of the corresponding base body portion 124a, 124b, 124c with respect to the base chassis 122.

In some implementations, the drive system 200 provides omni-directional and/or holonomic motion control of the robot 100. As used herein the term "omni-directional" refers to the ability to move in substantially any planar direction, i.e., side-to-side (lateral), forward/back, and rotational. These directions are generally referred to herein as x, y, and Θz, respectively. Furthermore, the term "holonomic" is used in a manner substantially consistent with the literature use of the term and refers to the ability to move in a planar direction with three planar degrees of freedom, i.e., two translations and one rotation. Hence, a holonomic robot has the ability to move in a planar direction at a velocity made up of substantially any proportion of the three planar velocities (lateral, forward/back, and rotational), as well as the ability to change these proportions in a substantially continuous manner.

The robot 100 can operate in human environments (e.g., environments typically designed for bipedal, walking occupants) using wheeled mobility. In some implementations, the drive system 200 includes first, second, and third drive wheels 210a, 210b, 210c equally spaced (i.e., trilaterally symmetric) about the vertical axis Z (e.g., 120 degrees apart); however, other arrangements are possible as well. Referring to FIG. 4D, the drive wheels 210a, 210b, 210c may define a transverse arcuate rolling surface (i.e., a curved profile in a direction transverse or perpendicular to the rolling direction $D_R$), which may aid maneuverability of the holonomic drive system 200. Each drive wheel 210a, 210b, 210c is coupled to a respective drive motor 220a, 220b, 220c that can drive the drive wheel 210a, 210b, 210c in forward and/or reverse directions independently of the other drive motors 220a, 220b, 220c. Each drive motor 220a-c can have a respective encoder, which provides wheel rotation feedback to the controller 500. In some examples, each drive wheel 210a, 210b, 210c is mounted on or near one of the three points of an equilateral triangle and has a drive direction (forward and reverse directions) that is perpendicular to an angle bisector of the respective triangle end. Driving the trilaterally symmetric holonomic base 120 with a forward driving direction F allows the robot 100 to transition into non-forward drive directions for autonomous escape from confinement or clutter and then rotate and/or translate to drive along the forward drive direction F after the escape has been resolved.

Figure 4A:
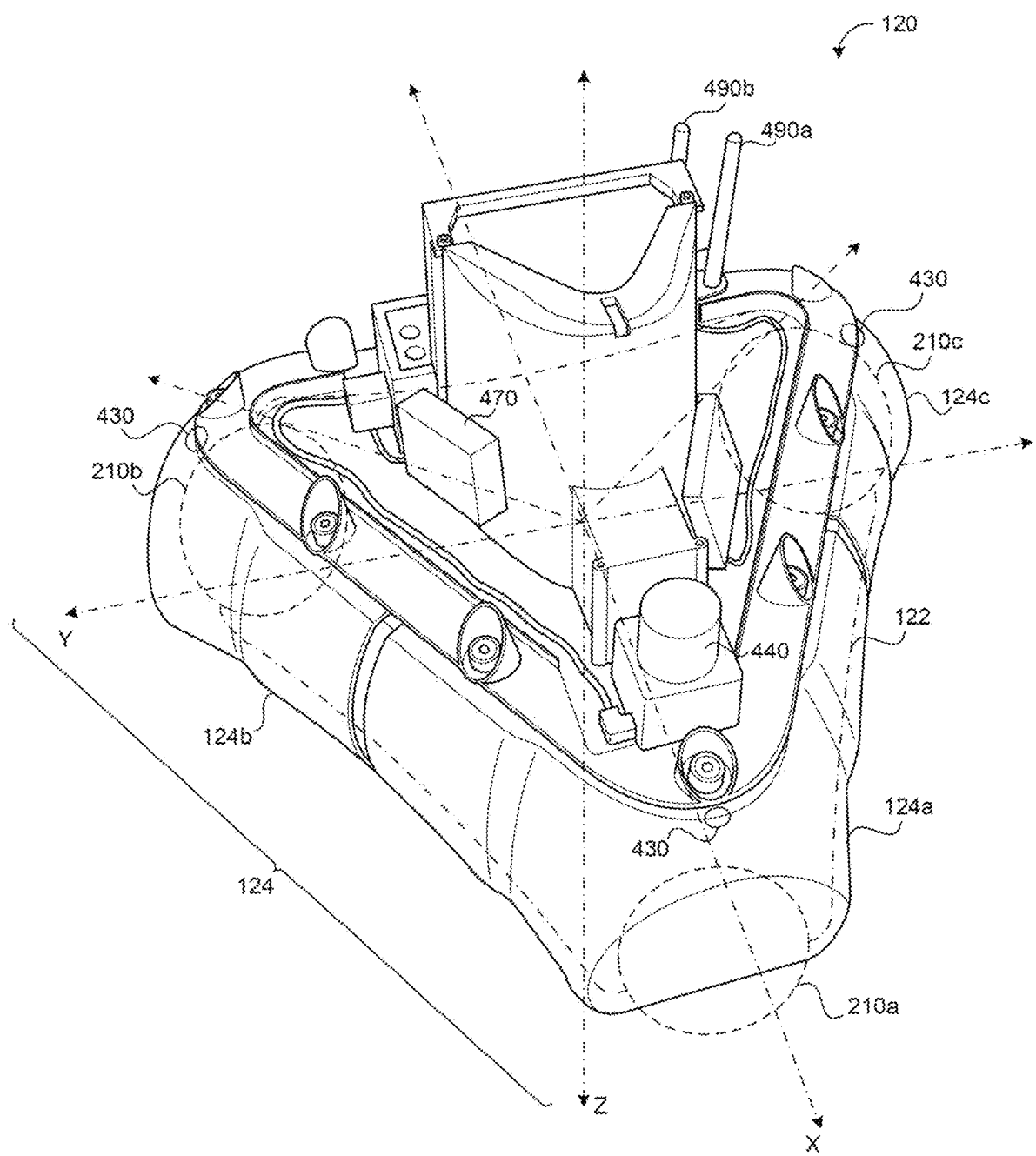
FIG. 4A is a front perspective view of an example base for a mobile human interface robot.
Figure 4B:
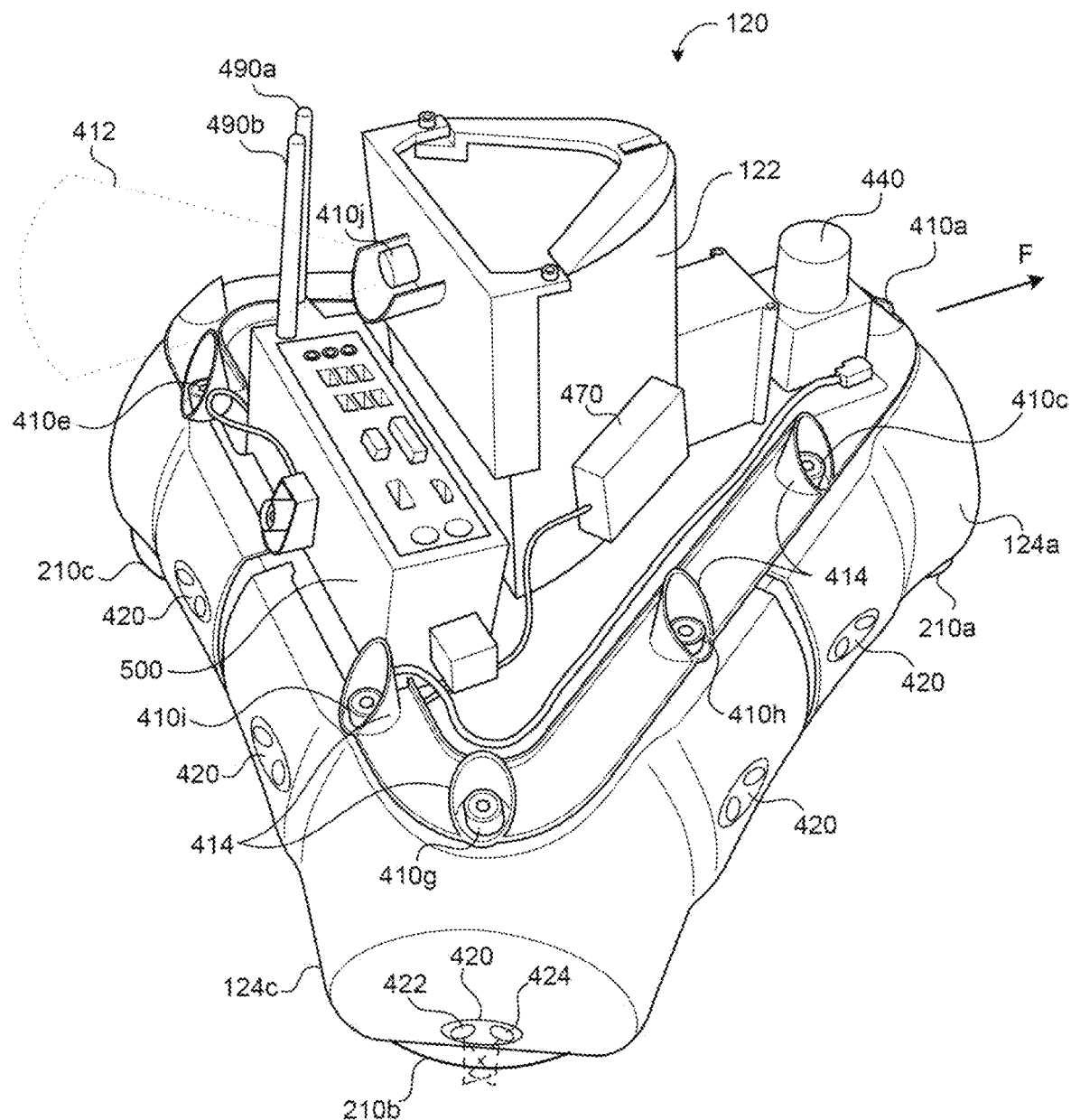
FIG. 4B is a rear perspective view of the base shown in FIG. 4A.
Figure 4C:
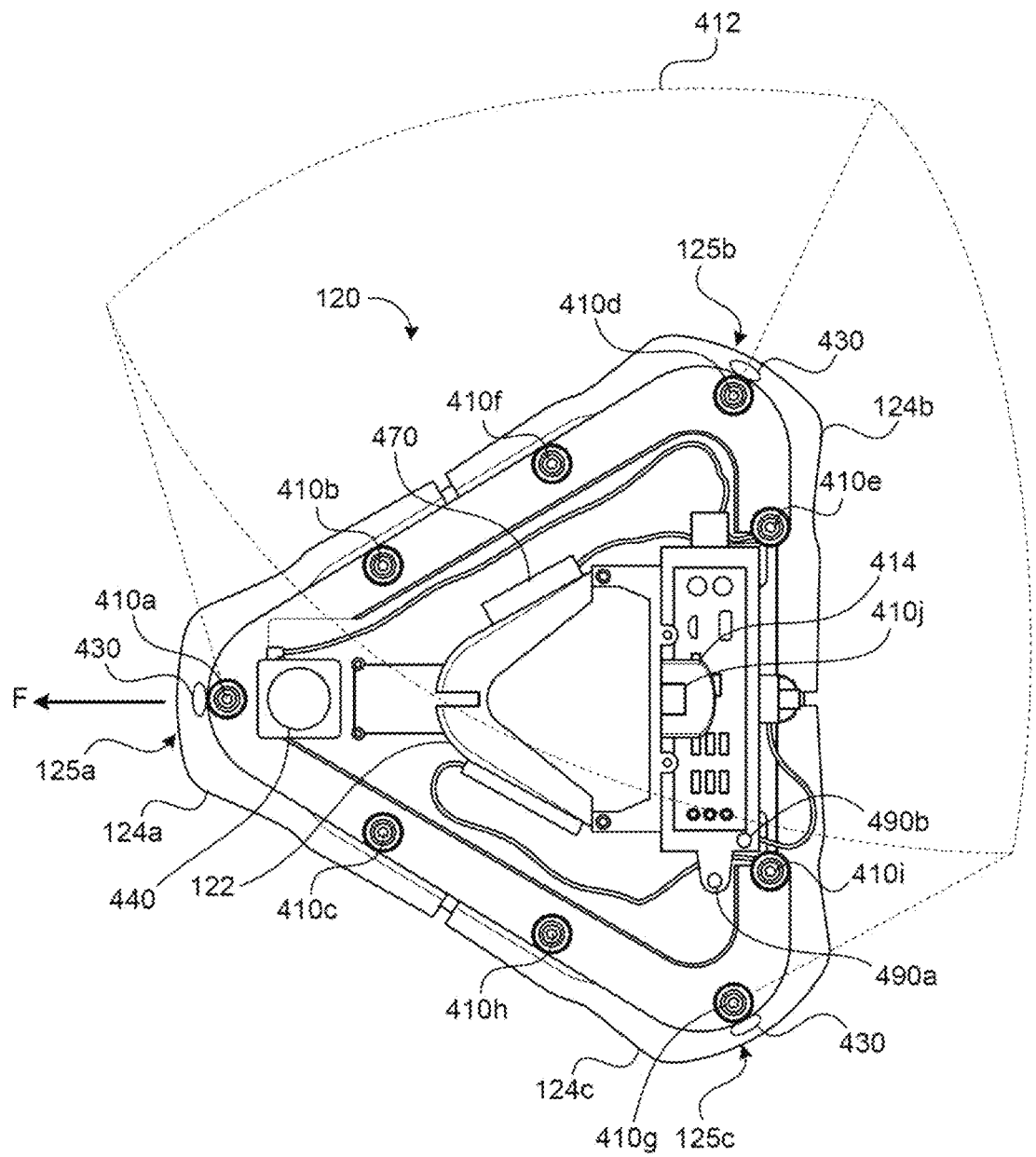
FIG. 4C is a top view of the base shown in FIG. 4A.
Figure 4D:
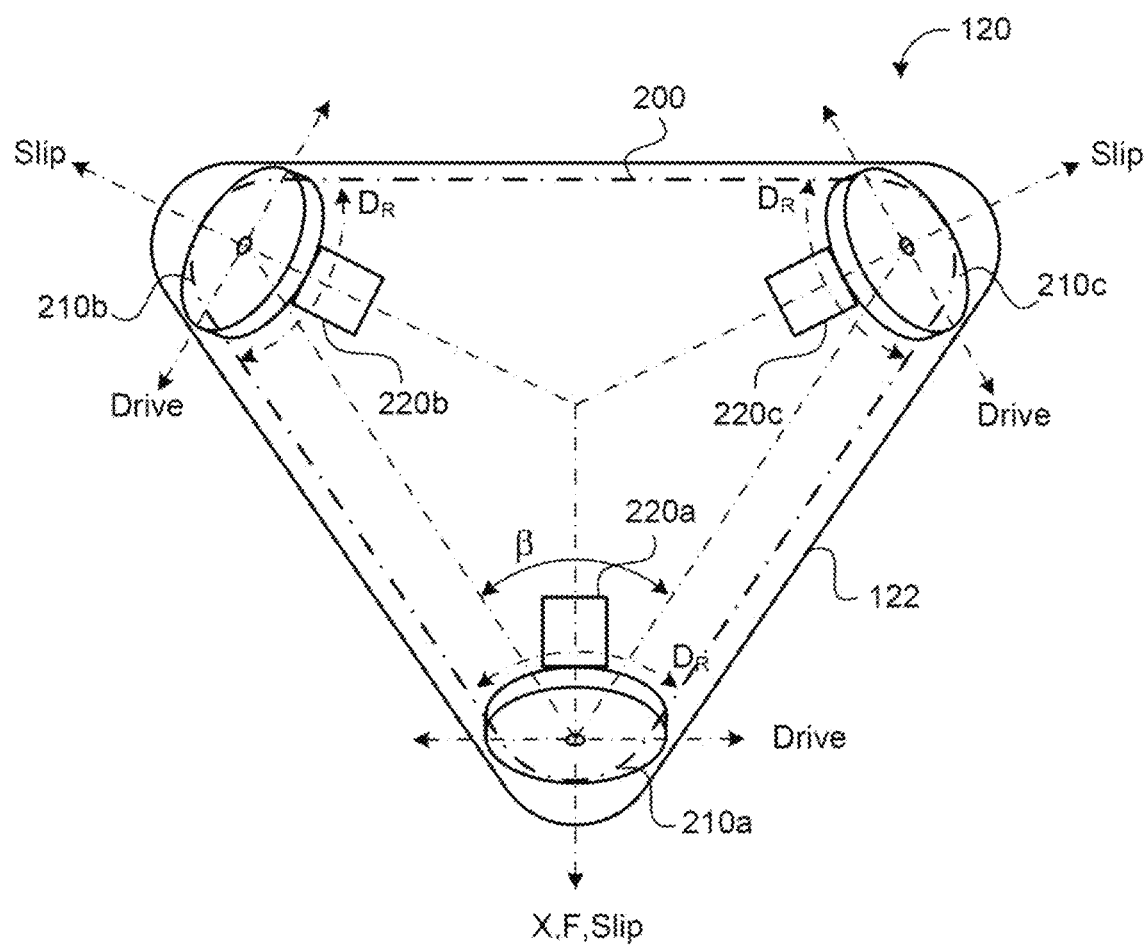
FIG. 4D is a top schematic view of an example base for a telepresence robot.
Figure 4E:
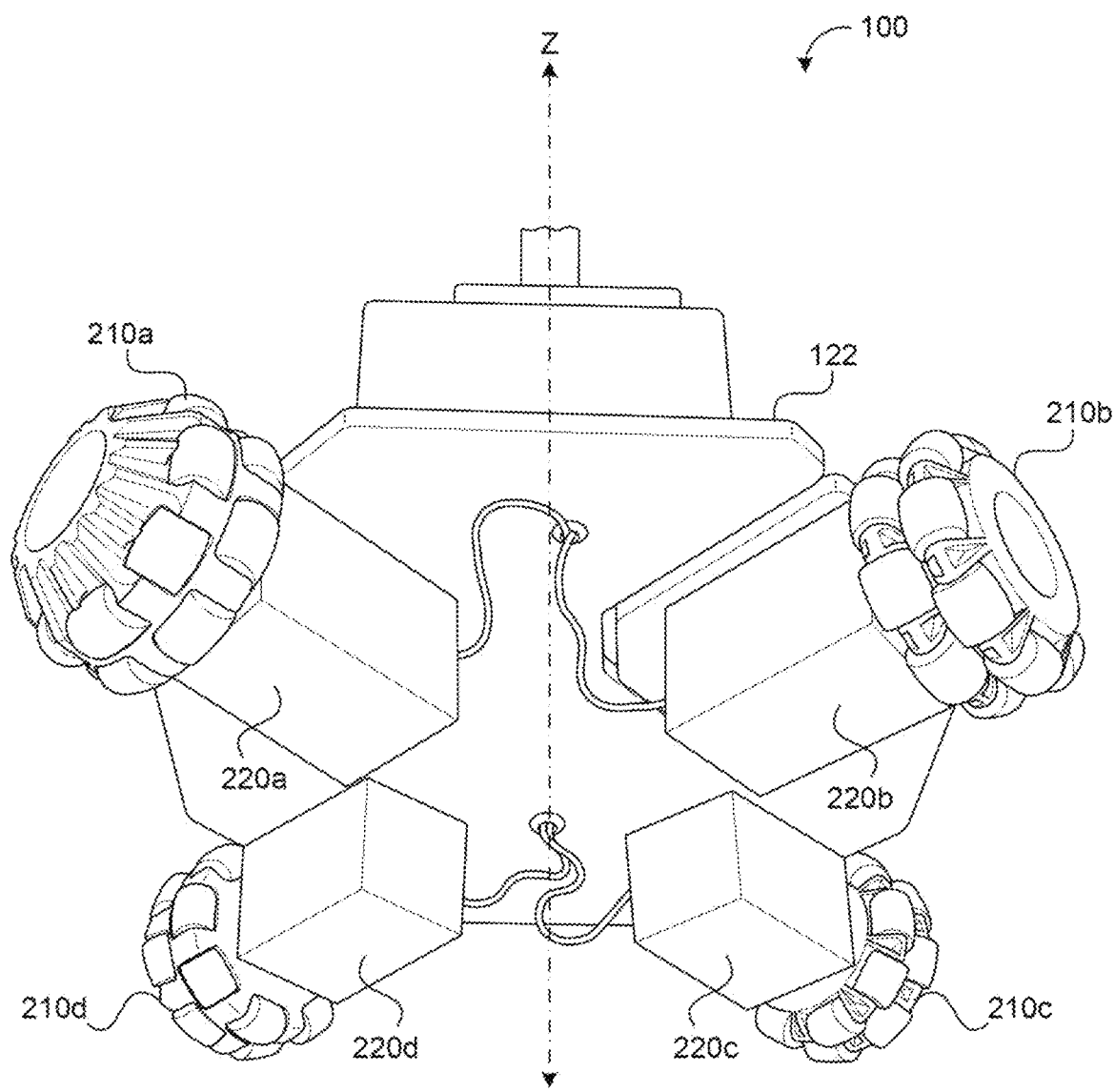
FIG. 4E is a bottom perspective view of an example drive system for a telepresence robot.
Figure 4F:
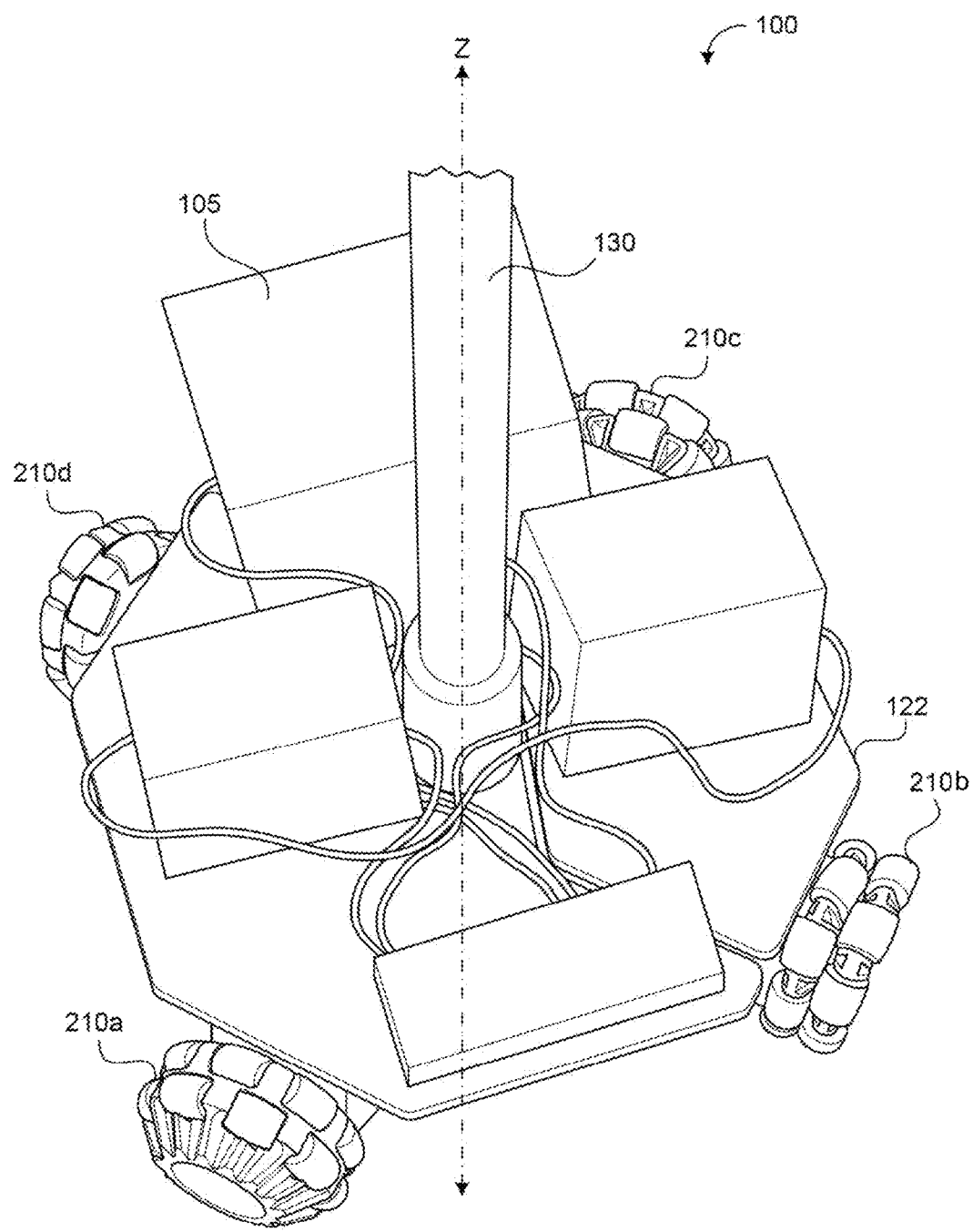
FIG. 4F is a top perspective view of the drive system shown in FIG. 4E.

Referring to FIGS. 4E and 4F, in some implementations, the drive system 200 includes first, second, third, and fourth drive wheels 210a-d arranged in a square or rectangular configuration (e.g., equidistantly from the Z axis) from a top view. The drive system 200 may operate in a holonomic manner, allowing strafing. Each drive wheel 210a-d is coupled to a respective drive motor 220a-d that can drive the drive wheel 210a-d in forward and/or reverse directions independently of the other drive motors 220a-d. Each drive motor 220a-d can have a respective encoder, which provides wheel rotation feedback to the controller 500. A base chassis 122 supports the drive motors 220a-d and the correspondingly coupled drive wheels 210a-d.

Figure 2:
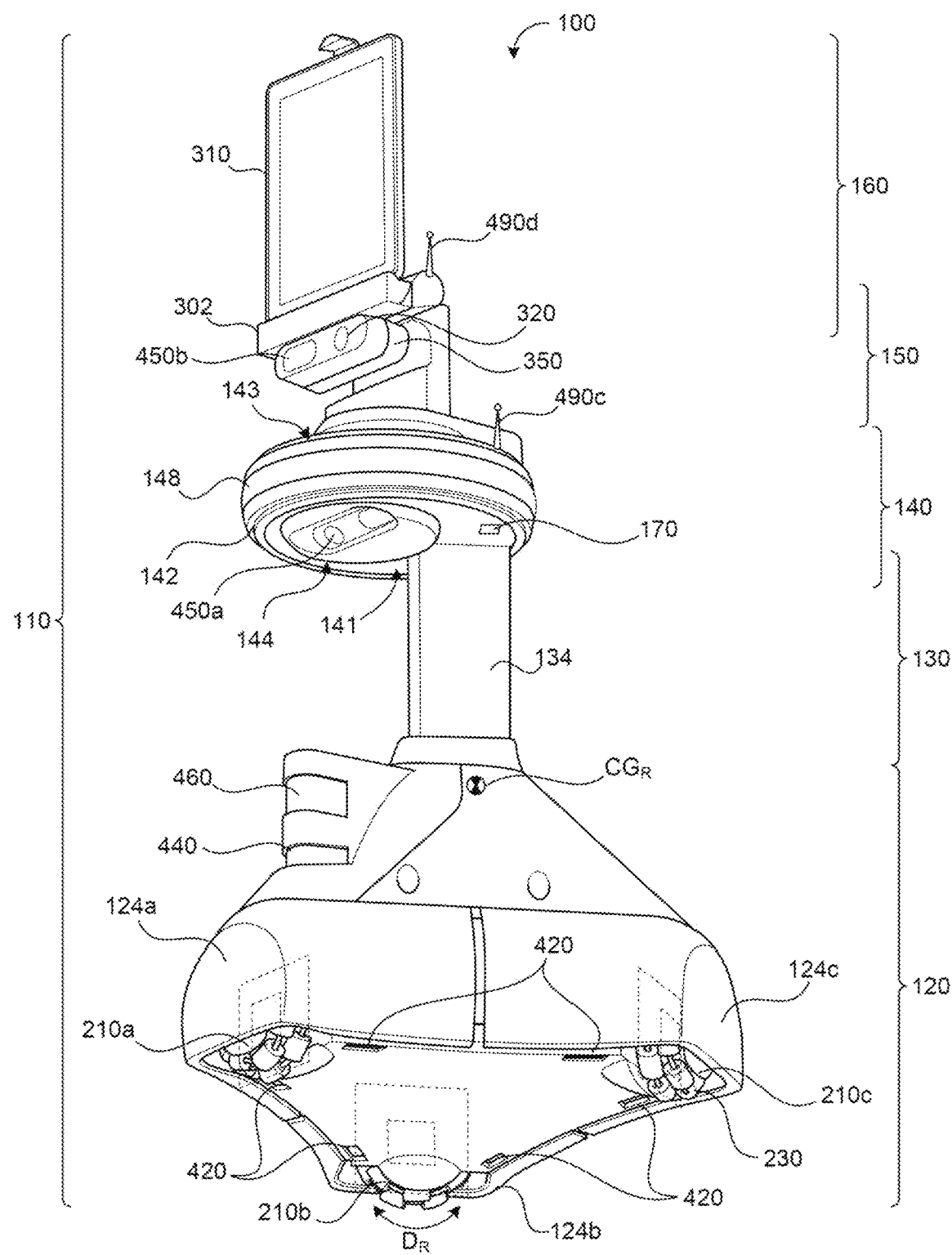
FIG. 2 is an elevated perspective view of an example telepresence robot.
Figure 3A:
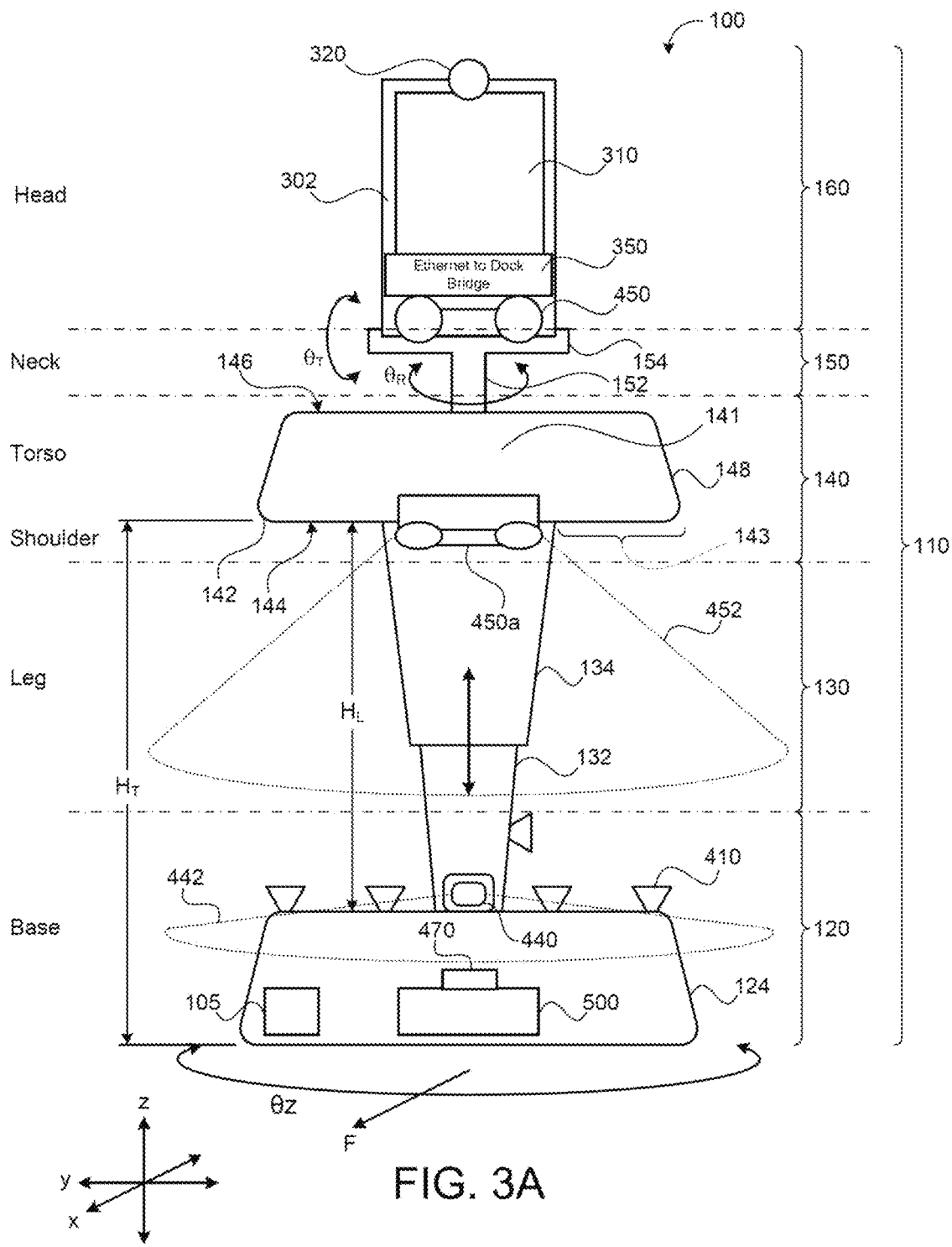
FIGS. 3A-3C are schematic views of example telepresence robots.
Figure 3B:
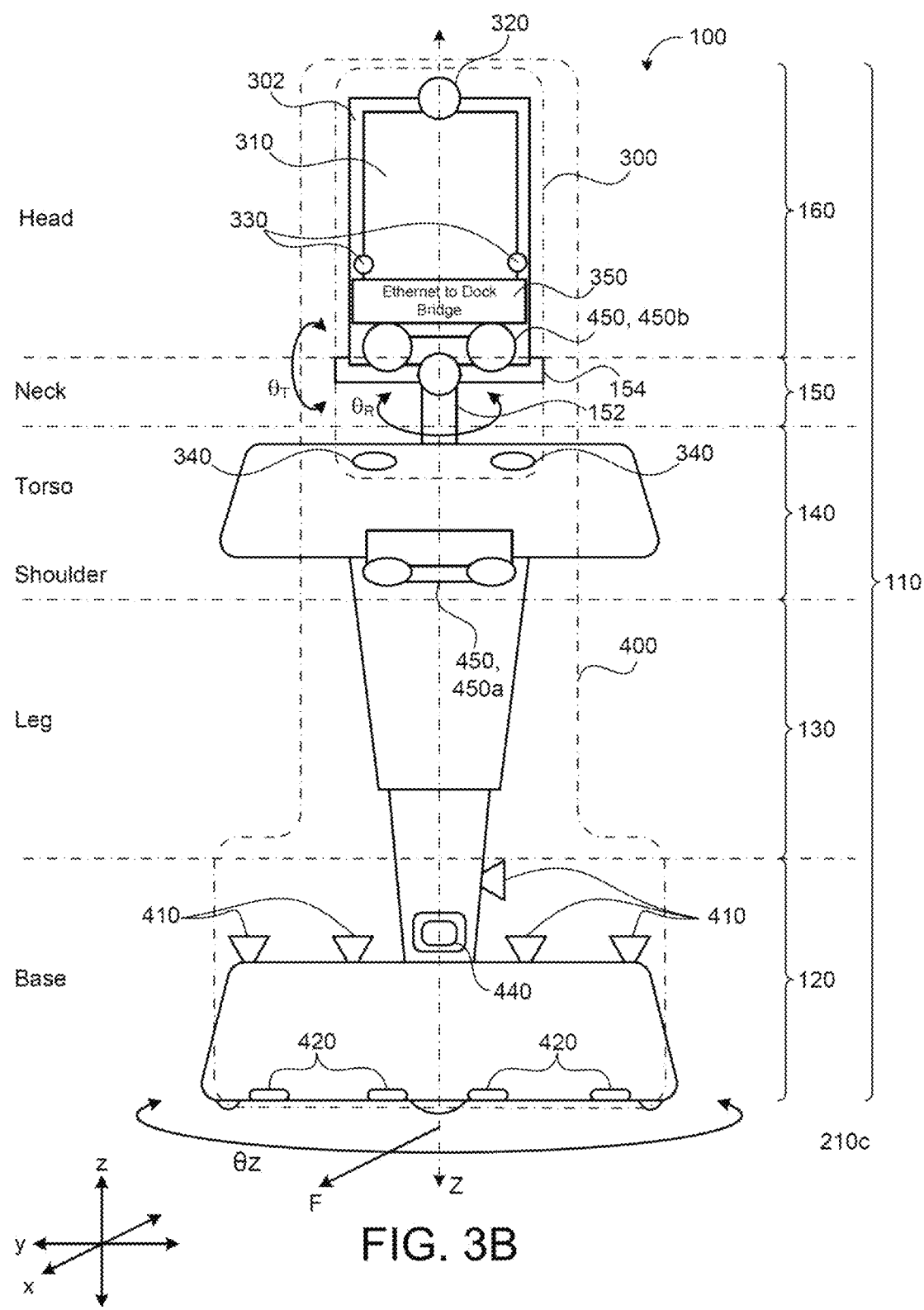
Figure 3C:
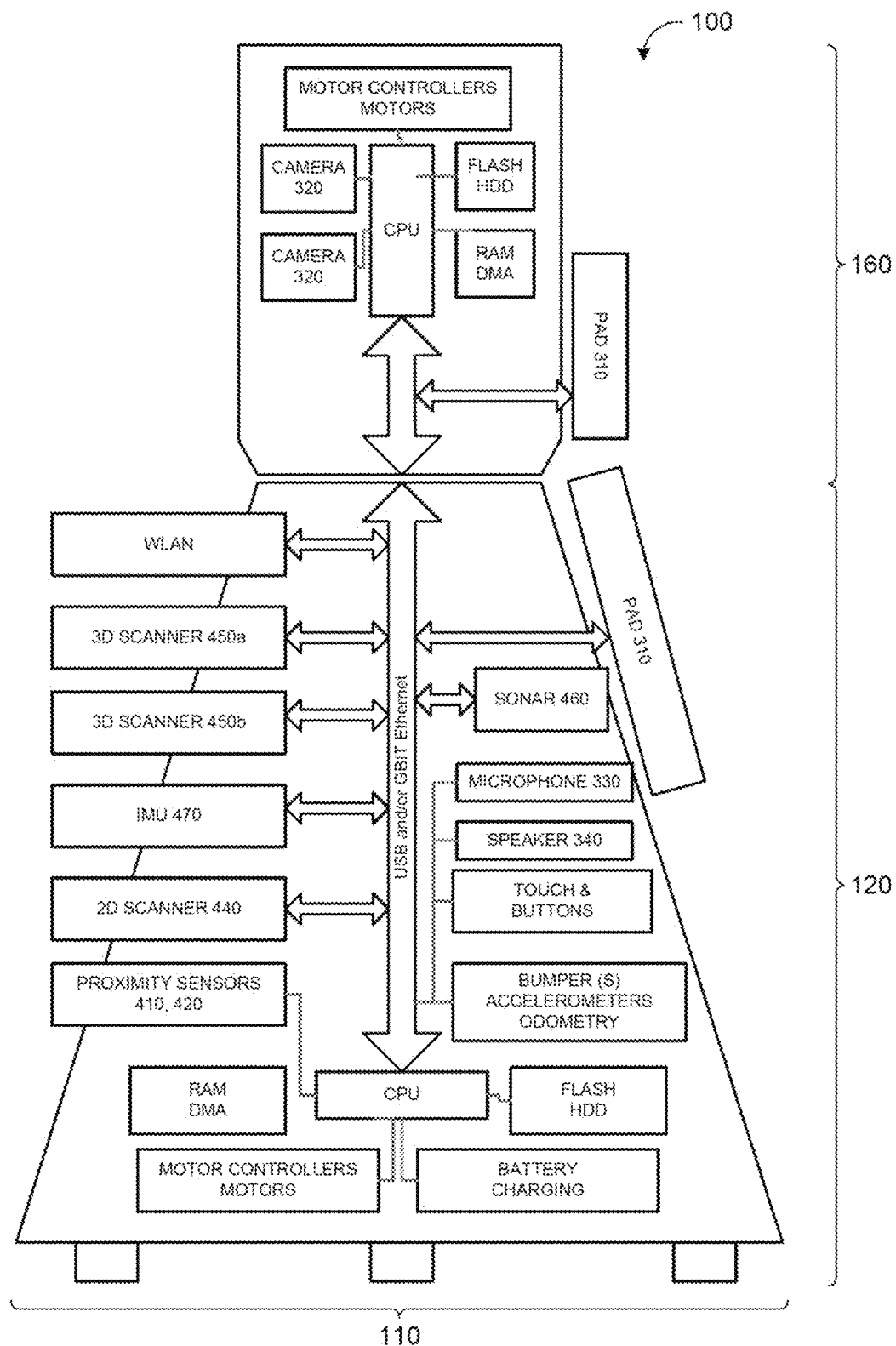

In some examples, as illustrated in FIG. 2, the first drive wheel 210a is arranged as a leading drive wheel along the forward drive direction F with the remaining two drive wheels 210b, 210c trailing behind. In this arrangement, to drive forward, the controller 500 may issue a drive command that causes the second and third drive wheels 210b, 210c to drive in a forward rolling direction at an equal rate while the first drive wheel 210a slips along the forward drive direction F. Moreover, this drive wheel arrangement allows the robot 100 to stop short (e.g., incur a rapid negative acceleration against the forward drive direction F). This is due to the natural dynamic instability of the three-wheeled design. If the forward drive direction F were along an angle bisector between two forward drive wheels, stopping short would create a torque that would force the robot 100 to fall, pivoting over its two "front" wheels. Instead, traveling with one drive wheel 210a forward naturally supports or prevents the robot 100 from toppling over forward, if there is need to come to a quick stop. When accelerating from a stop, however, the controller 500 may take into account a moment of inertia I of the robot 100 from its overall center of gravity $CG_R$.

In some implementations of the drive system 200, each drive wheel 210a, 210b, 210 has a rolling direction $D_R$ radially aligned with a vertical axis Z, which is orthogonal to X and Y axes of the robot 100. The first drive wheel 210a can be arranged as a leading drive wheel along the forward drive direction F with the remaining two drive wheels 210b, 210c trailing behind. In this arrangement, to drive forward, the controller 500 may issue a drive command that causes the first drive wheel 210a to drive in a forward rolling direction and the second and third drive wheels 210b, 210c to drive at an equal rate as the first drive wheel 210a, but in a reverse direction.

In other implementations, the drive system 200 can be arranged to have the first and second drive wheels 210a, 210b positioned such that an angle bisector of an angle between the two drive wheels 210a, 210b is aligned with the forward drive direction F of the robot 100. In this arrangement, to drive forward, the controller 500 may issue a drive command that causes the first and second drive wheels 210a, 210b to drive in a forward rolling direction and an equal rate, while the third drive wheel 210c drives in a reverse direction or remains idle and is dragged behind the first and second drive wheels 210a, 210b. To turn left or right while driving forward, the controller 500 may issue a command that causes the corresponding first or second drive wheel 210a, 210b to drive at a relatively quicker/slower rate. Other drive system arrangements can be used as well. The drive wheels 210a, 210b, 210c may define a cylindrical, circular, elliptical, or polygonal profile.

Referring again to FIGS. 1-3B, the base 120 supports at least one leg 130 extending upward in the Z direction from the base 120. The leg(s) 130 may be configured to have a variable height for raising and lowering the torso 140 with respect to the base 120. In some implementations, each leg 130 includes first and second leg portions 132, 134 that move with respect to each other (e.g., telescopic, linear, and/or angular movement). Rather than having extrusions of successively smaller diameter telescopically moving in and out of each other and out of a relatively larger base extrusion, the second leg portion 134, in the examples shown, moves telescopically over the first leg portion 132, thus allowing other components to be placed along the second leg portion 134 and potentially move with the second leg portion 134 to a relatively close proximity of the base 120. The leg 130 may include an actuator assembly for moving the second leg portion 134 with respect to the first leg portion 132. The actuator assembly 136 may include a motor driver in communication with a lift motor and an encoder, which provides position feedback to the controller.

Generally, telescopic arrangements include successively smaller diameter extrusions telescopically moving up and out of relatively larger extrusions at the base 120 in order to keep a center of gravity $CG_L$ of the entire leg 130 as low as possible. Moreover, stronger and/or larger components can be placed at the bottom to deal with the greater torques experienced at the base 120 when the leg 130 is fully extended. This approach, however, offers two problems. First, when the relatively smaller components are placed at the top of the leg 130, any rain, dust, or other particulate tends to run or fall down the extrusions, infiltrating a space between the extrusions, thus obstructing nesting of the extrusions. This creates a very difficult sealing problem while still trying to maintain full mobility/articulation of the leg 130. Second, it may be desirable to mount payloads or accessories on the robot 100. One common place to mount accessories is at the top of the torso 140. If the second leg portion 134 moves telescopically in and out of the first leg portion, accessories and components could only be mounted above the entire second leg portion 134, if they need to move with the torso 140. Otherwise, any components mounted on the second leg portion 134 would limit the telescopic movement of the leg 130.

By having the second leg portion 134 move telescopically over the first leg portion 132, the second leg portion 134 provides additional payload attachment points that can move vertically with respect to the base 120. This type of arrangement causes water or airborne particulate to run down the torso 140 on the outside of every leg portion 132, 134 (e.g., extrusion) without entering a space between the leg portions 132, 134. This greatly simplifies sealing any joints of the leg 130. Moreover, payload/accessory mounting features of the torso 140 and/or second leg portion 134 are always exposed and available no matter how the leg 130 is extended.

Referring to FIG. 2, the leg 130 supports the torso 140, which may have a shoulder 142 extending over and above the base 120. In the example shown, the torso 140 has a downward facing or bottom surface 144 (e.g., toward the base) forming at least part of the shoulder 142 and an opposite upward facing or top surface 146 (FIG. 3A), with a side surface 148 extending therebetween. The torso 140 may define various shapes or geometries, such as a circular or an elliptical shape having a central portion 141 supported by the leg(s) 130 and a peripheral free portion 143 that extends laterally beyond a lateral extent of the leg(s) 130, thus providing an overhanging portion that defines the downward facing surface 144. In some examples, the torso 140 defines a polygonal or other complex shape that defines a shoulder, which provides an overhanging portion that extends beyond the leg(s) 130 over the base 120.

The robot 100 may include one or more accessory ports 170 (e.g., mechanical and/or electrical interconnect points) for receiving payloads. The accessory ports 170 can be located so that received payloads do not occlude or obstruct sensors of the sensor system 400 (e.g., on the bottom and/or top surfaces 144, 146 of the torso 140, etc.).

An external surface of the torso 140 may be sensitive to contact or touching by a user, so as to receive touch commands from the user. For example, when the user touches the top surface 146 of the torso 140, the robot 100 responds by lowering a height of the torso with respect to the floor (e.g., by decreasing the height of the leg(s) 130 supporting the torso 140). Similarly, when the user touches the bottom surface 144 of the torso 140, the robot 100 responds by raising the torso 140 with respect to the floor (e.g., by increasing the height of the leg(s) 130 supporting the torso 140). Moreover, upon receiving a user touch on forward, rearward, right or left portions of side surface 148 of the torso 140, the robot 100 responds by moving in a corresponding direction of the received touch command (e.g., rearward, forward, left, and right, respectively). The external surface(s) of the torso 140 may include a capacitive sensor in communication with the controller that detects user contact.

Referring again to FIGS. 1-3B, the torso 140 supports the neck 150, which provides panning and tilting of the head 160 with respect to the torso 140. In the examples shown, the neck 150 includes a rotator 152 and a tilter 154. The rotator 152 may provide a range of angular movement $\theta_R$ (e.g., about the Z axis) of between about 90° and about 360°. Other ranges are possible as well. Moreover, in some examples, the rotator 152 includes electrical connectors or contacts that allow continuous 360° rotation of the head 160 with respect to the torso 140 in an unlimited number of rotations while maintaining electrical communication between the head 160 and the remainder of the robot 100. The tilter 154 may include the same or similar electrical connectors or contacts allow rotation of the head 160 with respect to the torso 140 while maintaining electrical communication between the head 160 and the remainder of the robot 100. The rotator 152 may include a rotator motor coupled to or engaging a ring (e.g., a toothed ring rack). The tilter 154 may move the head at an angle $\theta_T$ (e.g., about the Y axis) with respect to the torso 140 independently of the rotator 152. In some examples that tilter 154 includes a tilter motor, which moves the head 160 between an angle $\theta_T$ of ±90° with respect to Z axis. Other ranges are possible as well, such as ±45°, etc. The robot 100 may be configured so that the leg(s) 130, the torso 140, the neck 150, and the head 160 stay within a perimeter of the base 120 for maintaining stable mobility of the robot 100.

The head 160 may be sensitive to contact or touching by a user, so as to receive touch commands from the user. For example, when the user pulls the head 160 forward, the head 160 tilts forward with passive resistance and then holds the position. Moreover, if the user pushes/pulls the head 160 vertically downward, the torso 140 may lower (via a reduction in length of the leg 130) the head 160. The head 160 and/or neck 150 may include strain gauges and/or contact sensors 165 that sense user contact or manipulation.

In some implementations, the head 160 supports one or more portions of the interfacing module 300. The head 160 may include a dock 302 for releasably receiving one or more computing tablets 310, also referred to as a web pad or a tablet PC, each of which may have a touch screen 312. The web pad 310 may be oriented forward, rearward or upward. In some implementations, web pad 310 includes a touch screen, optional I/O (e.g., buttons and/or connectors, such as micro-USB, etc.) a processor, and memory in communication with the processor. An example web pad 310 includes the Apple iPad by Apple, Inc. In some examples, the web pad 310 functions as the controller 500 or assist the controller 500 in controlling the robot 100. The touch screen may detect, monitor, and/or reproduce points of user touching thereon for receiving user inputs and providing a graphical user interface that is touch interactive. In some examples, the web pad 310 includes a touch screen caller that allows the user to find it when it has been removed from the robot 100.

The interfacing module 300 may include a camera 320 disposed on the head 160 (see e.g., FIG. 3A), which can be used to capture video from an elevated vantage point of the head 160 (e.g., for videoconferencing). In the example shown in FIG. 2, the camera 320 is disposed on the neck 150. In some examples, the camera 320 is operated only when the web pad 310 is detached or undocked from the head 160. When the web pad 310 is attached or docked on the head 160 in the dock 302 (and optionally covering the camera 320), the robot 100 may use a camera of the web pad 310 for capturing video. In such instances, the camera 320 may be disposed behind the docked web pad 310 and enter an active state when the web pad 310 is detached or undocked from the head 160 and an inactive state when the web pad 310 is attached or docked on the head 160.

The robot 100 can provide videoconferencing (e.g., at 24 fps or higher) through the interface module 300 (e.g., using a web pad 310, the camera 320, the microphones 330, and/or the speakers 340). The videoconferencing can be multiparty. The robot 100 can provide eye contact between both parties of the videoconferencing by maneuvering the head 160 to face the user. Moreover, the robot 100 can have a gaze angle of <5° (e.g., an angle away from an axis normal to the forward face of the head 160). At least one three-dimensional image sensor 450 and/or the camera 320 on the robot 100 can capture life-size images including body language. The controller 500 can synchronize audio and video (e.g., with a difference of <50 ms). The camera 320 may be movable within at least 1° of freedom separately from the web pad 310. The head 160 may include one or more speakers 340 so as to have sound emanate from the head 160 near the web pad 310 displaying the videoconferencing.

The interfacing module 300 may include a microphone 330 (or micro-phone array) for receiving sound inputs and one or more speakers 340 disposed on the robot body 110 for delivering sound outputs.

Referring to FIGS. 1-3C, to achieve reliable and robust autonomous movement, the sensor system 400 may include several different types of sensors which can be used in conjunction with one another to create a perception of the robot's environment sufficient to allow the robot 100 to make intelligent decisions about actions to take in that environment. The sensor system 400 may include one or more types of sensors supported by the robot body 110, which may include obstacle detection obstacle avoidance (ODOA) sensors, communication sensors, navigation sensors, etc. For example, these sensors may include, but are not limited to, proximity sensors, contact sensors, three-dimensional imaging/depth map sensors, a camera (e.g., visible light and/or infrared camera), sonar, radar, Light Detection And Ranging (LIDAR), which can entail optical remote sensing that measures properties of scattered light to find range and/or other information of a distant target), Laser Detection and Ranging (LADAR), etc. In some implementations, the sensor system 400 includes ranging sonar sensors 410 (e.g., nine about a perimeter of the base 120), proximity cliff detectors 420, contact sensors 430 (FIG. 4A), a laser scanner 440, one or more three-dimensional imaging/depth sensors 450, and an imaging sonar 460.

In some implementations, the sensor system 400 includes a set or an array of proximity sensors 410, 420 in communication with the controller 500 and arranged in one or more zones or portions of the robot 100 (e.g., disposed on or near the base body portion 124a, 124b, 124c of the robot body 110) for detecting any nearby or intruding obstacles. The proximity sensors 410, 420 may be converging infrared (IR) emitter-sensor elements, sonar sensors, ultrasonic sensors, and/or imaging sensors (e.g., 3D depth map image sensors) that provide a signal to the controller 500 when an object is within a given range of the robot 100.

In the example shown in FIGS. 4A-4C, the robot 100 includes an array of sonar-type proximity sensors 410 disposed (e.g., substantially equidistant) around the base 124 of body 120 and arranged with an upward field of view. First, second, and third sonar proximity sensors 410a, 410b, 410c are disposed on or near the first (forward) base body portion 124a, with at least one of the sonar proximity sensors near a radially outermost edge 125a of the first base 124a of body 120. Fourth, fifth, and sixth sonar proximity sensors 410d, 410e, 410f are disposed on or near the second (right) base body portion 124b, with at least one of the sonar proximity sensors near a radially outermost edge 125b of the second base 124b of body 120. Seventh, eighth, and ninth sonar proximity sensors 410g, 410h, 410i are disposed on or near the third (left) base body portion 124c, with at least one of the sonar proximity sensors near a radially outermost edge 125c of the third base 124c of body 120. This configuration provides at least three zones of detection.

In some examples, the set of sonar proximity sensors 410 (e.g., 410a-410i) disposed around the base 124 of body 120 are arranged to point upward (e.g., substantially in the Z direction) and optionally angled outward away from the Z axis, thus creating a detection curtain 412 around the robot 100. Each sonar proximity sensor 410a-410i may have a shroud or emission guide 414 that guides the sonar emission upward or at least not toward the other portions of the robot body 110 (e.g., so as not to detect movement of the robot body 110 with respect to itself). The emission guide 414 may define a shell or half-shell shape. In the example shown, the base 124 of body 120 extends laterally beyond the leg 130, and the sonar proximity sensors 410 (e.g., 410a-410i) are disposed on the base 124 of body 120 (e.g., substantially along a perimeter of the base 124 of body 120) around the leg 130. Moreover, the upward pointing sonar proximity sensors 410 are spaced to create a continuous or substantially continuous sonar detection curtain 412 around the leg 130. The sonar detection curtain 412 can be used to detect obstacles having elevated lateral protruding portions, such as table tops, shelves, etc.

The upward looking sonar proximity sensors 410 provide the ability to see objects that are primarily in the horizontal plane, such as table tops. These objects, due to their aspect ratio, may be missed by other sensors of the sensor system, such as the laser scanner 440 or imaging sensors 450, and as such, can pose a problem to the robot 100. The upward viewing sonar proximity sensors 410 arranged around the perimeter of the base 120 provide a means for seeing or detecting those types of objects/obstacles. Moreover, the sonar proximity sensors 410 can be placed around the widest points of the base perimeter and angled slightly outwards, so as not to be occluded or obstructed by the torso 140 or head 160 of the robot 100, thus not resulting in false positives for sensing portions of the robot 100 itself. In some implementations, the sonar proximity sensors 410 are arranged (upward and outward) to leave a volume about the torso 140 outside of a field of view of the sonar proximity sensors 410 and thus free to receive mounted payloads or accessories, such as the basket 360. The sonar proximity sensors 410 can be recessed into the base body 124 to provide visual concealment and no external features to snag on or hit obstacles.

The sensor system 400 may include one or more sonar proximity sensors 410 (e.g., a rear proximity sensor 410j) directed rearward (e.g., opposite to the forward drive direction F) for detecting obstacles while backing up. The rear sonar proximity sensor 410j may include an emission guide 414 to direct its sonar detection field 412. Moreover, the rear sonar proximity sensor 410j can be used for ranging to determine a distance between the robot 100 and a detected object in the field of view of the rear sonar proximity sensor 410j (e.g., as "back-up alert"). In some examples, the rear sonar proximity sensor 410j is mounted recessed within the base 124 of body 120 so as not to provide any visual or functional irregularity in the housing form.

Referring to FIGS. 2 and 4B, in some implementations, the robot 100 includes cliff proximity sensors 420 arranged near or about the drive wheels 210a, 210b, and 210c, so as to allow cliff detection before the drive wheels 210a, 210b, 210c encounter a cliff (e.g., stairs). For example, a cliff proximity sensor 420 can be located at or near each of the radially outermost edges 125a-c of the base bodies 124a-c and in locations therebetween. In some cases, cliff sensing is implemented using infrared (IR) proximity or actual range sensing, using an infrared emitter 422 and an infrared detector 424 angled toward each other so as to have overlapping emission and detection fields, and hence a detection zone, at a location where a floor should be expected. IR proximity sensing can have a relatively narrow field of view, may depend on surface albedo for reliability, and can have varying range accuracy from surface to surface. As a result, multiple discrete sensors can be placed about the perimeter of the robot 100 to adequately detect cliffs from multiple points on the robot 100. Moreover, IR proximity based sensors typically cannot discriminate between a cliff and a safe event, such as just after the robot 100 climbs a threshold.

The cliff proximity sensors 420 can detect when the robot 100 has encountered a falling edge of the floor, such as when it encounters a set of stairs. The controller 500 (executing a control system) may execute behaviors that cause the robot 100 to take an action, such as changing its direction of travel, when an edge is detected. In some implementations, the sensor system 400 includes one or more secondary cliff sensors (e.g., other sensors configured for cliff sensing and optionally other types of sensing). The cliff detecting proximity sensors 420 can be arranged to provide early detection of cliffs, provide data for discriminating between actual cliffs and safe events (such as climbing over thresholds), and be positioned down and out so that their field of view includes at least part of the robot body 110 and an area away from the robot body 110. In some implementations, the controller 500 executes cliff detection routine that identifies and detects an edge of the supporting work surface (e.g., floor), an increase in distance past the edge of the work surface, and/or an increase in distance between the robot body 110 and the work surface. This implementation allows: 1) early detection of potential cliffs (which may allow faster mobility speeds in unknown environments); 2) increased reliability of autonomous mobility since the controller 500 receives cliff imaging information from the cliff detecting proximity sensors 420 to know if a cliff event is truly unsafe or if it can be safely traversed (e.g., such as climbing up and over a threshold); 3) a reduction in false positives of cliffs (e.g., due to the use of edge detection versus the multiple discrete IR proximity sensors with a narrow field of view). Additional sensors arranged as "wheel drop" sensors can be used for redundancy and for detecting situations where a range-sensing camera cannot reliably detect a certain type of cliff.

Threshold and step detection allows the robot 100 to effectively plan for either traversing a climbable threshold or avoiding a step that is too tall. This can be the same for random objects on the work surface that the robot 100 may or may not be able to safely traverse. For those obstacles or thresholds that the robot 100 determines it can climb, knowing their heights allows the robot 100 to slow down appropriately, if deemed needed, to allow for a smooth transition in order to maximize smoothness and minimize any instability due to sudden accelerations. In some implementations, threshold and step detection is based on object height above the work surface along with geometry recognition (e.g., discerning between a threshold or an electrical cable versus a blob, such as a sock). Thresholds may be recognized by edge detection. The controller 500 may receive imaging data from the cliff detecting proximity sensors 420 (or another imaging sensor on the robot 100), execute an edge detection routine, and issue a drive command based on results of the edge detection routine. The controller 500 may use pattern recognition to identify objects as well. Threshold detection allows the robot 100 to change its orientation with respect to the threshold to maximize smooth step climbing ability.

The proximity sensors 410, 420 may function alone, or as an alternative, may function in combination with one or more contact sensors 430 (e.g., bump switches) for redundancy. For example, one or more contact or bump sensors 430 on the robot body 110 can detect if the robot 100 physically encounters an obstacle. Such sensors may use a physical property such as capacitance or physical displacement within the robot 100 to determine when it has encountered an obstacle. In some implementations, each base body portion 124a, 124b, 124c of the base 120 has an associated contact sensor 430 (e.g., capacitive sensor, read switch, etc.) that detects movement of the corresponding base body portion 124a, 124b, 124c with respect to the base chassis 122 (see e.g., FIG. 4A). For example, each base 124a of body 120-c may move radially with respect to the Z axis of the base chassis 122, so as to provide three-way bump detection.

Referring again to FIGS. 1-4C, in some implementations, the sensor system 400 includes a laser scanner 440 mounted on a forward portion of the robot body 110 and in communication with the controller 500. In the examples shown, the laser scanner 440 is mounted on the base 124 of body 120 facing forward (e.g., having a field of view along the forward drive direction F) on or above the first base 124a of body 120 (e.g., to have maximum imaging coverage along the drive direction F of the robot). Moreover, the placement of the laser scanner on or near the front tip of the triangular base 120 means that the external angle of the robotic base (e.g., 300°) is greater than a field of view 442 of the laser scanner 440 (e.g., ~285°), thus preventing the base 120 from occluding or obstructing the detection field of view 442 of the laser scanner 440. The laser scanner 440 can be mounted recessed within the base body 124 as much as possible without occluding its fields of view, to minimize any portion of the laser scanner sticking out past the base body 124 (e.g., for aesthetics and to minimize snagging on obstacles).

The laser scanner 440 scans an area about the robot 100 and the controller 500, using signals received from the laser scanner 440, and creates an environment map or object map of the scanned area. The controller 500 may use the object map for navigation, obstacle detection, and obstacle avoidance. Moreover, the controller 500 may use sensory inputs from other sensors of the sensor system 400 for creating an object map and/or for navigation.

In some examples, the laser scanner 440 is a scanning LIDAR, which may use a laser that quickly scans an area in one dimension, as a "main" scan line, and a time-of-flight imaging element that uses a phase difference or similar technique to assign a depth to each pixel generated in the line (returning a two-dimensional depth line in the plane of scanning). In order to generate a three-dimensional map, the LIDAR can perform an "auxiliary" scan in a second direction (for example, by "nodding" the scanner). This mechanical scanning technique can be complemented, if not supplemented, by technologies such as the "Flash" LIDAR/LADAR and "Swiss Ranger" type focal plane imaging element sensors, techniques which use semiconductor stacks to permit time of flight calculations for a full two-dimensional matrix of pixels to provide a depth at each pixel, or even a series of depths at each pixel (with an encoded illuminator or illuminating laser).

The sensor system 400 may include one or more three-dimensional image sensors 450 in communication with the controller 500. If the three-dimensional image sensor 450 has a limited field of view, the controller 500 or the sensor system 400 can actuate the three-dimensional image sensor 450a in a side-to-side scanning manner to create a relatively wider field of view to perform robust obstacle detection/obstacle avoidance (ODOA). Referring to FIGS. 1-3B, in some implementations, the robot 100 includes a scanning three-dimensional image sensor 450a mounted on a forward portion of the robot body 110 with a field of view along the forward drive direction F (e.g., to have maximum imaging coverage along the drive direction F of the robot). The scanning three-dimensional image sensor 450a can be used primarily for ODOA. In the example shown, the scanning three-dimensional image sensor 450a is mounted on the torso 140 underneath the shoulder 142 or on the bottom surface 144 and recessed within the torso 140 (e.g., flush or past the bottom surface 144), as shown in FIG. 2, for example, to prevent user contact with the scanning three-dimensional image sensor 450a. The scanning three-dimensional image sensor 450 can be arranged to aim substantially downward and away from the robot body 110, so as to have a downward field of view 452 in front of the robot 100 for ODOA (e.g., with obstruction by the base 120 or other portions of the robot body 110). Placement of the scanning three-dimensional image sensor 450a on or near a forward edge of the torso 140 allows the field of view of the three-dimensional image sensor 450 (e.g., ~285°) to be less than an external surface angle of the torso 140 (e.g., 300°) with respect to the three-dimensional image sensor 450, thus preventing the torso 140 from occluding or obstructing the detection field of view 452 of the scanning three-dimensional image sensor 450a. Moreover, the scanning three-dimensional image sensor 450a (and associated actuator) can be mounted recessed within the torso 140 as much as possible without occluding its fields of view (e.g., also for aesthetics and to minimize snagging on obstacles). The distracting scanning motion of the scanning three-dimensional image sensor 450a is not visible to a user, creating a less distracting interaction experience. Unlike a protruding sensor or feature, the recessed scanning three-dimensional image sensor 450a will not tend to have unintended interactions with the environment (snagging on people, obstacles, etc.), especially when moving or scanning, as virtually no moving part extends beyond the envelope of the torso 140.

In some implementations, the sensor system 400 includes additional three-dimensional image sensors 450 disposed on the base 124 of body 120, the leg 130, the neck 150, and/or the head 160. In the example shown in FIG. 1, the robot 100 includes three-dimensional image sensors 450 on the base 124 of body 120, the torso 140, and the head 160. In the example shown in FIG. 3A, the robot 100 includes three-dimensional image sensors 450 on the base 124 of body 120, the torso 140, and the head 160. In the example shown in FIG. 3B, the robot 100 includes three-dimensional image sensors 450 on the leg 130, the torso 140, and the neck 150. Other configurations are possible as well. One three-dimensional image sensor 450 (e.g., on the neck 150 and over the head 160) can be used for people recognition, gesture recognition, and/or videoconferencing, while another three-dimensional image sensor 450 (e.g., on the base 120 and/or the leg 130) can be used for navigation and/or obstacle detection and obstacle avoidance.

A forward facing three-dimensional image sensor 450 disposed on the neck 150 and/or the head 160 can be used for person, face, and/or gesture recognition of people about the robot 100. For example, using signal inputs from the three-dimensional image sensor 450 on the head 160, the controller 500 may recognize a user by creating a three-dimensional map of the viewed/captured user's face and comparing the created three-dimensional map with known three-dimensional images of people's faces and determining a match with one of the known three-dimensional facial images. Facial recognition may be used for validating users as allowable users of the robot 100. Moreover, one or more of the three-dimensional image sensors 450 can be used for determining gestures of a person viewed by the robot 100, and optionally reacting based on the determined gesture(s) (e.g., hand pointing, waving, and/or hand signals). For example, the controller 500 may issue a drive command in response to a recognized hand pointing in a particular direction.

The three-dimensional image sensors 450 may be capable of producing the following types of data: (i) a depth map, (ii) a reflectivity based intensity image, and/or (iii) a regular intensity image. The three-dimensional image sensors 450 may obtain such data by image pattern matching, measuring the flight time and/or phase delay shift for light emitted from a source and reflected off of a target.

In some implementations, reasoning or control software, executable on a processor (e.g., of the robot controller 500), uses a combination of algorithms executed using various data types generated by the sensor system 400. The reasoning software processes the data collected from the sensor system 400 and outputs data for making navigational decisions on where the robot 100 can move without colliding with an obstacle, for example. By accumulating imaging data over time of the robot's surroundings, the reasoning software can in turn apply effective methods to selected segments of the sensed image(s) to improve depth measurements of the three-dimensional image sensors 450. This may include using appropriate temporal and spatial averaging techniques.

The reliability of executing robot collision-free moves may be based on: (i) a confidence level built by high-level reasoning over time and (ii) a depth-perceptive sensor that accumulates three major types of data for analysis: (a) a depth image, (b) an active illumination image and (c) an ambient illumination image. Algorithms cognizant of the different types of data can be executed on each of the images obtained by the depth-perceptive image sensor 450. The aggregate data may improve the confidence level compared to a system using only one of the kinds of data.

The three-dimensional image sensors 450 may obtain images containing depth and brightness data from a scene about the robot 100 (e.g., a sensor view portion of a room or work area) that contains one or more objects. The controller 500 may be configured to determine occupancy data for the object based on the captured reflected light from the scene. Moreover, the controller 500, in some examples, issues a drive command to the drive system 200 based at least in part on the occupancy data to circumnavigate obstacles (i.e., the object in the scene). The three-dimensional image sensors 450 may repeatedly capture scene depth images for real-time decision-making by the controller 500 to navigate the robot 100 about the scene without colliding into any objects in the scene. For example, the speed or frequency in which the depth image data is obtained by the three-dimensional image sensors 450 may be controlled by a shutter speed of the three-dimensional image sensors 450. In addition, the controller 500 may receive an event trigger (e.g., from another sensor component of the sensor system 400, such as proximity sensor 410, 420, notifying the controller 500 of a nearby object or hazard. The controller 500, in response to the event trigger, can cause the three-dimensional image sensors 450 to increase a frequency at which depth images are captured and occupancy information is obtained.

In some implementations, the robot includes a sonar scanner 460 for acoustic imaging of an area surrounding the robot 100. In the examples shown in FIGS. 1 and 2, the sonar scanner 460 is disposed on a forward portion of the base 124 of body 120.

Referring to FIGS. 1-3B, in some implementations, the robot 100 uses the laser scanner or laser range finder 440 for redundant sensing, as well as a rear-facing sonar proximity sensor 410j for safety, both of which are oriented parallel to the ground G. The robot 100 may include first and second three-dimensional image sensors 450a, 450b (depth cameras) to provide robust sensing of the environment around the robot 100. The first three-dimensional image sensor 450a is mounted on the torso 140 and pointed downward at a fixed angle to the ground G. By angling the first three-dimensional image sensor 450a downward, the robot 100 receives dense sensor coverage in an area immediately forward or adjacent to the robot 100, which is relevant for short-term travel of the robot 100 in the forward direction. The rear-facing sonar 410j provides object detection when the robot travels backward. If backward travel is typical for the robot 100, the robot 100 may include a third 3D image sensor 450 facing downward and backward to provide dense sensor coverage in an area immediately rearward or adjacent to the robot 100.

The second three-dimensional image sensor 450b is mounted on the head 160, which can pan and tilt via the neck 150. The second three-dimensional image sensor 450b can be useful for remote driving since it allows a human operator to see where the robot 100 is going. The neck 150 enables the operator tilt and/or pan the second three-dimensional image sensor 450b to see both close and distant objects. Panning the second three-dimensional image sensor 450b increases an associated horizontal field of view. During fast travel, the robot 100 may tilt the second three-dimensional image sensor 450b downward slightly to increase a total or combined field of view of both three-dimensional image sensors 450a, 450b, and to give sufficient time for the robot 100 to avoid an obstacle (since higher speeds generally mean less time to react to obstacles). At slower speeds, the robot 100 may tilt the second three-dimensional image sensor 450b upward or substantially parallel to the ground G to track a person that the robot 100 is meant to follow. Moreover, while driving at relatively low speeds, the robot 100 can pan the second three-dimensional image sensor 450b to increase its field of view around the robot 100. The first three-dimensional image sensor 450a can stay fixed (e.g., not moved with respect to the base 120) when the robot is driving to expand its perceptual range. Additionally and/or alternatively, the first three-dimensional image sensor 450a can scan at low speeds in order to detect potential obstacles around the robot when it is maneuvering. In some examples, the height of the first three-dimensional image sensor 450a can be adjusted upward, such as through the use of a Z-lift, in order to optimize the field of view of the first three-dimensional sensor 450a.

In some implementations, at least one of three-dimensional image sensors 450 can be a volumetric point cloud imaging device (such as a speckle or time-of-flight camera) positioned on the robot 100 at a height of greater than one or two feet above the ground (or at a height of about one or two feet above the ground) and directed to obtain a point cloud from a volume of space including a floor plane in a direction of movement of the robot (via the omni-directional drive system 200). In the examples shown in FIGS. 1 and 3, the first three-dimensional image sensor 450a can be positioned on the base 120 at height of greater than one or two feet above the ground and aimed along the forward drive direction F to capture images (e.g., volumetric point cloud) of a volume including the floor while driving (e.g., for obstacle detection and obstacle avoidance). The second three-dimensional image sensor 450b is shown mounted on the head 160 (e.g., at a height greater than about three or four feet above the ground), so as to obtain skeletal recognition and definition point clouds from a volume of space adjacent the robot 100. The controller 500 may execute skeletal/digital recognition software to analyze data of the captured volumetric point clouds.

Referring to FIGS. 3A-4C, the sensor system 400 may include an inertial measurement unit (IMU) 470 in communication with the controller 500 to measure and monitor a moment of inertia of the robot 100 with respect to the overall center of gravity $CG_R$ of the robot 100.

The controller 500 may monitor any deviation in feedback from the IMU 470 from a threshold signal corresponding to normal unencumbered operation. For example, if the robot begins to pitch away from an upright position, it may be "clotheslined" or otherwise impeded, or someone may have suddenly added a heavy payload. In these instances, it may be necessary to take urgent action (including, but not limited to, evasive maneuvers, recalibration, and/or issuing an audio/visual warning) in order to assure safe operation of the robot 100.

Since robot 100 may operate in a human environment, it may interact with humans and operate in spaces designed for humans (and without regard for robot constraints). The robot 100 can limit its drive speeds and accelerations when in a congested, constrained, or highly dynamic environment, such as at a cocktail party or busy hospital. However, the robot 100 may encounter situations where it is safe to drive relatively fast, as in a long empty corridor, but yet be able to decelerate suddenly, as when something crosses the robot's motion path.

When accelerating from a stop, the controller 500 may take into account a moment of inertia of the robot 100 from its overall center of gravity $CG_R$ to prevent robot tipping. The controller 500 may use a model of its pose, including its current moment of inertia. When payloads are supported, the controller 500 may measure a load impact on the overall center of gravity $CG_R$ and monitor movement of the robot moment of inertia. For example, the torso 140 and/or neck 150 may include strain gauges to measure strain. If this is not possible, the controller 500 may apply a test torque command to the drive wheels 210 and measure actual linear and angular acceleration of the robot using the IMU 470, in order to experimentally determine safe limits.

During a sudden deceleration, a commanded load on the second and third drive wheels 210b, 210c (the rear wheels) is reduced, while the first drive wheel 210a (the front wheel) slips in the forward drive direction and supports the robot 100. If the loading of the second and third drive wheels 210b, 210c (the rear wheels) is asymmetrical, the robot 100 may "yaw" which will reduce dynamic stability. The IMU 470 (e.g., a gyro) can be used to detect this yaw and command the second and third drive wheels 210b, 210c to reorient the robot 100.

Figure 5:
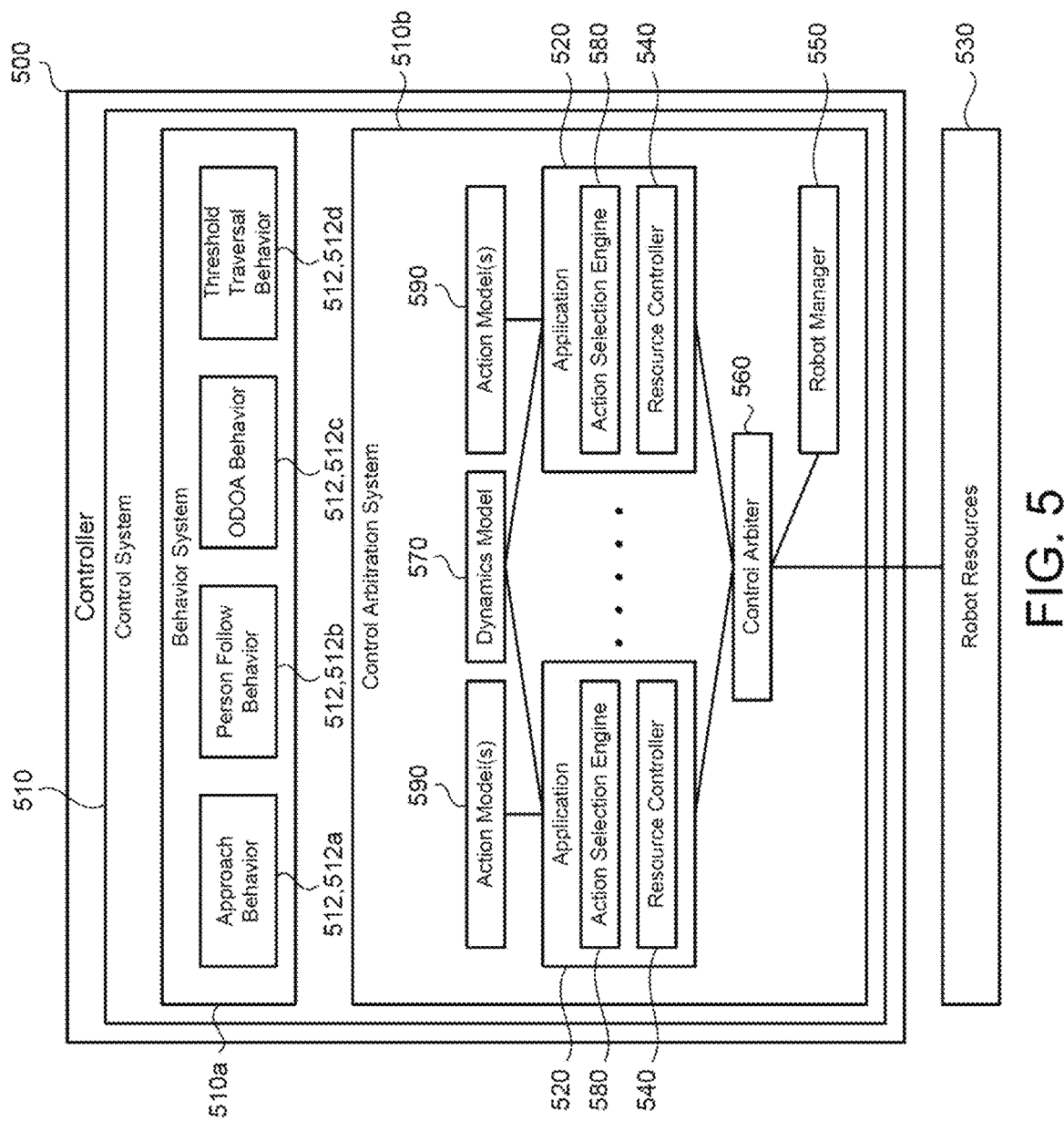
FIG. 5 is a schematic view of an example control system executed by a controller of a telepresence robot.

Referring to FIG. 5, in some implementations, the controller 500 executes a control system 510, which includes a behavior system 510a and a control arbitration system 510b in communication with each other. The control arbitration system 510b allows applications 520 to be dynamically added and removed from the control system 510, and facilitates allowing applications 520 to each control the robot 100 without needing to know about any other applications 520. In other words, the control arbitration system 510b provides a simple prioritized control mechanism between applications 520 and resources 530 of the robot 100. The resources 530 may include the drive system 200, the sensor system 400, and/or any payloads or controllable devices in communication with the controller 500.

The applications 520 can be stored in memory of or communicated to the robot 100, to run concurrently on (e.g., a processor) and simultaneously control the robot 100. The applications 520 may access behaviors 512 of the behavior system 510a. The independently deployed applications 520 are combined dynamically at runtime and share robot resources 530 (e.g., drive system 200, arm(s), head(s), etc.) of the robot 100. A low-level policy is implemented for dynamically sharing the robot resources 530 among the applications 520 at run-time. The policy determines which application 520 has control of the robot resources 530 required by that application 520 (e.g. it creates a priority hierarchy among the applications 520). Applications 520 can start and stop dynamically and run completely independently of each other. The control system 510 also allows for complex behaviors 512 which can be combined together to assist each other.

The control arbitration system 510b includes one or more resource controllers 540, a robot manager 550, and one or more control arbiters 560. These components do not need to be in a common process or computer, and do not need to be started in any particular order. The resource controller 540 component provides an interface to the control arbitration system 510b for applications 520. There is an instance of this component for every application 520. The resource controller 540 abstracts and encapsulates away the complexities of authentication, distributed resource control arbiters, command buffering, and the like. The robot manager 550 coordinates the prioritization of applications 520, by controlling which application 520 has exclusive control of any of the robot resources 530 at any particular time. Since this is the central coordinator of information, there is only one instance of the robot manager 550 per robot. The robot manager 550 implements a priority policy, which has a linear prioritized order of the resource controllers 540, and keeps track of the resource control arbiters 560 that provide hardware control. The control arbiter 560 receives the commands from every application 520 generates a single command based on the applications' priorities and publishes it for its associated resources 530. The control arbiter 560 also receives state feedback from its associated resources 530 and sends it back up to the applications 520. The robot resources 530 may be a network of functional modules (e.g. actuators, drive systems, and groups thereof) with one or more hardware controllers. The commands of the control arbiter 560 are specific to the resource 530 to carry out specific actions.

A dynamics model 570 executable on the controller 500 can be configured to compute the center of gravity (CG), moments of inertia, and cross products of inertia of various portions of the robot 100 for the assessing a current robot state. The dynamics model 570 may also model the shapes, weight, and/or moments of inertia of these components. In some examples, the dynamics model 570 communicates with the IMU 470 or portions of one (e.g., accelerometers and/or gyros) disposed on the robot 100 and in communication with the controller 500 for calculating the various centers of gravity of the robot 100. The dynamics model 570 can be used by the controller 500, along with other programs 520 or behaviors 512 to determine operating envelopes of the robot 100 and its components.

Each application 520 has an action selection engine 580 and a resource controller 540, one or more behaviors 512 connected to the action selection engine 580, and one or more action models 590 connected to action selection engine 580. The behavior system 510a provides predictive modeling and allows the behaviors 512 to collaboratively decide on the robot's actions by evaluating possible outcomes of robot actions. In some examples, a behavior 512 is a plug-in component that provides a hierarchical, state-full evaluation function that couples sensory feedback from multiple sources with a-priori limits and information into evaluation feedback on the allowable actions of the robot. Since the behaviors 512 can be plugged into the application 520 (e.g., residing inside or outside of the application 520), they can be removed and added without having to modify the application 520 or any other part of the control system 510. Each behavior 512 is a standalone policy. To make behaviors 512 more powerful, it is possible to attach the output of multiple behaviors 512 together into the input of another so as to have complex combination functions. The behaviors 512 are intended to implement manageable portions of the total cognizance of the robot 100.

The action selection engine 580 is the coordinating element of the control system 510 and runs a fast, optimized action selection cycle (prediction/correction cycle) searching for the best action given the inputs of all the behaviors 512. The action selection engine 580 has three phases: nomination, action selection search, and completion. In the nomination phase, each behavior 512 is notified that the action selection cycle has started and is provided with the cycle start time, the current state, and limits of the robot actuator space. Based on internal policy or external input, each behavior 512 decides whether or not it wants to participate in this action selection cycle. During this phase, a list of active behavior primitives is generated whose input will affect the selection of the commands to be executed on the robot 100.

In the action selection search phase, the action selection engine 580 generates feasible outcomes from the space of available actions, also referred to as the action space. The action selection engine 580 uses the action models 590 to provide a pool of feasible commands (within limits) and corresponding outcomes as a result of simulating the action of each command at different time steps with a time horizon in the future. The action selection engine 580 calculates a preferred outcome, based on the outcome evaluations of the behaviors 512, and sends the corresponding command to the control arbitration system 510b and notifies the action model 590 of the chosen command as feedback.

In the completion phase, the commands that correspond to a collaborative best scored outcome are combined together as an overall command, which is presented to the resource controller 540 for execution on the robot resources 530. The best outcome is provided as feedback to the active behaviors 512, to be used in future evaluation cycles.

Received sensor signals from the sensor system 400 can cause interactions with one or more behaviors 512 to execute actions. For example, using the control system 510, the controller 500 selects an action (or move command) for each robotic component (e.g., motor or actuator) from a corresponding action space (e.g., a collection of possible actions or moves for that particular component) to effectuate a coordinated move of each robotic component in an efficient manner that avoids collisions with itself and any objects about the robot 100, which the robot 100 is aware of. The controller 500 can issue a coordinated command over robot network, such as an EtherIO network, as described in U.S. Ser. No. 61/305,069, filed Feb. 16, 2010, the entire contents of which are hereby incorporated by reference.

Figure 6A:
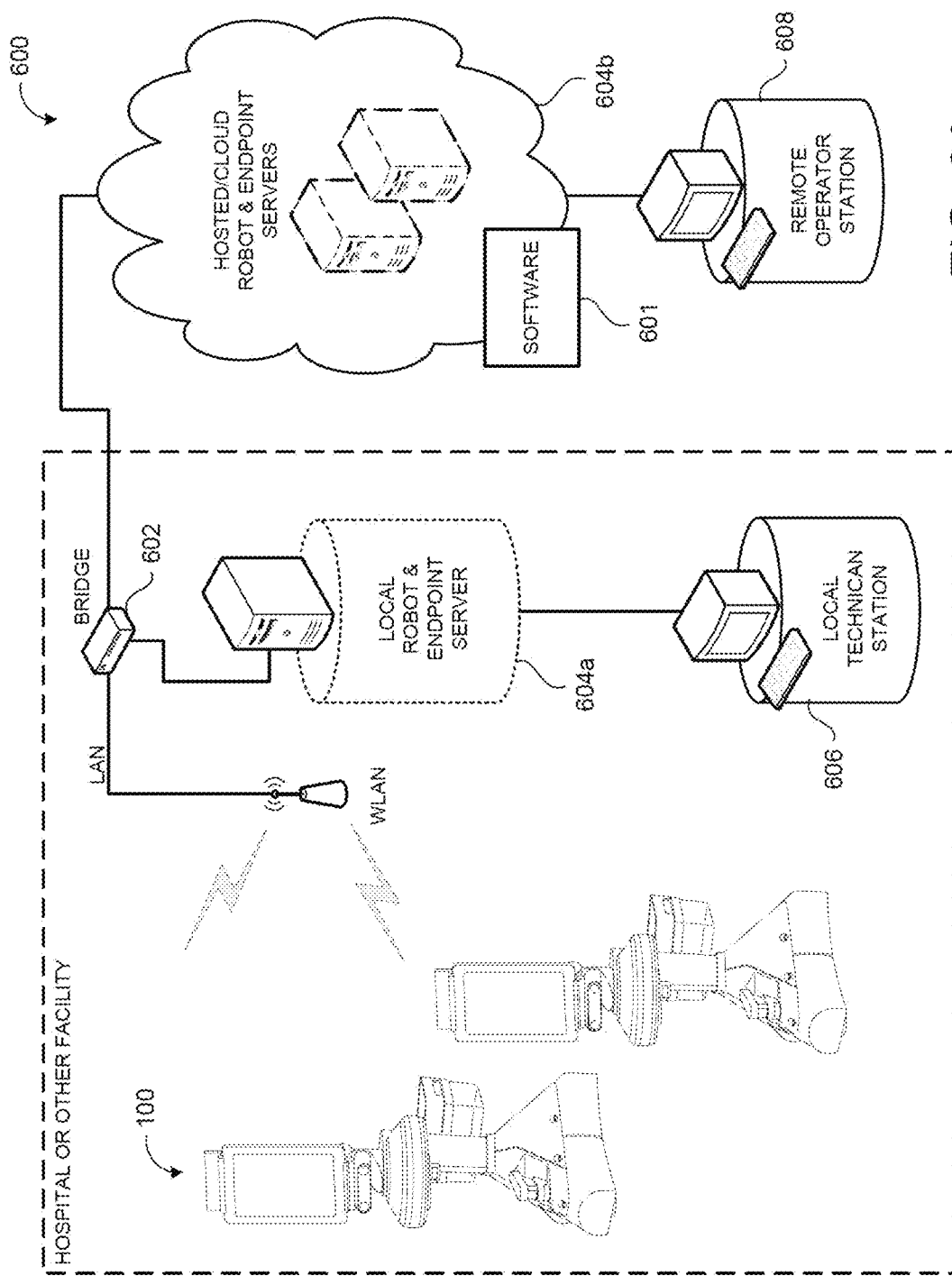
FIG. 6A provides a schematic view of an example robot system including multiple robots in communication with robot endpoint servers.

FIG. 6A provides a schematic view of an example robot system 600 having one or more telepresence robots 100 in communication with a bridge 602, which communicates with a local robot endpoint server 604a and a remote endpoint server 604b (e.g., such as the cloud computing service 720 (FIG. 7)). The local robot endpoint server 604a communicates with a local technician computing device 606 and the remote endpoint server 604b communicates with a remote operator computing device 608.

Referring to FIGS. 2 and 4C, in some implementations, the robot 100 includes multiple antennas. In the examples shown, the robot 100 includes a first antenna 490a and a second antenna 490b both disposed on the base 120 (although the antennas may be disposed at any other part of the robot 100, such as the leg 130, the torso 140, the neck 150, and/or the head 160). The use of multiple antennas provides robust signal reception and transmission. The use of multiple antennas provides the robot 100 with multiple-input and multiple-output (MIMO) which is the use of multiple antennas for a transmitter and/or a receiver to improve communication performance. MIMO offers significant increases in data throughput and link range without additional bandwidth or transmit power. It achieves this by higher spectral efficiency (more bits per second per hertz of bandwidth) and link reliability or diversity (reduced fading). Because of these properties, MIMO is an important part of modern wireless communication standards such as IEEE 802.11n (Wifi), 4G, 3GPP Long Term Evolution, WiMAX and HSPA+. Moreover, the robot 100 can act as a Wi-Fi bridge, hub or hotspot for other electronic devices nearby. The mobility and use of MIMO of the robot 100 can allow the robot to serve as a relatively reliable Wi-Fi bridge 602.

Figure 6B:
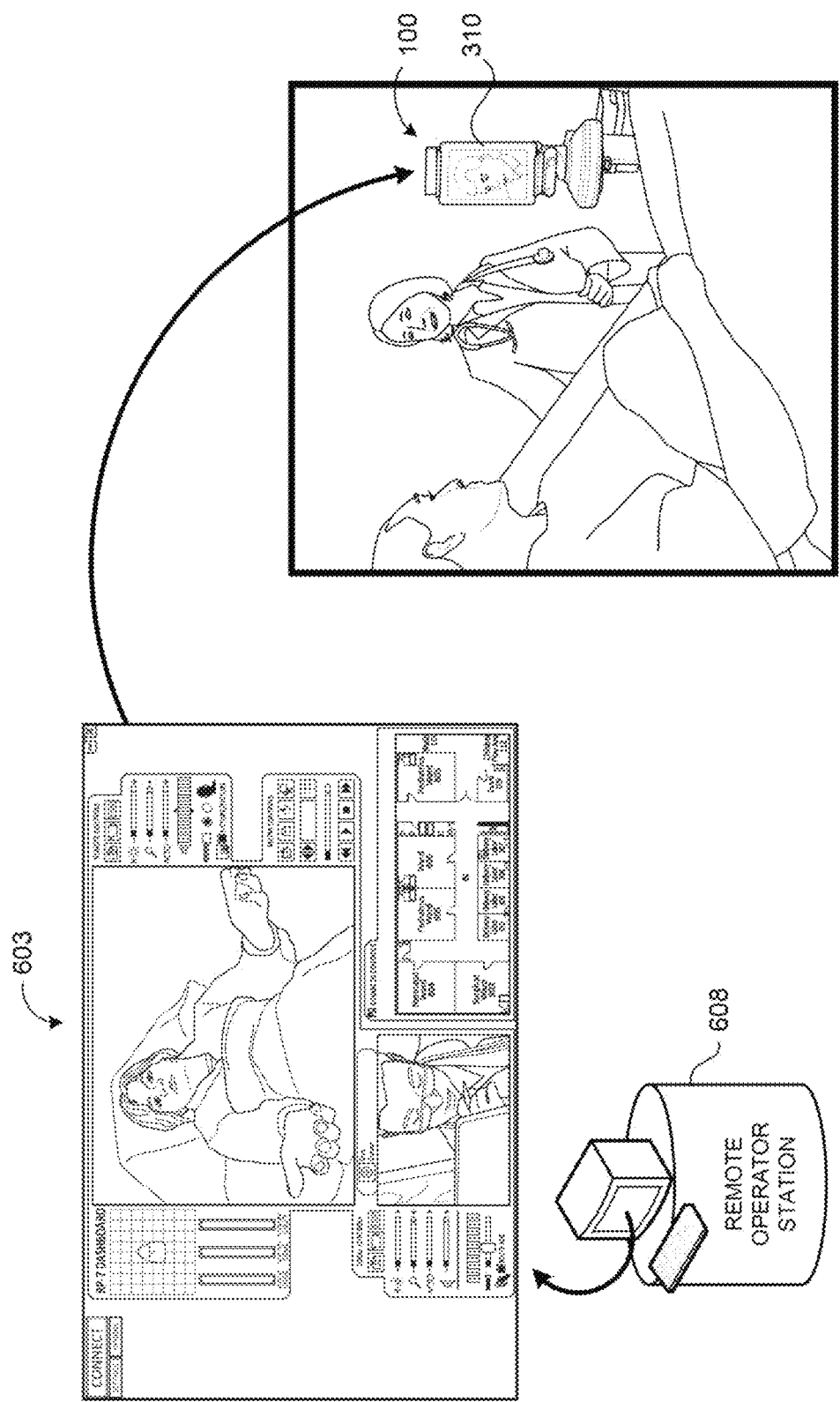
FIG. 6B illustrates a teleoperation software application executed by a robot or a terminal.

Referring to FIGS. 6A and 6B, a teleoperation software application 601 executes on at least one of the robot controller 500, the local robot endpoint server 604a, the remote endpoint server 604b, the local technician computing device 606 and the remote operator computing device 608. In some examples, a portion of the teleoperation software application 601 executes on one or more of the aforementioned devices. The teleoperation software application 601 allows one or more users to interact with the robot 100 (e.g., to drive the robot 100) and/or remotely with other people or objects adjacent the robot 100 through telepresence features of the robot 100.

Figure 6C:
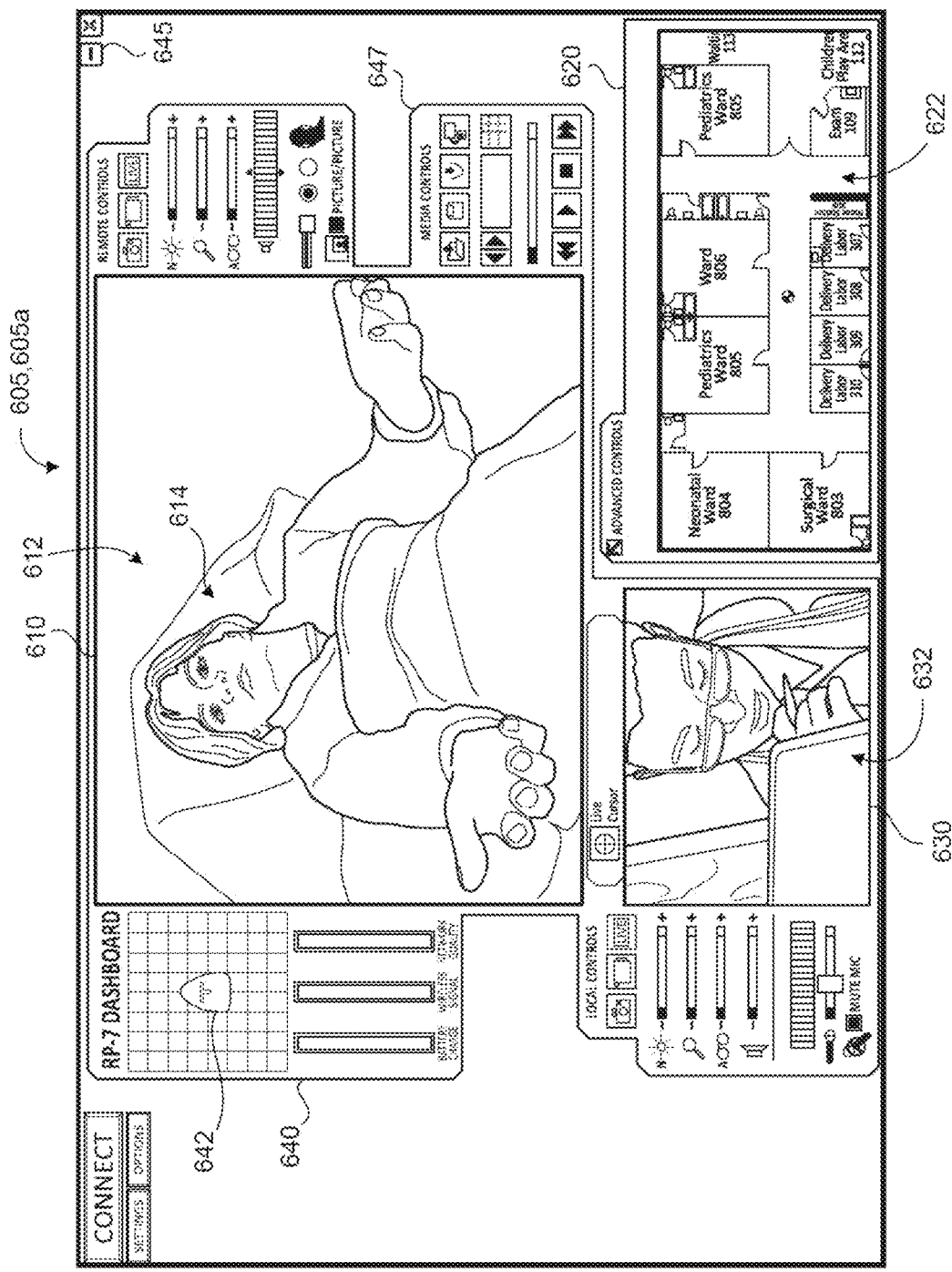
FIG. 6C illustrates one embodiment of a screen shot of a user interface for controlling navigation of a semi-autonomous telepresence robot.

FIG. 6C provides a schematic view of an example user interface 605 of the teleoperation software application 601 that can be rendered on a display, such as the touch screen 312 of the web pad 310 and/or the remote operator computing device 608, for controlling navigation, telepresence, and/or other aspects of the robot 100. The user interface 605 includes a remote video feed window 610 displaying a remote view 612, such as a video feed of a patient 614. The video feed may be generated by one of the cameras 320, 450 on the robot 100. The user interface 605 may display a plan view map window 620 having a map 622 of the local area in which the robot 100 is operating. In the example shown, the map 622 displayed in the plan view map window 620 is a two-dimensional, top-down map 622a (FIG. 6D); however, other types of maps are possible as well. The user interface 605 may also include a local video window 630 displaying a local view 632, such as a video feed of the user (e.g., remote from the robot 100). The video feed displayed in the local video window 630 may be transmitted to the robot 100 and displayed to the patient 614 using a display device, such as the web pad 310 on the robot 100.

A dashboard 640 may provide information regarding the orientation of the robot 100, an indication of the robot's battery charge, an indication of the strength of a wireless data signal, and/or an indication of the network quality. The orientation of the robot 100 may be indicated by an icon 642 displaying the orientation of the head 160 of the robot 100 with respect to the torso 140 or the base 120. Such an indication may assist a user in orienting the robot 100 to view items of interest. The range of motion of the robot head

160 may be limited. Accordingly, certain implementations may display an indication of the rotational position of the head 160 and a range of motion of the head 160.

Media controls 647 may allow the user to interact with the patient 614 using various types of media and to acquire and store media documenting the interactions of the user and the patient 614. The media controls 647 may allow the user to play audio and/or video clips, for example, that may be used to educate the patient 614 about a medical condition or procedure. Still photographs may be acquired using a camera 320, 450 of the robot 100 in order to document various conditions. Further, the robot 100 may acquire audio (e.g., using the microphone 330) or video (e.g., using the camera 320) documenting the user's interaction with the patient 614 and optionally storing the acquired audio/video in memory of the controller 500 and/or transmitting the acquired audio/video to a remote device or cloud service.

In some implementations, the media controls 647 allow the user to manage temporary connectivity issues. For example, upon the unexpected disconnection of a session, video recording may begin. The robot 100 may continue recording video and saving it to local memory, such as that of the controller 500. Upon an unexpected disconnection, a message may be displayed by the robot, such as "Session terminated—Video recording continuing . . . ." A button below may be displayed with a caption of "Stop recording." A nurse on the robot side may touch the "Stop recording" button (e.g., on the touch screen 312) and terminate the local recording. Otherwise, the recording may continue for a specified time interval. If the same user logs back into the robot 100 in the specified time interval, the record button on the remote station may show that recording is in progress. When the robot's local recording is complete, it may begin to transmit the video file to a remote station or other location that may be accessible to the disconnected user. Accordingly, the user may be able to see what events transpired during the time that the session was interrupted.

In the example shown in FIG. 6C, the remote video feed window 610 occupies a relatively large portion of the display area. The user interface 605 may have the remote video feed window 610 rendered at a 640×480 pixel resolution, the local video window 630 at a 320×240 pixel resolution, and the plan view map window 620 at a 530×200 pixel resolution. Accordingly, this view may be most appropriate when the user is communicating with the patient 614 and/or manually driving the robot 100. The layout of the default user interface 605a shown in FIG. 6C may allow the user to swap the contents of the plan view map window 620 with the remote video feed window 610. The view may be swapped, for example, by double-clicking on the map window 620. The windows could later be swapped back by double-clicking on the remote video feed window 610.

Alternative screen layouts may be displayed to a user as may be appropriate for the task being performed by the user. In the example shown in FIG. 6D, in anticipation of directing the robot 100 to move using semi-autonomous navigation from one location to another, the size of the plan view map window 620 is increased. For example, the user interface 605, 605a shown in FIG. 6C can be a default state for patient interaction and the user interface 605, 605b shown in FIG. 6D can be an alternate state for robot navigation.

A map view switch button 645 of the user interface may allow the user to invoke the alternative user interface 605b that includes a relatively larger map window 620. For example, the user interface 605b shown in FIG. 6D may be primarily used to manually drive the robot 100 or to autonomously navigate to a desired destination Clicking the map view switch button 645 again takes the user back to the default user interface 605a, which may be used when actively performing a medical consultation. Accordingly, a user may emphasize or de-emphasize (e.g., maximize or minimize) the plan view map window 620 as desired. Certain of the windows shown in the alternate user interface 605b are also displayed, such as the remote video feed window 610 and the local video window 630. In some examples, the plan view map window 620 may be displayed at an 880×700 pixel resolution, the remote video feed window 610 may be displayed at a 320×240 pixel resolution, and the local video window 630 may be displayed at a 160×120 pixel resolution.

Figure 6D:
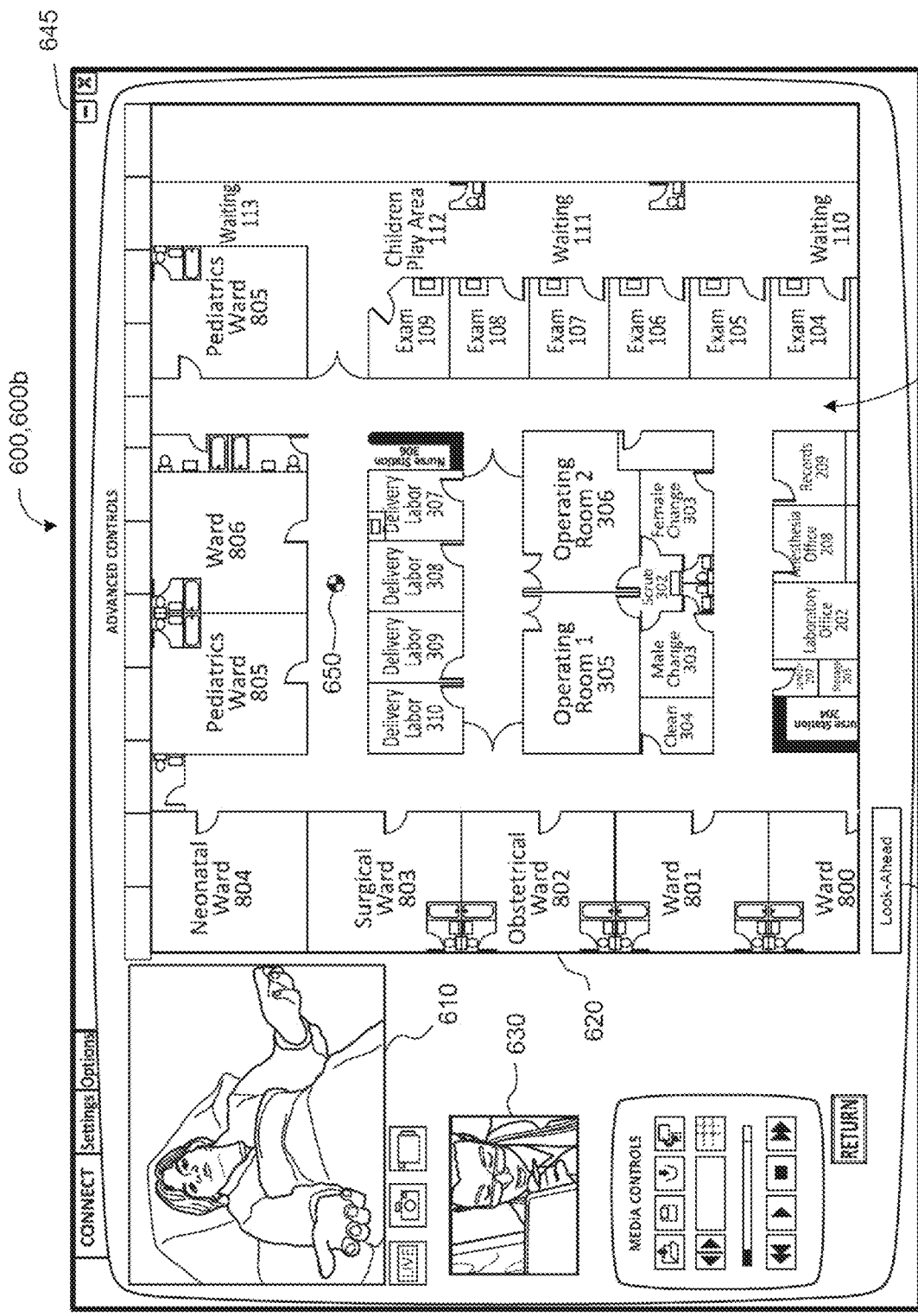
FIG. 6D illustrates a screen shot, in which the relative area of the screen devoted to the map window is increased.

Referring to FIG. 6D, the plan view map window 620 may provide a robot location icon 650 designating a location of the robot 100 within the local environment. A user may click on or touch a point on the displayed map 622 in order to cause the robot to semi-autonomously or autonomously navigate to the selected point. In some examples, the user may zoom in and out using a mouse wheel while the cursor is over the plan view map window 620 or by touch gestures, when displayed on a touch screen 312.

Simultaneous localization and mapping (SLAM) technology may utilize laser range scanners, odometry, acoustic range finders, or all of the above to build a map of the local environment and place the robot 100 on the map. Images recorded by a robot 100 (e.g., via the camera 320 or three-dimensional image sensor 450) as it traverses an environment may be stored in an internal database (e.g., of the controller 500) and/or a remote database (e.g., a cloud service). When the robot 100 reacquires an image currently in the database, the algorithm resets the robot's current position to that which was recorded when the landmark was originally entered in the database. This method helps to counter the inherent drift of wheel encoder odometry. Systems may also utilize RFID chips and/or triangulation of wireless access points. Further, the names or identifying numbers of specific rooms may be associated with locations on the map. Image data can accumulate over time and, as a cost savings or space savings, the robot 100 may use remote data storage and/or remote processing for storing and/or processing the image data, respectively. For example, an RFID reader may detect RFID chips associated with coordinates on a plan view map in order to identify a current location of a robot. An "RFID chip" may include an RFID device or an RFID "tag" as is understood by those having skill in the art. The RFID chips may be embodied as passive, active, or battery assisted passive (BAP) RFID chips.

Figure 7:
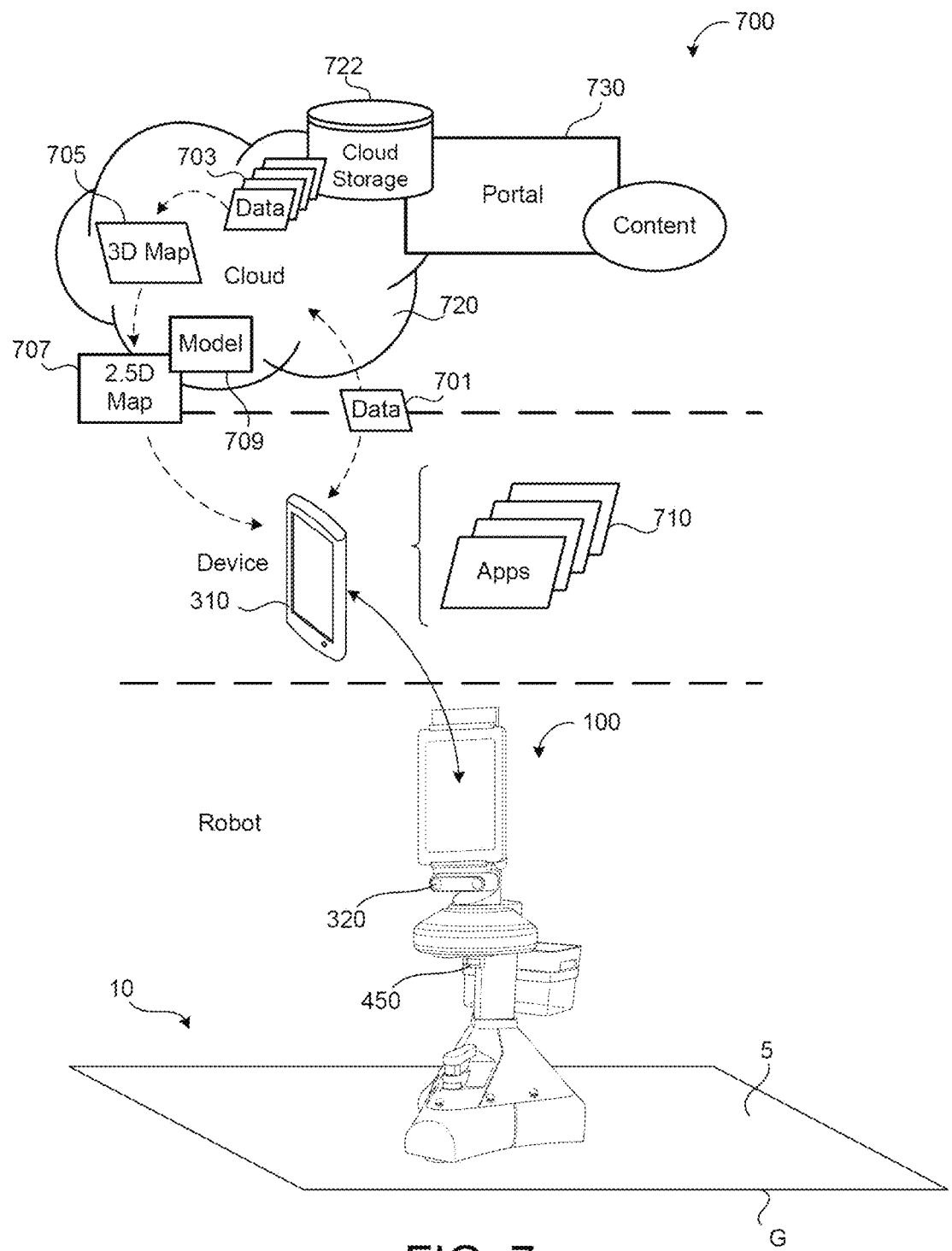
FIG. 7 is a schematic view of an example robot system architecture.

FIG. 7 provides a schematic view of an example robot system architecture 700, which may include the robot 100 (or a portion thereof, such as the controller 500 or drive system 200), a computing device 310 (e.g., detachably or fixedly attached to the head 160), a cloud 720 (i.e., cloud computing service), and a portal 730. The computing device 310 may execute one or more robot applications 710, which may include software applications (e.g., stored in memory and executable on a processor) for security, medicine compliance, telepresence, behavioral coaching, social networking, active alarm, home management, etc. The computing device 310 may provide communication capabilities (e.g., secure wireless connectivity and/or cellular communication), refined application development tools, speech recognition, and person or object recognition capabilities. The computing device 310 in some examples utilizes an interaction/COMS featured operating system, such as Android provided by Google Inc., iOS provided by Apple, Inc., or other smart phone operating systems, or specialized robot operating systems, such as RSS A2.

The cloud 720 provides cloud computing and/or cloud storage capabilities. Cloud computing may provide Internet-based computing, whereby shared servers provide resources, software, and data to computers and other devices on demand. For example, the cloud 720 may be a cloud computing service that includes at least one server computing device, which may include a service abstraction layer and a hypertext transfer protocol wrapper over a server virtual machine instantiated thereon. The server computing device may be configured to parse HTTP requests and send HTTP responses. Cloud computing may be a technology that uses the Internet and central remote servers to maintain data and applications. Cloud computing can allow users to access and use applications 710 without installation and to access personal files at any computer with Internet access. Cloud computing allows for relatively more efficient computing by centralizing storage, memory, processing and bandwidth. The cloud 720 can provide scalable, on-demand computing power, storage, and bandwidth, while reducing robot hardware requirements (e.g., by freeing up CPU and memory usage). Robot connectivity to the cloud 720 allows automatic data gathering of robot operation and usage histories without requiring the robot 100 to return to a base station. Moreover, continuous data collection over time can yield a wealth of data that can be mined for marketing, product development, and support.

Cloud storage 722 can be a model of networked computer data storage where data is stored on multiple virtual servers, generally hosted by third parties. By providing communication between the robot 100 and the cloud 720, information gathered by the robot 100 can be securely viewed by authorized users via a web-based information portal.

The portal 730 may be a web-based user portal for gathering and/or providing information, such as personal information, home status information, and robot status information. Information can be integrated with third-party information to provide additional functionality and resources to the user and/or the robot 100. The robot system architecture 700 can facilitate proactive data collection. For example, applications 710 executed on the computing device 310 may collect data and report on actions performed by the robot 100 and/or a person or an environment viewed by the robot 100 (using the sensor system 400). This data can be a unique property of the robot 100.

"Dense data" vs. "sparse data" and "dense features" vs. "sparse features" are referred to herein with respect to spatial data sets. Without limiting or narrowing the meaning from that of how those skilled in the art would interpret such terms to mean, "dense" vs. "sparse" generally means many data points per spatial representation vs. few data points, and specifically may mean:

(i) in the context of two-dimensional image data or three-dimensional "images" including two-dimensional data and range, "dense" image data includes image data substantially fully populated with pixels, or capable of being rasterized to pixels with substantially no losses and/or artifacting from the original image capture (including substantially uncompressed, raw, or losslessly compressed images), while a "sparse" image is one where the image is quantized, sampled, lossy compressed, vectorized, segmented (e.g., into superpixels, nodes, edges, surfaces, interest points, voxels), or otherwise materially reduced in fidelity from the original capture, or must be interpolated in being rasterized to pixels to re-represent an image;

(ii) in the context of two-dimensional or three-dimensional features, "dense features" may be features that are populated in a substantially unconstrained manner, to the resolution of the detection approach, all that can be detected and recorded, and/or features that are recognized by detectors recognized to collect many features (HOG, wavelets) over a sub-image; "sparse features" may be purposefully constrained in number, in the number of feature inputs, lateral inhibition, and/or feature selection, and/or may be recognized by detectors recognized to identify a limited number of isolated points in an image (Harris corner, edges, Shi-Tomasi).

With respect to three-dimensional environment structure, the robot 100 may acquire images, such as dense images 701, of a scene 10 about the robot 100 while maneuvering about a work surface 5. In some implementations, the robot 100 uses a camera 320 and/or an image sensor 450 (e.g., volumetric point cloud imaging device) for obtaining the dense images 701. The controller 500, which is in communication with the camera 320 and/or the image sensor 450 may associate information with the dense images 701 (e.g., mark-up or tag the dense images 701 with data), such as accelerometer data traces, odometry data, and/or other data from the sensor system 400 along with timestamps. In some examples, the robot 100 captures a streaming sequence of dense images 701 and marks the dense image sequence with mark-up data, providing a marked-up dense image sequence. The cloud service 720 may process the received image data 701 and return a processed data set to the robot controller 500, which may issue drive commands to the drive system 200 based on the received processed data set for maneuvering about the scene 10.

The cloud service 720 may execute one of a variety of off-line methods to process a stored image data set 703 into a dense three-dimensional map or model 705 of the scene 10 (environment) and then simplify this dense three-dimensional map or model 705 into a two-dimensional height map 707, which can be a two-dimensional map with height data at each point (e.g., similar to a two-dimensional topographical map). In some examples, the two-dimensional height map 707 is a topographical map having X and Y coordinates with Z data. Each X,Y coordinate may have one or more Z points (i.e., height data). Unlike the dense three-dimensional map, which may have numerous Z points (e.g., hundreds or thousands of Z points) for each X,Y coordinate, the two-dimensional height map 707 may have less than threshold number of Z points for each X,Y coordinate, such as between 2 and 20 (e.g., 10) points. A two-dimensional height map 707 derived from a three-dimensional map of a table in a room may show a first Z point for the bottom surface of a table top and a second Z point for the top surface of the table top for each X,Y coordinate along the table. This information allows the robot 100 to determine if it can pass under the table top. By reducing the Z points from a dense data set of a continuous range of Z points for each X,Y coordinate to a sparse data set of a select number of Z points indicative of a detected objects 12, the robot 100 can receive a two-dimensional height map 707 having a relatively smaller size than the three-dimensional map used by the cloud service 720. This, in turn, allows the robot 100 to store the two-dimensional height map 707 on local memory having a practical and cost effective size as compared to the scalable memory space available to the cloud service 720. The robot 100 receives the two-dimensional height map 707 from the cloud 720, which provides the robot 100 and associated controller 500 with navigational data for future work in the scene 10.

Additional methods and features of three-dimensional map data compression are disclosed in "Multi-Level Surface Maps for Outdoor Terrain Mapping and Loop Closing" by R. Triebel, P. Pfaff and W. Burgard; IEEE/RSJ International Conference on Intelligent Robots and Systems, 2006, which is hereby incorporated by reference in its entirety.

The cloud 720 provides the robot 100 with on-demand scaling of resources (e.g., computational, processing, memory, etc.) that may not otherwise be practical or cost effective on the robot 100. For example, the cloud 720 can provide scalable cloud storage 722 that scales up to a first size for storing and/or processing a relatively large amount of data 701, which may only be used for a short period of time and then discarded, and then scaled back down to a second size. Moreover, the cloud 720 can provide computer processing power for executing relatively complex computations or "brute force" algorithms that might not otherwise be possible on the robot. By displacing computer processing power and memory to a scalable cloud 720, the robot 100 can use a controller 500 having relatively less computing power and memory, thus providing a cost effective solution. Moreover, the robot 100 may execute real-time tasks (on the controller 500 or the web pad 310), such as obstacle avoidance, while passing non-real-time or non-time-sensitive tasks to the cloud 720 for processing and later retrieval.

The cloud 720 may execute one or more filters (e.g., a Bundle Adjustment, RANSAC, Expectation Maximization, SAM or other 3D structural estimation algorithms) for processing the stored image data set 703 into a 3D representation. Once processed and a dense three-dimensional map 705 has been created or updated, the image data set 703 can be discarded from the cloud storage 722, freeing up resources and allowing the cloud 720 to scale accordingly. As a result, the robot 100 needs neither the on-board storage nor the processing to handle the storage and processing of the image data set 703, due to the use of cloud based resources. The cloud 720 may return processed navigational data 701 or a map 707 (e.g., a compressed two-dimensional height map) to the robot 100, which it can then use for relatively simpler localization and navigation processing.

Additional methods and features of three-dimensional reconstruction are disclosed in "3D Models from Extended Uncalibrated Video Sequences: Addressing Key-frame Selection and Projective Drift" by J. Repko and M. Pollefeys; Fifth International Conference on three-dimensional Digital Imaging and Modeling, 2005, which is hereby incorporated by reference in its entirety.

Figure 8A:
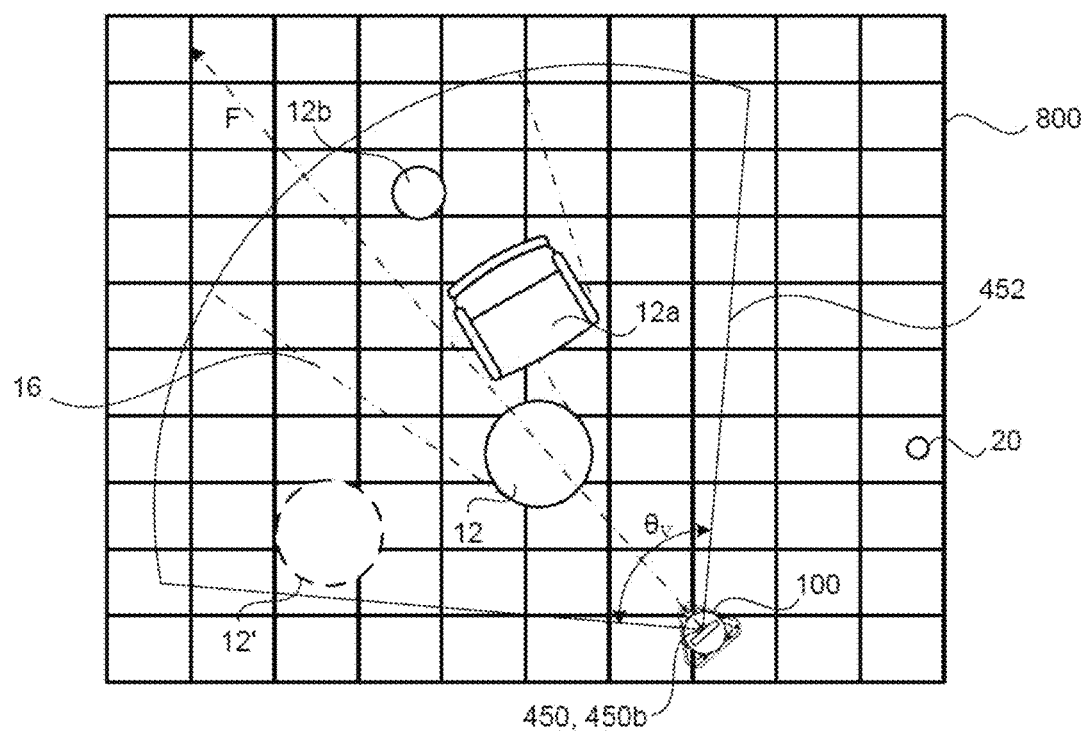
FIG. 8A is a schematic view of an example occupancy map.
Figure 8B:
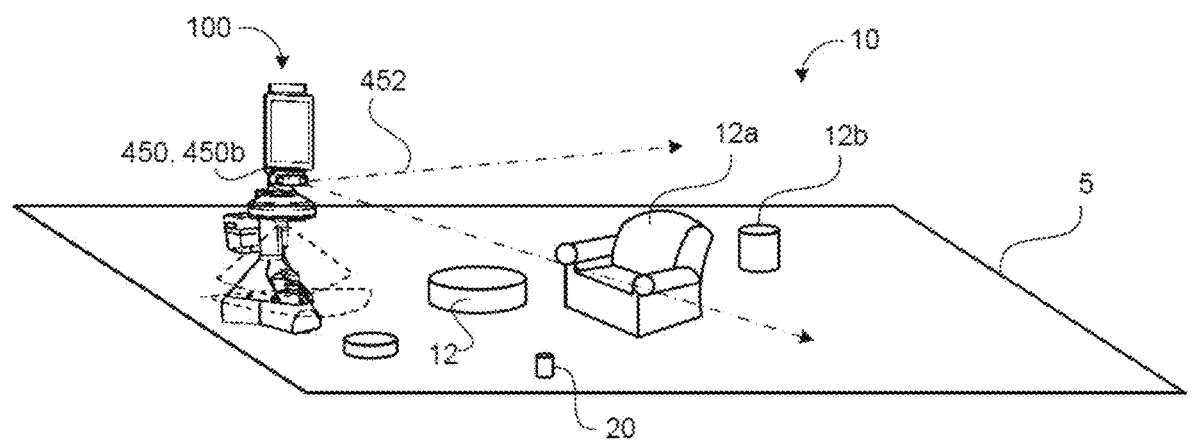
FIG. 8B is a schematic view of a telepresence robot having a field of view of a scene in a working area.

Referring to FIGS. 8A and 8B, in some circumstances, the robot 100 receives an occupancy map 800 of objects 12 in a scene 10 and/or work surface 5, or the robot controller 500 produces (and may update) the occupancy map 800 based on image data and/or image depth data received from an image sensor 450 (e.g., the second three-dimensional image sensor 450b) over time. SLAM is a technique that may be used by the robot 100 to build up an occupancy map 800 within an unknown environment or scene 10 (without a priori knowledge), or to update an occupancy map 800 within a known environment (with a priori knowledge from a given map), while at the same time keeping track of its current location.

The controller 500 may communicate the occupancy map 800 to the telepresence software application 601 for displaying a map 622 in the user interface 605. The user interface map 622 may be derived partly or wholly from the occupancy map 800. Moreover, referring also to FIG. 7, the telepresence software application 601 may receive periodic updates of the occupancy map 800 via the cloud service 720. For example, the cloud service 720 may provide with telepresence software application 601 with the dense three-dimensional map or model 705 of the scene 10 about the robot 100 and/or the simplified two-dimensional height map 707 for generating the user interface map 622. In additional examples, the cloud service 720 provides the user interface map 622 to the telepresence software application 601 based on the dense three-dimensional map or model 705 or the two-dimensional height map 707.

Referring again to FIGS. 8A and 8B, maps 800 can be used to determine a location within an environment 10 and to depict an environment for planning and navigation. The maps 800 support the assessment of actual location by recording information obtained from a form of perception and comparing it to a current set of perceptions. The benefit of a map 800 in aiding the assessment of a location increases as the precision and quality of the current perceptions decrease. Maps 800 generally represent the state at the time that the map 800 is provided or produced. This is not necessarily consistent with the state of the environment at the time the map 800 is used. Other localization techniques include monocular visual SLAM (MonoSLAM) and implementations using an extended Kalman filter (EKF) for MonoSLAM solutions.

The controller 500 may execute a scale-invariant feature transform (SIFT) to detect and describe local features in captured images. For any object 12 in an image, interesting points on the object 12 can be extracted to provide a "feature description" of the object 12. This description, extracted from a training image, can then be used to identify the object 12 when attempting to locate the object 12 in a test image containing many other objects. To perform reliable recognition, it is important that the features extracted from the training image be detectable even under changes in image scale, noise and illumination. Such points usually lie on high-contrast regions of the image, such as object edges. For object recognition and detection, the robot 100 may use a SIFT to find distinctive key points that are invariant to location, scale and rotation, and robust to affine transformations (changes in scale, rotation, shear, and position) and changes in illumination. In some implementations, the robot 100 captures multiple images (using the camera 320 and/or image sensor 450) of a scene 10 or object 12 (e.g., under different conditions, from different angles, etc.) and stores the images, such as in a matrix. The robot 100 can access the stored images to identify a new image by comparison, filter, etc. For example, SIFT features can be obtained from an input image and matched to a SIFT feature database obtained from training images (captured previously). The feature matching can be done through a Euclidean-distance based nearest neighbor approach. A Hough transform may be used to increase object identification by clustering those features that belong to the same object and reject the matches that are left out in the clustering process. A speeded up robust feature (SURF) may be a robust image detector and descriptor.

In addition to localization of the robot 100 in the scene 10 (e.g., the environment about the robot 100), the robot 100 may travel to other points in a connected space (e.g., the work surface 5) using the sensor system 400. The robot 100 may include a short range type of image sensor 450a (e.g., mounted on the underside of the torso 140, as shown in FIGS. 1 and 3) for mapping a nearby area about the robot 110 and discerning relatively close objects 12, and a long range type of image sensor 450b (e.g., mounted on the head 160, as shown in FIGS. 1 and 3) for mapping a relatively larger area about the robot 100 and discerning relatively far away objects 12. The robot 100 can use the occupancy map 800 to identify known objects 12 in the scene 10 as well as occlusions 16 (e.g., where an object 12 should or should not be, but cannot be confirmed from the current vantage point). The robot 100 can register an occlusion 16 or new object 12 in the scene 10 and attempt to circumnavigate the occlusion 16 or new object 12 to verify the location of new object 12 or any objects 12 in the occlusion 16. Moreover, using the occupancy map 800, the robot 100 can determine and track movement of an object 12 in the scene 10. For example, the image sensor 450, 450a, 450b may detect a new position of the object 12 in the scene 10 while not detecting a mapped position of the object 12 in the scene 10. The robot 100 can register the position of the old object 12 as an occlusion 16 and try to circumnavigate the occlusion 16 to verify the location of the object 12. The robot 100 may compare new image depth data with previous image depth data (e.g., the map 800) and assign a confidence level of the location of the object 12 in the scene 10. The location confidence level of objects 12 within the scene 10 can time out after a threshold period of time. The sensor system 400 can update location confidence levels of each object 12 after each imaging cycle of the sensor system 400. In some examples, a detected new occlusion 16 (e.g., a missing object 12 from the occupancy map 800) within an occlusion detection period (e.g., less than 10 seconds) may signify a "live" object 12 (e.g., a moving object 12) in the scene 10.

In some implementations, a second object 12b of interest, located behind a detected first object 12a in the scene 10, may be initially undetected as an occlusion 16 in the scene 10. An occlusion 16 can be an area in the scene 10 that is not readily detectable or viewable by the image sensor 450, 450a, 450b. In the example shown, the sensor system 400 (e.g., or a portion thereof, such as image sensor 450, 450a, 450b) of the robot 100 has a field of view 452 with a viewing angle $\theta_V$ (which can be any angle between 0 degrees and 360 degrees) to view the scene 10. In some examples, the image sensor 450 includes omni-directional optics for a 360 degree viewing angle $\theta_V$ while in other examples, the image sensor 450, 450a, 450b has a viewing angle $\theta_V$ of less than 360 degrees (e.g., between about 45 degrees and 180 degrees). In examples, where the viewing angle $\theta_V$ is less than 360 degrees, the image sensor 450, 450a, 450b (or components thereof) may rotate with respect to the robot body 110 to achieve a viewing angle $\theta_V$ of 360 degrees. In some implementations, the image sensor 450, 450a, 450b or portions thereof, can move with respect to the robot body 110 and/or drive system 200. Moreover, in order to detect the second object 12b, the robot 100 may move the image sensor 450, 450a, 450b by driving about the scene 10 in one or more directions (e.g., by translating and/or rotating on the work surface 5) to obtain a vantage point that allows detection of the second object 12b. Robot movement or independent movement of the image sensor 450, 450a, 450b, or portions thereof, may resolve monocular difficulties as well.

A confidence level may be assigned to detected locations or tracked movements of objects 12 in the working area 5. For example, upon producing or updating the occupancy map 800, the controller 500 may assign a confidence level for each object 12 on the map 800. The confidence level can be directly proportional to a probability that the object 12 is actually located in the working area 5 as indicated on the map 800. The confidence level may be determined by a number of factors, such as the number and type of sensors used to detect the object 12. For example, the contact sensor 430 may provide the highest level of confidence, as the contact sensor 430 senses actual contact with the object 12 by the robot 100. The image sensor 450 may provide a different level of confidence, which may be higher than the proximity sensor 430. Data received from more than one sensor of the sensor system 400 can be aggregated or accumulated for providing a relatively higher level of confidence over any single sensor.

Odometry is the use of data from the movement of actuators to estimate change in position over time (distance traveled). In some examples, an encoder is disposed on the drive system 200 for measuring wheel revolutions, therefore a distance traveled by the robot 100. The controller 500 may use odometry in assessing a confidence level for an object location. In some implementations, the sensor system 400 includes an odometer and/or an angular rate sensor (e.g., gyroscope or the IMU 470) for sensing a distance traveled by the robot 100. A gyroscope is a device for measuring or maintaining orientation, based on the principles of conservation of angular momentum. The controller 500 may use odometry and/or gyro signals received from the odometer and/or angular rate sensor, respectively, to determine a location of the robot 100 in a working area 5 and/or on an occupancy map 800. In some examples, the controller 500 uses dead reckoning. Dead reckoning is the process of estimating a current position based upon a previously determined position, and advancing that position based upon known or estimated speeds over elapsed time, and course. By knowing a robot location in the working area 5 (e.g., via odometry, gyroscope) as well as a sensed location of one or more objects 12 in the working area 5 (via the sensor system 400), the controller 500 can assess a relatively higher confidence level of a location or movement of an object 12 on the occupancy map 800 and in the working area 5 (versus without the use of odometry or a gyroscope).

Odometry based on wheel motion can be electrically noisy. The controller 500 may utilize scan matching in conjunction with or in place of wheel odometry. The use of scan matching may improve accuracy and/or reduce the computational burden. In such an embodiment, two partial maps obtained using LIDAR and/or other mapping methods may be merged into a single map. The two or more partial maps may be merged using a known scanning location. Alternatively, two or more partial maps may be merged using geometrical features of the partial scans. The controller 500 may receive image data from the image sensor 450 of the environment or scene 10 about the robot 100 for computing robot motion, independently of wheel based odometry of the drive system 200, through visual odometry. Visual odometry may entail using optical flow to determine the motion of the image sensor 450. The controller 500 can use the calculated motion based on imaging data of the image sensor 450 for correcting any errors in the wheel based odometry, thus allowing for improved mapping and motion control. Visual odometry may have limitations with low-texture or low-light scenes 10, if the image sensor 450 cannot track features within the captured image(s).

Other details and features on odometry and imaging systems, which may be combinable with those described herein, can be found in U.S. Pat. No. 7,158,317 (describing a "depth-of field" imaging system), and U.S. Pat. No. 7,115,849 (describing wavefront coding interference contrast imaging systems), the contents of which are hereby incorporated by reference in their entireties.

Figure 8D:
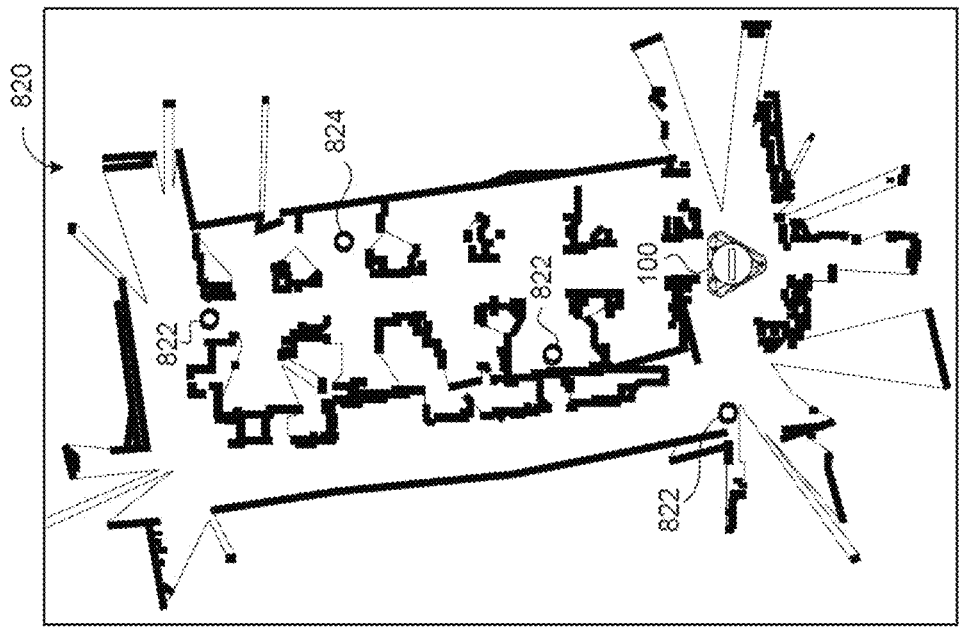
FIG. 8D is a schematic view of an example robot map corresponding to the layout map shown in FIG. 8C.
Figure 8C:
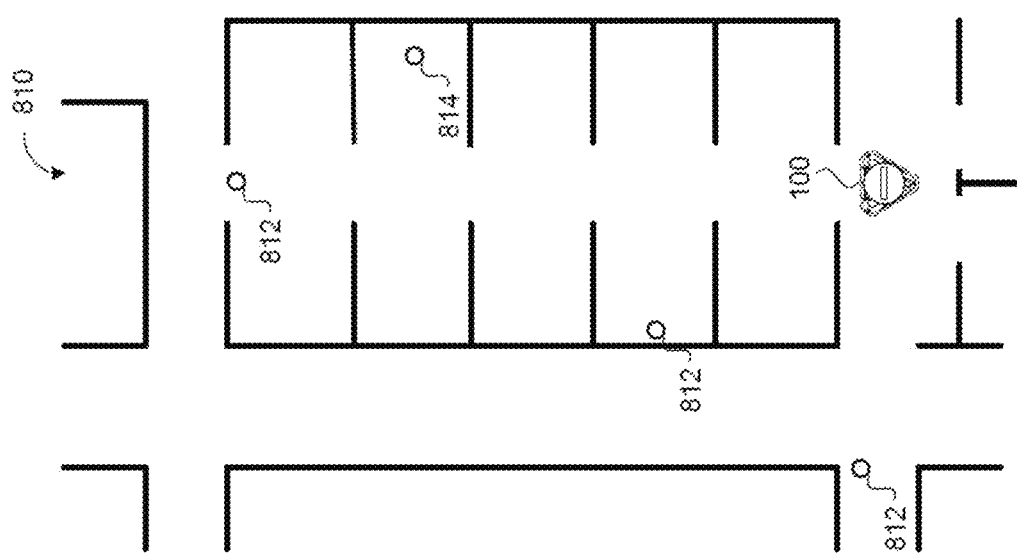
FIG. 8C is a schematic view of an example layout map.

Referring to FIGS. 8C and 8D, when a robot is new to a general geographic area or a specific building space that it will be working in, the robot may need to be shown around or provided with a map of the geographic area (e.g., a map of roadways) or building layout (e.g., room and hallway locations) for autonomous navigation. For example, on a roadway, an autonomous vehicle robot may need to know a route of streets and highways on a map to enable the robot vehicle to travel from a start location to an end location, defined by coordinates on the map. In another example, in a hospital, a telepresence robot may need to know the location of each patient room, nursing stations, etc. In some implementations, the robot 100 receives a plan view map 810, such as the one shown in FIG. 8C, and can be trained to learn the plan view map 810. For example, while leading the robot 100 around the building, the robot 100 may record specific locations corresponding to locations on the plan view map 810. The robot 100 may display the plan view map 810 on the web pad 310 and when the user takes the robot 100 to a specific location, the user can tag that location on the plan view map 810 (e.g., using a touch screen or other pointing device of the web pads 310). The user may choose to enter a label for a tagged location, like a room name or a room number.

In another example, other GPS enabled vehicles, autonomous or piloted, traveling in the same geographic area as an autonomous vehicle robot may provide detailed travel condition information actively or passively at a defined map coordinate or series of coordinates mapped to a route or portion of a route. Such information may include travel speeds along a route, predicted and actual traffic conditions, and other POI that may be shared with the autonomous map accessed by the autonomous vehicle. The shared information may generate tags at locations on the map that trigger predetermined robot functions.

At the time of tagging, the robot 100 may store the tag, with a point on the plan view map 810 and a corresponding point on a robot map 820, such as the one shown in FIG. 8D. As illustrated, the robot map 820 may be a two-dimensional plan view map similar to the plan view map 810. In alternative embodiments, the robot map 820 may be a three-dimensional map including a ground level corresponding to a two-dimensional plan view map similar to the plan view map 810.

Using the sensor system 400, the robot 100 may build the robot map 820 as it moves around. For example, the sensor system 400 can provide information on how far the robot 100 has moved and a direction of travel. The robot map 820 may include fixed obstacles in addition to the walls provided in the plan view map 810. The robot 100 may use the robot map 820 to execute autonomous navigation. In the robot map 820, the "walls" may not look perfectly straight, for example, due to detected packing crates along the wall in the corresponding hallway and/or furniture detected inside various cubicles. Moreover, rotational and resolution differences may exist between the plan view map 810 and the robot map 820.

Figure 8E:
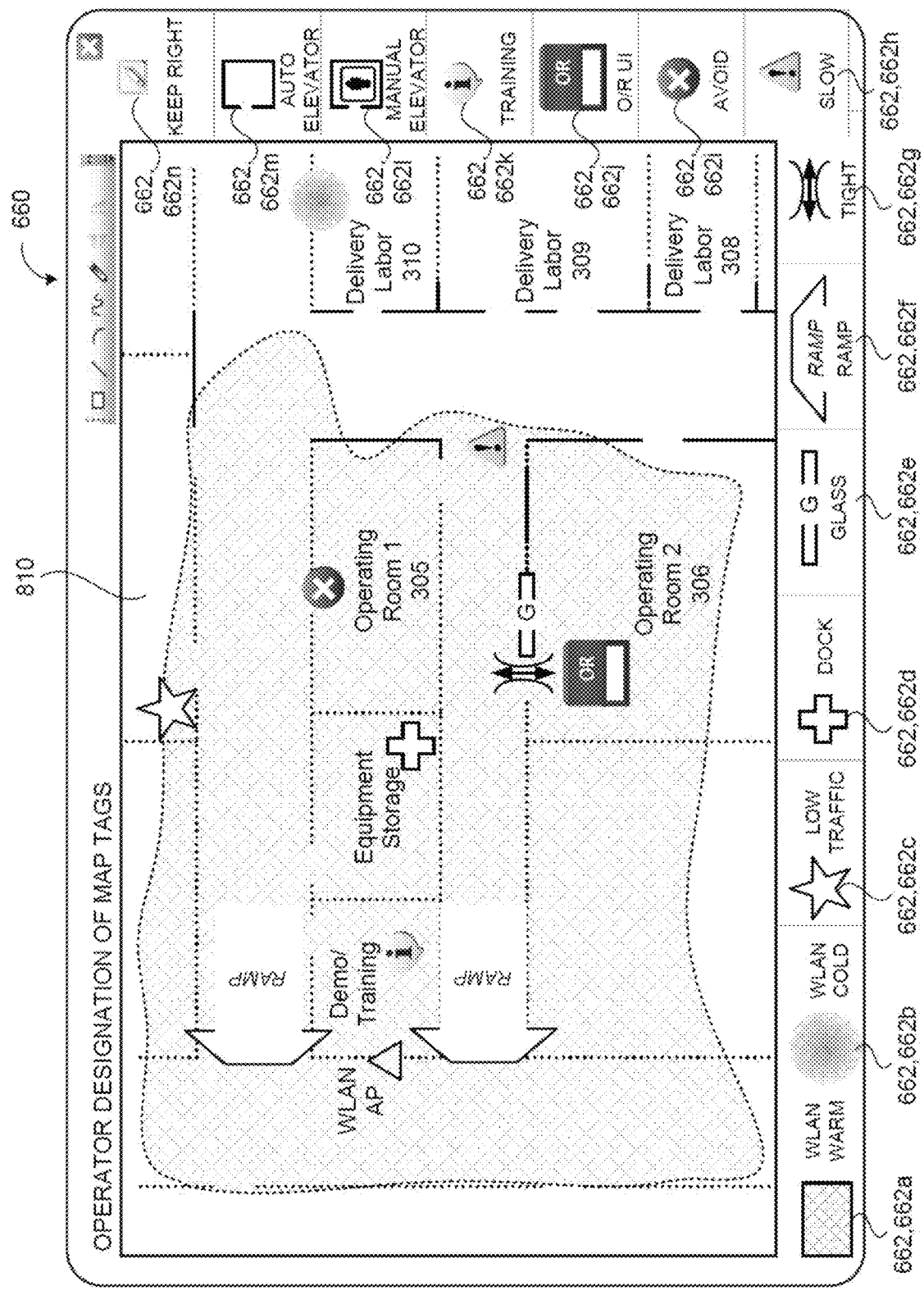
FIG. 8E provides an example arrangement of operations for operating a telepresence robot to navigate about an environment using a layout map and a robot map.

Referring to FIG. 8E, in some implementations, the telepresence software application 601 displays a tagging view 660 that allows the user to place tags 662 on the plan view map 810. The plan view map 810 may be the same map as that displayed by the plan view map window 620 or it may be a different map used internally for navigation purposes.

In the description herein, a robot refers to any autonomously driven robot having sensors, one or more processors, one or more remote communications capabilities (e.g. wifi, 4G, GPS, etc.) and mechanical drive elements. For example, in some embodiments, the term "robot" may refer to a telepresence robot such as the embodiments described above, or the term "robot" may refer to an autonomously driven, self-navigating indoor or outdoor vehicle, including partially autonomous or autonomous passenger or cargo automobiles and/or trucks. The tags and robot action-modifiers described herein apply to autonomously driven robots based at least in part on map triggers having associated robot-action modifiers (e.g., predetermined functions).

The user, a remote terminal, the robot, and/or other robots or sensors statically or dynamically occupying the same space, may insert tags 662, actively or passively, onto specific locations of the plan view map 810 and/or robot map 820 to mark map locations with information, such as driving hazards, obstacles, robot aids, etc. In one embodiment, active tag placement involves a user inserting tags on a user interface, for example the robot touch screen displaying a plan view map 810 or at a remote terminal. For example, the user may drag-and-drop tags 662 onto specific location of the plan view map 810. In various embodiments, passive tag placement on the plan view map 810 includes a remote terminal in wireless communication with sensors transmitting sensor data continuously or in defined intervals. The sensor data comprises information associated at least in part with environmental conditions (e.g., lighting conditions, traffic volume, time of day associated with high traffic volume, etc.). With regard to monitoring traffic, the sensors may monitor the special and temporal frequency of occurrences of dynamic obstacles, such as, for example, humans, vehicles, and other robots. In some embodiments, the remote terminal may employ GPS tracking of a plurality of autonomous robots occupying a single travel route or mapped area, such as the area represented by the plan view map 810. By monitoring robot speed and other conditions evaluated by onboard robot sensors, the remote terminal may create time-dependent tags indicative of travel conditions along a route. In embodiments, the remote terminal acts as a *nexus* for the plurality of robots in communication therewith such that the time-dependent tags are available to the plurality of robots. Each of the plurality of robots thereby benefits from the robot-action modifiers included in the data of the universally shared, time-dependent tags.

As is described herein, the tags may include tag coordinates associated with a point or a region, tag information defining the purpose of the tag, type of the tag, nature of the tag, instructions for the user and/or robot related to the tag, and/or other information relevant to the tag, and finally, the tag may include a tag annotation comprising a two-dimensional and/or three-dimensional graphic or text corresponding to the tag. An example of a tag annotation is an octagonal red stop sign associated with a tag containing tag information indicating an area that a robot should not enter. A tag annotation may be human and/or machine interpretable. Tag coordinates may be points, lines, planes, surfaces, volumes, and/or 2.5D or hybrid surfaces. Tags may be formed as data structures having any number of additional fields and/or parameters. For example, a tag may include fields associated with time, scheduling, spatial coordinates, and/or triggers for predetermined functions.

The term annotation, as used herein, includes text, words, or other verbal representations. Accordingly, the tag annotation may be a picture, graphical image, a pictograph, a hieroannotation, a non-verbal symbol. In addition, a tag annotation may be a word, a letter, a phrase, or other text form. For example, a tag associated with a nurse's station may include a tag annotation comprising a textual representation of the nurse's name. The textual representation of the nurse's name could be two-dimensional text, or it could be a three-dimensional text. Alternatively, the tag annotation associated with the nurse's station could be a large letter N, or a symbol representative of a nurse's station (e.g., a nurse's hat or nursing symbol).

The tags 662 may include a wireless local area network (WLAN) warm tag 662a denoting an area having relatively good signal reception and a WLAN cold tag 662b denoting an area having relatively poor signal reception. The robot 100 may use this information to navigate from one location to another through an area having relatively good wireless signal reception, while avoiding areas having relatively poor wireless signal reception.

A low traffic tag 662c denotes an area having relatively low traffic (person and/or robot). The robot 100 may select a travel path through an area having a relatively low traffic volume, rather than through an area having a relatively high traffic volume. Moreover, if the robot 100 must travel through a high traffic area, the robot 100 may execute one or more specific object detection obstacle avoidance (ODOA) behaviors to navigate the area successfully without collisions.

A dock tag 662d denotes a location of a robot docking station. A low battery event may signal the controller 500 to seek recharging. The robot 100 may use the map location tagged with a dock tag 662d to locate a robot docking station for recharging. For example, by applying a resolved distortion between the plan view map 810 and the robot map 820 (FIGS. 8C and 8D), the robot 100 can determine a corresponding robot map location 824 corresponding to the tagged layout map location 814 to navigate to that tagged location to dock with a robot docking station. Resolving the distortion may include determining a distortion between two maps that use the same coordinate system. The robot map 820 and the plan view map 810 may both be two-dimensional and as such, determining a distortion may not require determining a coordinate transformation between different dimensions.

Some tags 662 may be used to indicate obstacles or special traversal areas. For example, a glass tag 662e indicates the location of a glass wall, window, or door. The robot 100 may use this information to avoid the tagged glass structures, since infrared proximity sensors may not detect them. A ramp tag 662f indicates the location of a floor ramp. For a distance, the robot 100 may detect the ramp as an obstacle, since it may appear to have a vertical height greater than a threshold traversal height. When approaching a tagged ramp, the robot 100 may execute a ramp or traversal behavior to successfully negotiate the ramp. A tight tag 662g indicates the location of a relatively narrow corridor or throughway. The robot 100 may avoid such areas, so as to avoid any confining situations.

A slow tag 662h indicates a location or area in which the robot 100 drives relatively slowly. This location or area may coincide with a high traffic area. An avoid tag 662i denotes a location or area that the robot 100 should avoid (i.e., not drive through). In some embodiments, an avoid tag 622i may be operation mode-dependent. For example, the avoid tag 622i may be applicable only when the robot is operating in a fully autonomous mode. During teleoperation, the avoid tag 622i may be effectively ignored by the robot.

In other embodiments, the avoid tag 622i may include time-dependent navigation information. For example, the data structure for an avoid tag may include a cost field associated with a time period (e.g., a time of day interval, a point in time, etc.). The cost field may include data that represents a relative cost of navigation through an area associated with the avoid tag during the time period. A relatively high cost value may indicate that navigation through the area is relatively difficult during that time period and should be avoided if possible. In determining navigation routes, the robot or a remote processor may generate multiple potential navigation paths and calculate a total cost (or ranking score) for each potential navigation path based on the time-dependent navigation information in avoid tags along the path. The robot or remote processor may then determine a navigation path based on the path that has the relatively lower overall cost value during the navigation time period, i.e., relatively more favorable ranking score during the navigation time period.

In one embodiment, the time-dependent navigation information may be input by the user in the process of inserting a tag on the plan view map 810 and/or robot map 820. In other embodiments, the time-dependent information may be associated with a newly instantiated tag or appended to an existing tag based on information gathered by a robot during navigation. For example, a robot traveling down a hallway may have its sensors "blinded" by sunlight coming through windows during a particular time of day. An infrared proximity sensor, for example, will fail if the receiver is flooded with light. The robot may note the time of day in the time-dependent information associated with a tag and associate a high cost with the time dependent tag if the conditions associated with the time-dependent tag interfere with travel. Subsequently, the robot 100, and any other robot navigating the same space and receiving the time-dependent tag at coordinates on their own map or a universally accessible and shared map, will avoid navigating the route identified by the tag coordinates at the particular time of day. For example, a robot 100 travelling a route that floods with sunlight at a halfway point in the route at an approaching point in time will avoid traveling that route and will divert to an alternate route or alternate portion of a route that has a lower associated cost (i.e., more favorable ranking). The robot 100 thus avoids sunlight flooding the navigation path and disabling sensors associated with effective and safe (i.e., collision free) navigation at a certain day and time at the identified location.

Additionally, occupancy sensors may be used to insert a tag on a map in response to sensed environmental conditions and thereby associate time-dependence with a reactive override, or robot-action modifier. Such sensors may include at least some or all of the following sensor types, either alone or in combination: Passive Infrared (PIR) sensors, RF disturbance sensors, Internet enabled sensor nodes, stationary sensors such as wall-mounted digital cameras or video cameras transmitting wirelessly and/or through wired transmission cables, mobile sensors embedded in worn employee badges, IMU-located sensors, IMU, accelerometer, GPS and/or Internet enabled mobile phones, sensors on one or more autonomous robots sharing the mapped area, and sensors incorporated in or in remote communication with robots such as InTouch Health®'s RP-Lite®, RP-Vantage®, and RP-xpress®.

For example, a potential navigation path may have a high cost (relatively low ranking/unfavorable ranking score among all potential navigation paths) if occupancy sensors in a particular area communicate data indicative of a high volume of traffic at one or more coordinate points along that navigation path which would make autonomous robot navigation difficult, inefficient, or impossible along some or all of that navigation path. In response to such time-dependent data, the robot 100 will elect a relatively more favorable navigation path having fewer indications of traffic instances and/or traffic volume.

The robot 100, and/or a remote processing terminal in communication with the robot and a plurality of sensors, communicates with the plurality of stationary and/or affixed environmental monitoring sensors. In embodiments, the robot 100 and/or remote processing terminal (which is, in embodiments, a central hub communicating remotely with a plurality of robots 100) respond in real time to sensor output by modifying behavior, for example by selecting an alternate navigation path with a more favorable ranking (lower associated cost value) enabling a more efficient and effective traversal of a travel route. In other embodiments, the robot 100 and/or remote terminal in communication with the robot 100 densely maps tags associating time-dependence to various environmental and traffic volume conditions. The tags have associated robot action modifiers for execution by the robot 100 in response to those tags at the associated point in time or associated time period. In embodiments, tag icons on a map change in appearance in accordance with their time dependence.

An operating room user interface (OR UI) tag 662j indicates the location or area of a hospital operating room. The robot 100 may use this tag to find the operating room to provide telepresence support and/or to display a specific user interface (e.g., an OR UI) upon entering the OR area. A training tag 662k can be used to mark general locations, such as hallways and rooms, to train the robot 100 to learn its environment 10.

A manual elevator tag 662l indicates the location of an elevator where the robot 100 should allow a user to aid the robot's traversal into/out of the elevator. Manual elevator negotiation may be based on remote user piloting or robot-local user guidance. For remote user piloting, a remote user provides drive commands to the robot 100 (e.g., using a joystick). For robot-local user guidance, a person adjacent to the robot 100 may physically touch the robot 100 and, in response to those touches, the robot 100 moves accordingly. Features regarding robot responsiveness to user touching combinable with those described herein can be found in application Ser. No. 13/032,390, filed on Feb. 22, 2011, which is hereby incorporated by reference in its entirety.

An auto elevator tag 662m indicates the location of an elevator that the robot 100 may negotiate (into and out of) autonomously. The robot 100 may execute a threshold traversal behavior 512d (FIG. 5) to enter into and drive out of the elevator, so as to avoid tipping. Features regarding robot responsiveness to user touching combinable with those described herein can be found in application serial number PCT/US11/59910, filed on Nov. 9, 2011, which is hereby incorporated by reference in its entirety.

A keep right tag 662n indicates a map location or area in which the robot 100 should keep to the right. A user may place this tag along certain corridors, such as high traffic corridors. In response to the keep right tag 662n, the robot 100 may execute a wall following behavior to stay along the wall while driving in the tagged area.

After map training, when a user wants to send the robot 100 to a location, the user can either refer to a label/tag 622 (e.g., enter a label or tag into a location text box displayed on the web pad 310) or the robot 100 can display the plan view map 810 to the user on the web pad 310 and the user may select the location on the plan view map 810. If the user selects a tagged layout map location 814, the robot 100 can easily determine the corresponding robot map location 824 on the robot map 820 and can proceed to navigate to the selected location 814.

In some implementations, the robot controller 500 may execute a first behavior 512 while maneuvering about a first area and then execute a second behavior 512 while maneuvering about a second area associated with a tag having an associated robot behavior modifier. For example, while executing a person follow behavior 512b, the robot controller may either cease execution of that behavior 512b or concurrently execute a threshold traversal behavior 512d upon reaching a map location 814 tagged with a ramp tag 662f or an auto elevator tag 622m.

If the selected location on the plan view map 810 is not a tagged location 814, the robot 100 determines a corresponding location 824 on the robot map 820. In some implementations, the robot 100 computes a scaling size, origin mapping, and rotation between the plan view map 810 and the robot map 820 using existing tagged locations, and then applies the computed parameters to determine the robot map location (e.g., using an affine transformation or coordinates).

The robot map 820 may not be the same orientation and scale as the plan view map 810. Moreover, the layout map may not be to scale and may have distortions that vary by map area. For example, a plan view map 810 created by scanning a fire evacuation map typically seen in hotels, offices, and hospitals is usually not drawn to scale and can even have different scales in different regions of the map. The robot map 820 may have its own errors. For example, locations on the robot map 820 may have been computed by counting wheel turns as a measure of distance, and if the floor was slightly slippery or turning around corners caused extra wheel turns, inaccurate rotation calculations may cause the robot 100 to determine inaccurate locations of mapped objects.

A method of mapping a given point 814 on the plan view map 810 to a corresponding point 824 on the robot map 820 may include using existing tagged points 812 to compute a local distortion (in the same two-dimensional coordinate system) between the plan view map 810 and the robot map 820 in a region (e.g., within a threshold radius) containing the layout map point. The method further includes applying a distortion calculation to the layout map point 814 in order to find a corresponding robot map point 824. The reverse can be done if you are starting with a given point on the robot map 820 and want to find a corresponding point on the plan view map 810, for example, for asking the robot for its current location.

Any of a wide variety of tag schemas and data structures may be used. Tags are a collection of information and the data comprising a tag can be distributed in different data tables. For example, tags may contain attributes in the form of key-value pairs that specify a purpose of the tag, tag parameters, and tag attributes (generally "tag information"). Table 1 below provides a specific example.

TABLE 1

| Field name | Data type | Description |
| --- | --- | --- |
| tagId | integer | the ID of the tag entry in the tag table described above |
| name | text | the parameter name |
| value | text | the parameter value |

Tags associated with regions may have attributes associated with them that specify their purpose and specify parameters that influence behaviors associated with the region. These key-value pairs may be stored using a data structure similar to the example in Table 2 below:

TABLE 2

| Field name | Data type | Description |
| --- | --- | --- |
| regionId | integer | the ID of the region entry in the region table described above |
| name | text | the parameter name |
| value | text | the parameter value |

The data structure for each tag may include tag coordinates and tag information, which may include a tag annotation (such as a two-dimensional and/or three-dimensional graphical representation of the tag). Table 3 below provides a specific example of a data structure for a tag.

TABLE 3

| Field name | Data type | Description |
| --- | --- | --- |
| id | integer | globally unique identifier for the tag in the database |
| mapId | integer | the identifier of the robot map to which the tag belongs |
| timestamp | float | a timestamp representing when the tag was created |
| poseX | float | the X coordinate of the tag in the robot map's coordinate system |
| poseY | float | the Y coordinate of the tag in the robot map's coordinate system |
| poseZ | float | the Z coordinate of the tag in the robot map's coordinate system |
| poseXr | float | the tag's rotation about the X axis |
| poseYr | float | the tag's rotation about the Y axis |
| poseZr | float | the tag's rotation about the Z axis |
| name | text | a human-readable identifier for the tag |
| annotation | image | a 2D and/or 3D graphical representation |

As described herein, a tag may be associated with a region, rather than a specific point, on a map. There may be a many-to-one relationship between tag information and a tag. A specific example of a data structure for a tag associated with a region is provided below in Table 4A.

TABLE 4A

| Field name | Data type | Description |
| --- | --- | --- |
| id | integer | globally unique identifier for the region in the database |
| mapId | integer | the identifier of the robot map to which the region belongs |
| timestamp | float | a timestamp representing when the region was created |
| poseX | float | the X coordinate of the region's centroid in the same coordinate system as the robot map |
| poseY | float | the Y coordinate of the region's centroid in the same coordinate system as the robot map |
| poseZ | float | the Z coordinate of the region's centroid in the same coordinate system as the robot map |
| poseXr | float | the region's rotation about the X axis |
| poseYr | float | the region's rotation about the Y axis |
| poseZr | float | the region's rotation about the Z axis |
| name | text | a human-readable identifier for the region |
| annotation | image | a 2D and/or 3D graphical representation |

In some examples, the tag or region may be time-dependent, such that path navigation is altered by the time-dependent action modifiers. These may be pre-planned, scheduled action modifiers for time-dependent navigation of the robot. A specific example of a data structure for a tag or region associated with a schedule of action modifiers is provided below in Table 4B.

TABLE 4B

| Field name | Data type | Description |
| --- | --- | --- |
| id | integer | globally unique identifier for the tag or region in the database |
| Timedep | Flag | Boolean representing whether the tag or region is time-dependent or not. |
| MonSchedule | Array | Array of actions and associated times for those actions on Monday |
| TueSchedule | Array | Array of actions and associated times for those actions on Tuesday |
| WedSchedule | Array | Array of actions and associated times for those actions on Wednesday |
| ThuSchedule | Array | Array of actions and associated times for those actions on Thursday |
| FriSchedule | Array | Array of actions and associated times for those actions on Friday |
| SatSchedule | Array | Array of actions and associated times for those actions on Saturday |
| SunSchedule | Array | Array of actions and associated times for those actions on Sunday |

An array of scheduled actions may be, for example, an optionally concatenated array of "Code, time" combinations such as "33, 800, 0, 1700" associated with Wednesdays, where "33" is a identifier for an action modifier instructing the robot to "go slow" in a location at peak traffic hours, e.g., 8 am ("800" hours) and to change from the "go slow" code at 5 pm ("1700" hours), to a default pace of travel represented by "0". Concatenating code combinations allows for multiple robot action modifiers to be coded sequentially with a triggering time, and for a null code to deactivate any robot action modifier at another time. Although the example schedule in Table 4A is a weekly schedule of action modifiers, the time dependent tags may include action modifiers associated with any schedule such as, for example, hourly, bi-weekly, monthly, specific calendar date-associated and annual schedules.

In some examples, the geometry of regions may be broken into the components of their centroid and offsets from the centroid to allow for the position and rotation of many objects to be updated quickly. When CPU resources permit, the bounding box of the final coordinates (the polygon points relative to the centroid, transformed by the centroid's pose into the map's coordinate system) can be indexed using an R*-tree or similar data structure for fast lookup based on geometric constraints. The points comprising the region's polygon may be stored in clockwise (or counter-clockwise) order to facilitate point-in-polygon tests based on ray-tracing algorithms.

As an example, a tag indicating a region that is a slow zone may have a data structure as provided below in Table 5.

| Name | Value |
| --- | --- |
| type | speedZone |
| subtype | explicit |
| maxXVelocity | 0.75 |
| maxYVelocity | 0.0 |
| maxThetaVelocity | 0.75 |

Table 5 illustrates an example of a slow-zone tag in which the speed limits are explicitly set based on values associated with the region itself. Alternatively, a region may be defined in such a manner that a robot may interpret the region as a slow zone. For example, in Table 6 below, a robot may interpret a region defined as an intersection as a slow zone and reduce its speed to a predetermined velocity.

TABLE 6

| Name | Value |
|------|-------|
| type | speedZone |
| subtype | intersection |

Tags associated with points or regions on a map may include tag coordinates, tag information, and tag annotations of any of a wide variety. Additionally, the tags may be implemented using any of a wide variety of data types, including those illustrated above in Tables 1-6. The terms tag information and tag annotation are referred herein as separate elements. However, according to various embodiments, a tag annotation may be a part of the tag information. Specifically, a data structure may or may not include a distinct field for the tag annotation. Rather, a field in the data structure for the tag information may incorporate the tag annotation.

Figure 8F:
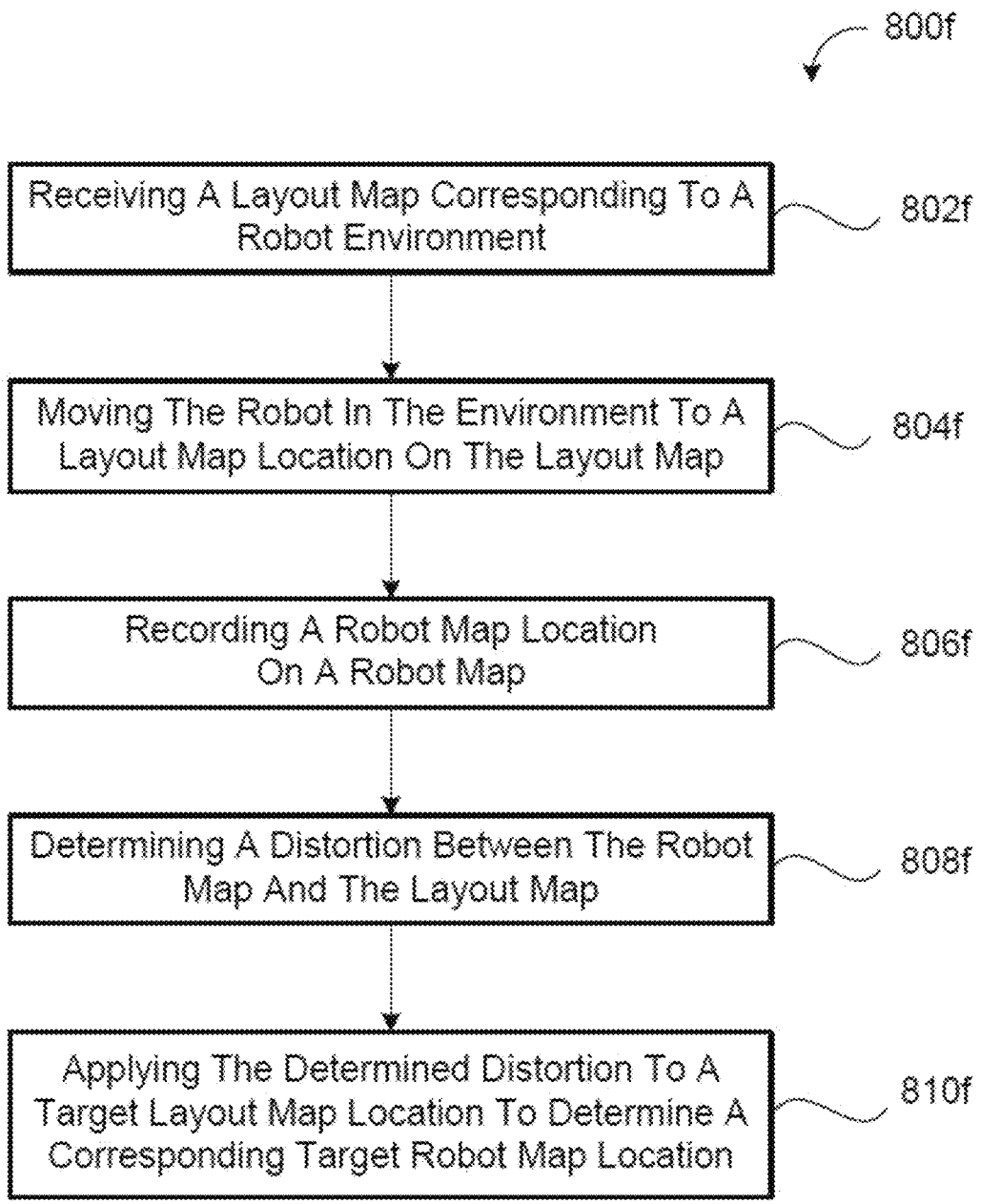
FIG. 8F illustrates a method for using a robot location and perspective to determine a distortion between a video feed and a plan view map.

FIG. 8F provides an example arrangement 800f of operations for operating the robot 100 to navigate about an environment using the plan view map 810 and the robot map 820. The operations include receiving 802f a plan view map 810 corresponding to an environment of the robot 100, moving 804f the robot 100 in the environment to a layout map location 812 on the plan view map 810, recording 806f a robot map location 822 on a robot map 820 corresponding to the environment and produced by the robot 100, determining 808f a distortion (two-dimensional) between the robot map 820 and the plan view map 810 using the recorded robot map locations 822 and the corresponding layout map locations 812, and applying 810f the determined distortion to a target layout map location 814 to determine a corresponding target robot map location 824, thus allowing the robot to navigate to the selected location 814 on the plan view map 810. In some implementations, the operations include determining a scaling size, origin mapping, and rotation between the plan view map 810 and the robot map 820 using existing tagged locations and resolving a robot map location corresponding to the selected target layout map location 814. The operations may include applying an affine transformation to the determined scaling size, origin mapping, and rotation to resolve the robot map location. Any of the above operations may be repeated any number of times in order to increase accuracy and/or efficiency. For example, moving 804f the robot 100 in the environment and recording 806f a robot map location may be repeated multiple times in order to gather sufficient correlation points for the subsequent transformations and calculations between the layout map and the robot map.

Other details and features combinable herewith can be found in PCT application Serial No.: PCT/US11/60935, filed on Nov. 16, 2011, which is hereby incorporated by reference in its entirety.

Figure 9A:
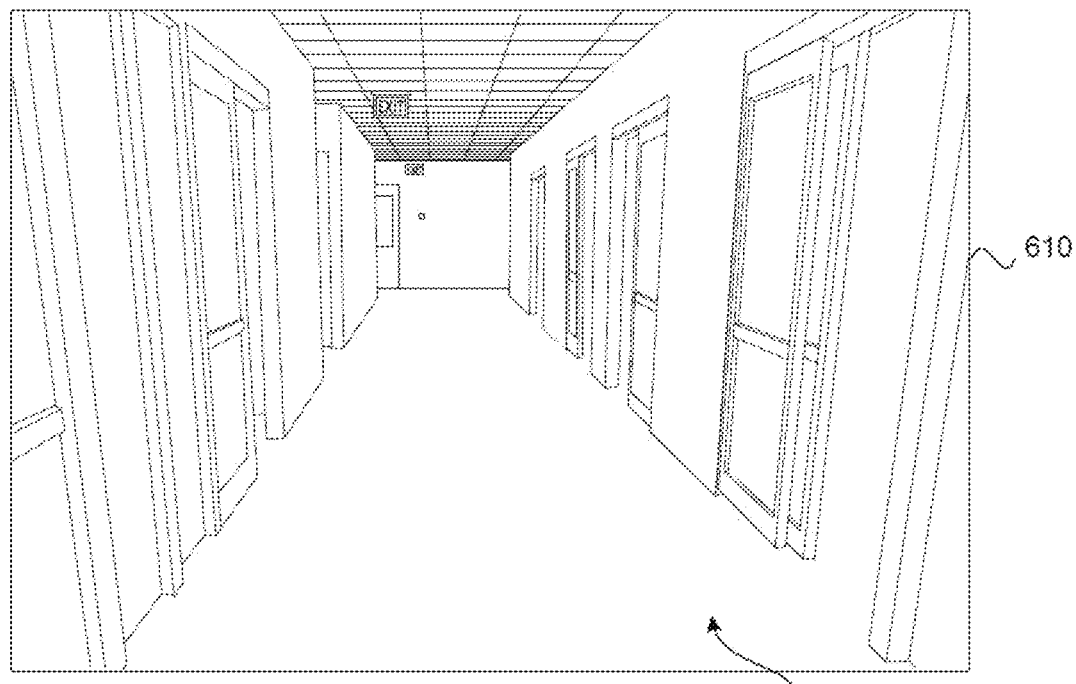
FIG. 9A is schematic view of an example remote video view from a robot positioned in a hallway.
Figure 9B:
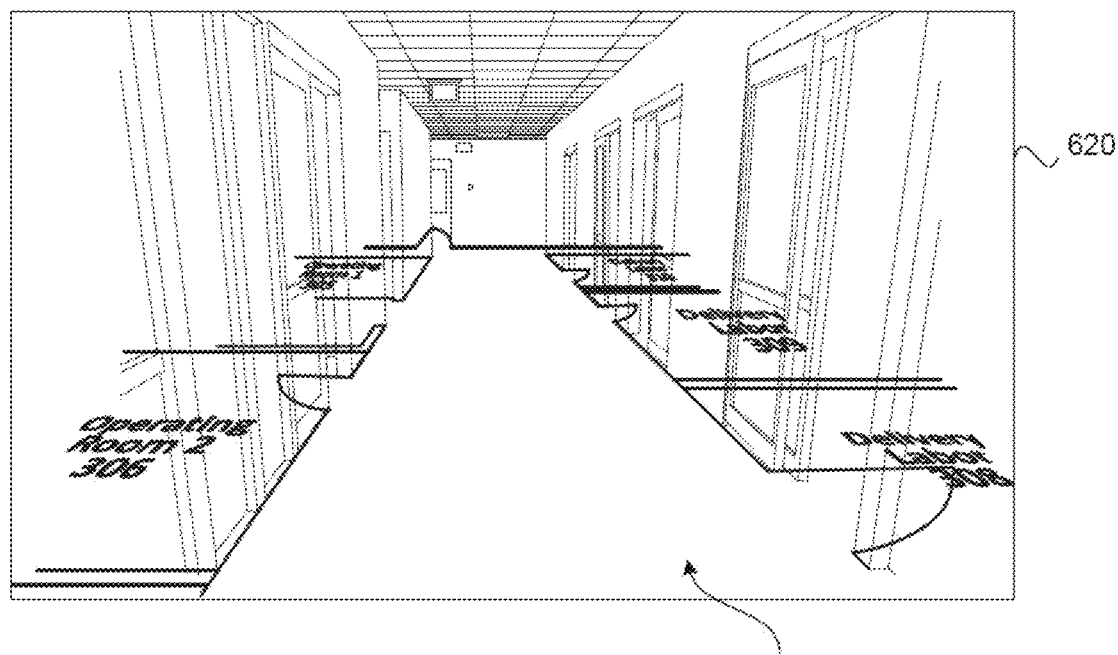
FIG. 9B is a schematic view of an example hybrid map incorporating the remote video view shown in FIG. 9A, together with a map indicating room numbers.

Referring to FIGS. 9A and 9B, in some implementations, the teleoperation software application 601 displays a hybrid three-dimensional image map 622b (hybrid map) in the map window 620. The hybrid map 622b may be a combination of the remote view 612 displayed in the remote video feed window 610 and a plan view map 810, such as the two-dimensional, top-down map 622a displayed in the plan view map window 620 (FIG. 6D). FIG. 9A illustrates a remote video view 612 that a user may see when the robot 100 is positioned in a hallway. FIG. 9B illustrates a hybrid map 622b in which the plan view map 810 is partially overlaid and modified to fit the remote view 612, indicating the room numbers and/or room types of the areas in the field of view of the robot 100. When viewing a live video feed, the user may place the cursor over the window and start moving the scroll wheel upward. During the transitional process, the perspective video view (from the camera 320 on the robot 100) is progressively transitioned between the remote video view 612 and the map 622. The map 622 is fully warped at the start of the transition to map the perspective remote video view 612, and gradually reverts to its unwarped view at the end of the transition. So if the mouse wheel is 30% up, then the user sees a dissolved image which contains 70% video and 30% map, and the video portion is 30% de-warped, while the map is 70% warped. This implementation allows for a single view to fluidly represent both a perspective live remote video view 612 and a map 622.

To provide the hybrid map 622b, the teleoperation software application 601 may determine a distortion (between two-dimensional coordinates and three-dimensional coordinates) between the remote view 612 and the plan view map 810 using recorded robot map locations 822 of a robot map 820 and corresponding layout map locations 812 and then applying the determined distortion to fit the plan view map 810 to the remote view 612. In some implementations, determining the distortion includes determining a scaling size, origin mapping, and rotation between the plan view map 810 and the remote view 612, for example, by applying an affine transformation to the determined scaling size, origin mapping, and rotation. Determining a distortion between a two-dimensional plan view map and a three-dimensional video feed may include determining a coordinate transformation between the disparate coordinate systems.

Referring to FIGS. 6D and 10A-10E, in some implementations, the user interface 605 provides a look-ahead command 624 that causes the display of a rendered look-ahead view 612a in the map window 620, a dedicated separate window, or some other window. While driving the robot 100, the user may invoke a look-ahead command 624, which causes the robot 100 to stop moving physically, while the teleoperation software application 601 generates and displays a rendered look-ahead view 612a providing a perspective view of a proposed robot drive path as if the robot 100 were continuing to move along its drive path. This may be accomplished by using the map data, such as location of walls, and constructing a perspective "virtual reality" view based on the virtual location of the robot 100. For example, the telepresence software application 601 may use the plan view map 810, the robot map 820, and/or stored image data 701 (FIG. 7) to construct the look-ahead view 612a. For robot systems using a cloud computing service 720, such as the example shown in FIG. 7, the telepresence software application 601 and optionally the robot 100 may communicate with the cloud computing service 720, which may construct the look-ahead view 612a based on stored image data 701, the three-dimensional map 705, and/or the two-dimensional height map 707 (or alternatively a 2.5D hybrid map) and then provide the look-ahead view 612a for rendering in the map window 620. This implementation allows the telepresence software application 601 to leverage the scalable computer processing and data storage capability of the cloud service (e.g., the cloud service 720 can elastically scale up to process the data and then scale down afterwards), thus reducing a processing and memory requirement for a computing device executing the telepresence software application 601.

Figure 10A:
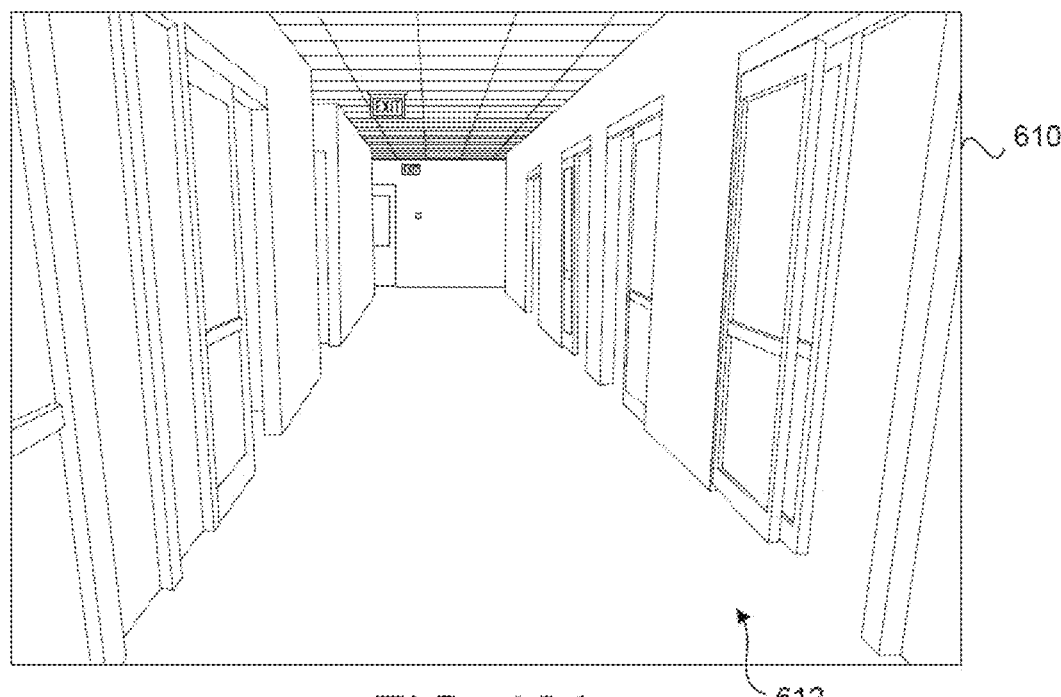
FIG. 10A provides an example remote view of a remote video window of a telepresence software application.
Figure 10B:
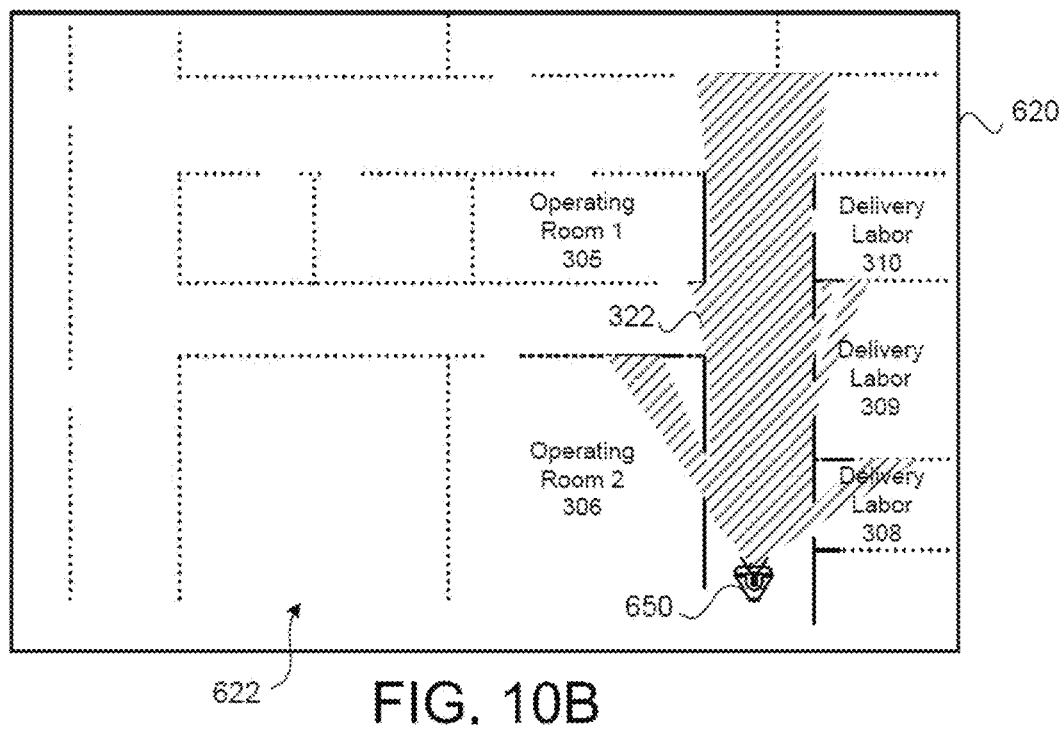
FIG. 10B is a schematic view of an example map of the area shown by the remove view of FIG. 10A.
Figure 10C:
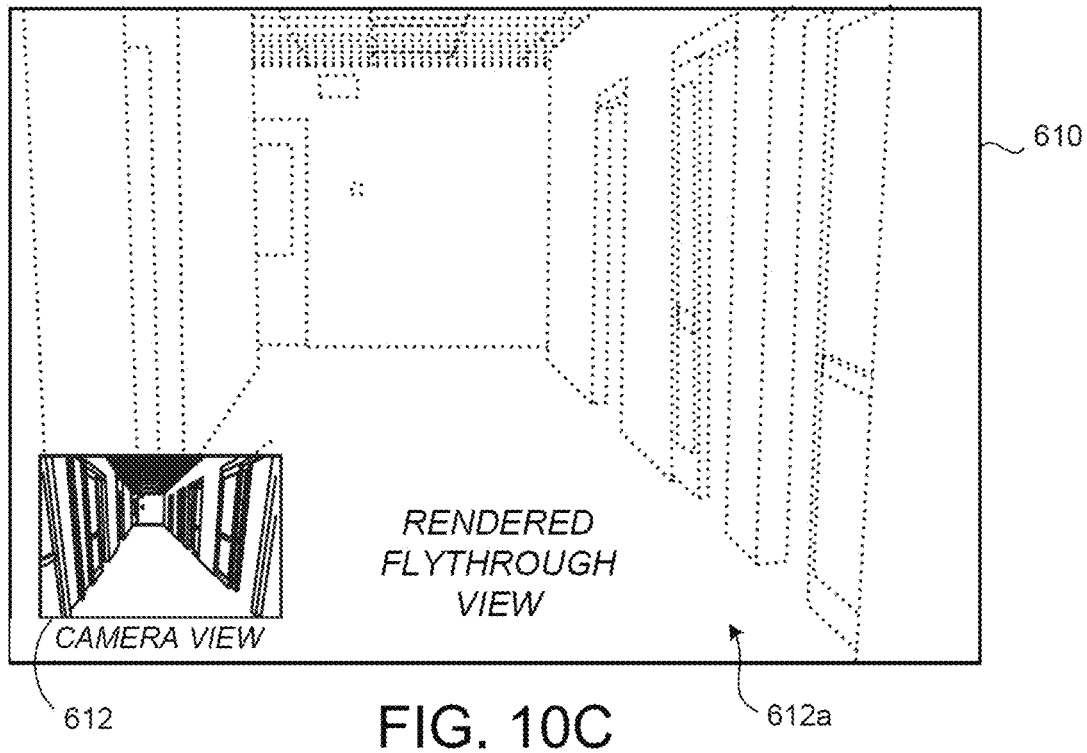
FIG. 10C is a schematic view of an example look-ahead view of a telepresence software application.
Figure 10D:
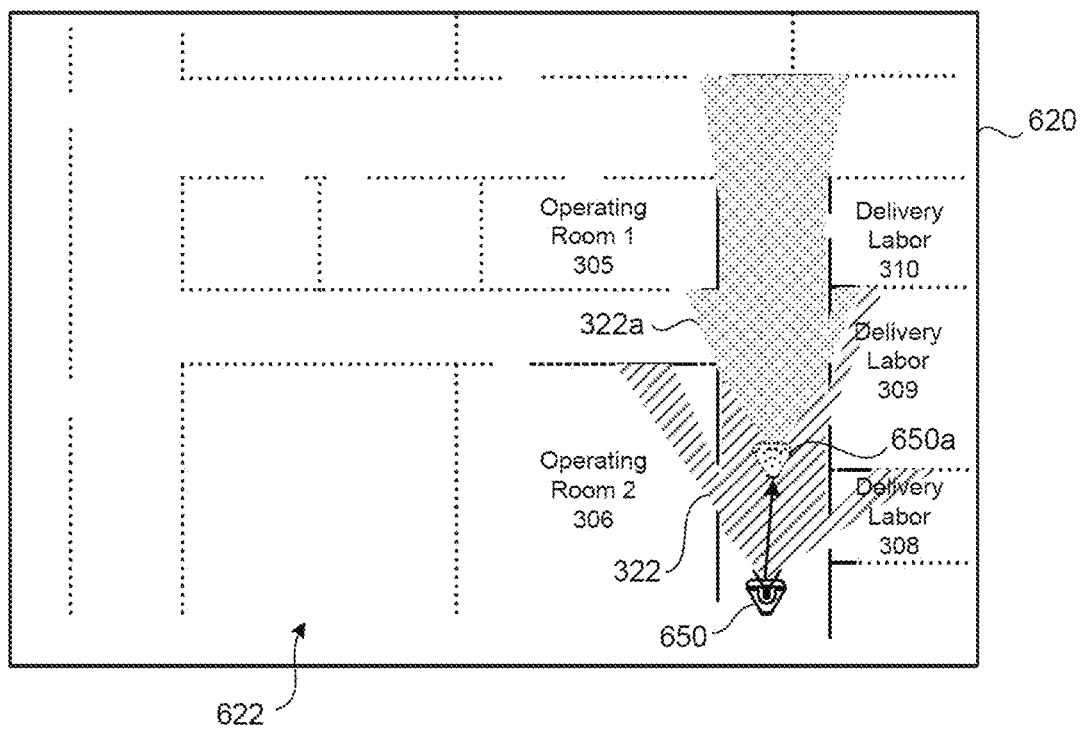
FIG. 10D is a schematic view of the map shown in FIG. 10B with a robot icon and a corresponding camera field of view.
Figure 10E:
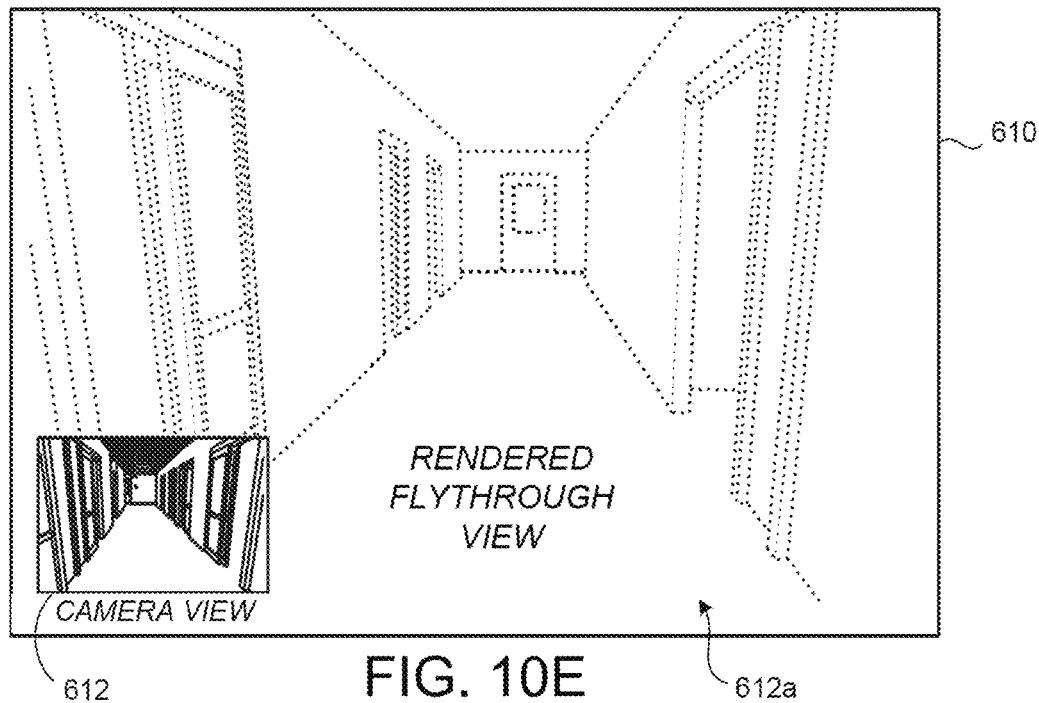
FIG. 10E is a schematic view of an example look-ahead view of a telepresence software application.
Figure 10F:
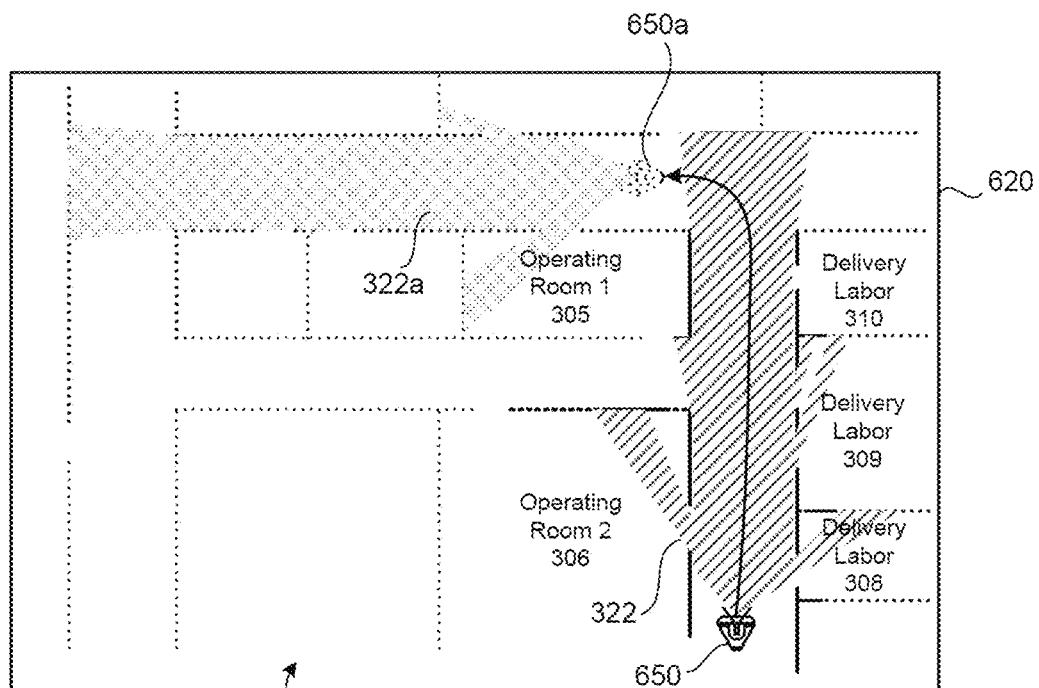
FIG. 10F is a schematic view of the map shown in FIG. 10B with a robot icon and a corresponding camera field of view.

FIG. 10A illustrates an example remote view 612 of the remote video feed window 610 of the telepresence software application 601. FIG. 10B illustrates a complementary map 622 displayed in the map window 620. The map 622 provides the current location of the robot 100 as denoted by the robot icon 650 along with a camera field of view 322 for a robot camera 320. FIGS. 10C and 10E provide example look-ahead views 612a displayed in the remote video feed window 610. The remote video feed window 610 may continue to display the remote view 612 from the robot camera 320 in a picture-in-picture window, for example, placed in a corner of the remote video feed window 610. FIGS. 10D and 10F provide example maps 622 displayed in the map window 620. While executing the look-ahead command, the telepresence software application 601 may render the robot icon 650 at the robot's current location along with the robot's camera field of view 322. In addition or alternatively, the telepresence software application 601 may render in the plan view map window 620 a virtual robot icon 650a moving along a look-ahead path along with a projected look-ahead camera field of view 322a.

In some implementations, as the user drives the robot 100 along a corridor using a joystick in communication with the telepresence software application 601, the user may invoke the look-ahead command 624 (e.g., by selecting a corresponding button on the user interface 605 or the joystick). For example, at a location 50 feet away from a turn in the corridor, the user may invoke the look-ahead command 624, causing the generation of a look-ahead view 612a and stopping further movement of the robot 100 along the corridor. The user may continue, however, to virtually move the robot 100 in a look-ahead mode. The user interface 605 may display the look-ahead view 612a (e.g., a three-dimensional model) of the same corridor at the same position. As the user drives forward in the look-ahead mode, continues 50 feet, turns left, and continues driving, the user can see the location of rooms and other corridors along the way in the three-dimensional model/look-ahead view 612a. In some examples, for the first 30 feet of "virtual" driving, the telepresence software application 601 may display a blend of the actual view (from the stationary physical robot, further magnified and perspective-warped to match the virtual location) and the three-dimensional model/look-ahead view 612a.

Figure 10G:
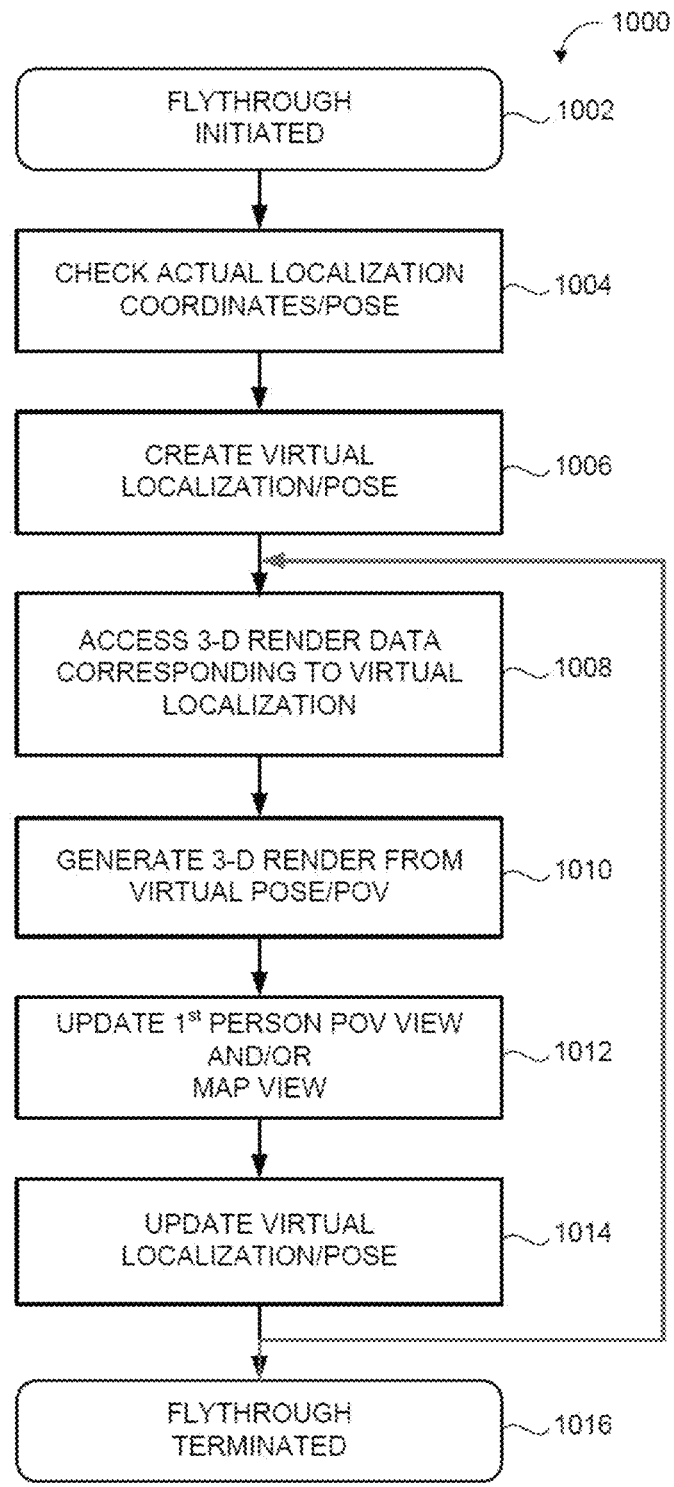
FIG. 10G provides an example arrangement of operations for a look-ahead routine of a telepresence software application.

FIG. 10G provides an example arrangement 1000 of operations for executing a look-ahead mode of the telepresence software application 601. The operations include initiating 1002 the look-ahead mode (also referred to as the flythrough mode) and checking 1004 an actual localization of the robot 100, such as a current pose and/or coordinates of the robot 100. The robot 100 may determine its localization based on received sensor signals of its sensor system 400 and then forward the localization to the telepresence software application 601 and/or a cloud computing service 720. The operations further include creating 1006 a virtual localization and/or pose of the robot 100. The telepresence software application 601 or the cloud computing service 720 may use a dynamics model 570 (FIG. 5) associated with the robot 100 and image data 701 (FIG. 7) (e.g., volumetric point cloud image data) to generate the virtual localization and/or pose. The operations may include accessing 1008 three-dimensional rendering data corresponding to the determined virtual robot localization and generating 1010 a three-dimensional rendering of the robot 100 and/or local environment about the robot 100. This may entail accessing image data 701 (e.g., volumetric point cloud image data) and/or the three-dimensional map 705 stored locally or remotely in cloud storage 722 to construct the local three-dimensional model/look-ahead view 612a, which may be displayed by the telepresence software application 601 in the remote video feed window 610. Moreover, this may entail generating a three-dimensional model of the robot 100 illustrated by the virtual robot icon 650a and the projected look-ahead camera field of view 322a in the map window 620. The operations may include updating 1012 the displayed look-ahead view 612a or a first person point of view (POV) and updating a virtual localization/pose of the robot 100 as the robot 100 virtually maneuvers about in the look-ahead mode. Steps 1008-1014 can be repeated (e.g., on a periodic basis) until terminating 1016 the look-ahead/ flythrough mode.

Figure 11A:
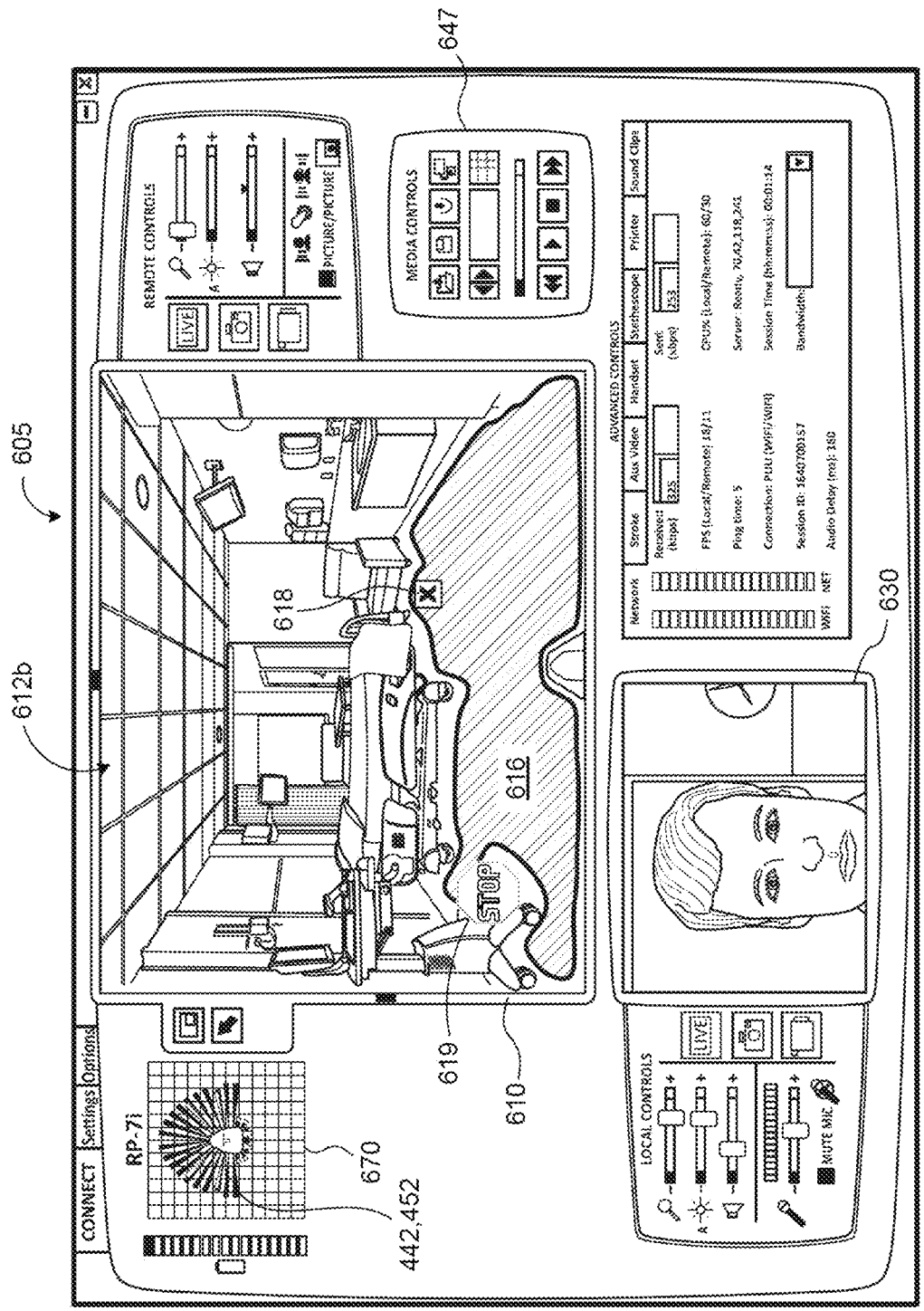
FIG. 11A is a schematic view of an example user interface that allows a user to specify a robot destination within an identified navigable area.

Referring to FIG. 11A, in some implementations, the user interface 605 of the telepresence software application 601 displays a remote navigation view 612b in the remote video feed window 610 (or another window). The remote navigation view 612b may have a navigable area 616 rendered over the live video feed of the remote view 612. The user may toggle between the remote view 612 and the remote navigation view 612b. The navigable area 616 may be determined based on the plan view map 810 and/or the robot map 820. The navigable area 616 may be shown as a bounded area with a field of view 832 of the robot camera(s) 320, 450, excluding obstacles. Moreover, the navigable area 616 may be filled with a color or other signal that communicates to a user that the navigable area is free of obstacles or other impediments.

Navigable area on the layout map may be highlighted based on information in the robot's internal obstacle map. In one embodiment, the navigable area may be identified as white-colored pixels in the image. The robot may return its position on the robot map and the position and orientation of the 3D depth camera. A processor may use the robot position and the kinematic state (e.g., pan and tilt angles) of the head camera to determine which pixels on the video screen represent the ground plane. That is, the processor may utilize the robot position and the perspective of the video feed to calculate the coordinates for each ground level pixel on the video feed. The white-colored pixels designating the navigable areas may then be overlaid on the ground level pixels on the video feed. Accordingly, the robot and/or a user controlling the robot could identify navigable areas by following the white-colored pixels. In alternative embodiments, any color pixel or other identifying mark could be used. Alternative data structures or marks could be used in place of white-colored pixels. Specifically, from the robot's POV the coordinates of ground level pixels that are navigable could be tagged in any of a wide variety of ways, so long as the robot is configured to recognize them.

The user may select a robot destination 618 in the navigable area 616, which causes the telepresence software application 601 to issue a drive command to the robot 100 to move to a location corresponding to the selected robot destination 618. In the example shown, the remote video feed window 610 of the user interface 605 provides a remote navigation view 612b of the robot 100 in a hospital room. The user selects a robot destination 618 as a location in the room next to a patient bed. The telepresence software application 601 may use the plan view map 810, robot map 820, three-dimensional map 705, two-dimensional (or 2.5D hybrid) height map 707, and/or stored image data 701 to resolve a distortion (within the same dimension and/or between dimensions) between the selected robot destination 618 on the remote navigation view 612b and a corresponding robot map location 824. The telepresence software application 601 may then issue a drive command to the robot 100 to maneuver autonomously or semi-autonomously to the robot map location 824, using its sensor system 400 and behavior system 510*a* to avoid any obstacles, such as moving people.

In one example, a map may be returned from a robot API call as an image, such as a PNG, JPG, or TIFF image. The robot could process the image in order to detect the pixels (e.g., black-colored pixels) that form the outline of an obstacle in the image. A curve fitting algorithm could be used to process the pixels that form the outline of the obstacle. The resulting curve(s) could then be used to generate an obstacle map. Additional processing may be done to further improve the obstacle detection and/or improve the accuracy of the curves fitting the detected obstacle outlines. For example, if a curve closes and forms a shape similar to a circle, the obstacle map could simply use a circle as a replacement. A similar idea could be applied to shapes like rectangles or ovals, people, faces, and/or those objects approximating a database of known object shapes from various perspectives.

The user interface 605 may provide a proximity sensor window 670 which displays a proximity of obstacles within a sensor field of view 442, 452 (e.g., within an three-dimensional imaging sensor field of view 452 and/or a laser scanner field of view 442).

In some implementations, the user may mark a protected region/zone on the remote video feed window 610 and/or the plan view map window 620 (not shown), using an avoid tag 662, 662*i*. A protected zone may be treated by the robot 100 as an object 12, and accordingly, protected zones may be avoided during autonomous navigation. Protected zones can be used to help create a wide berth around delicate equipment, or in order to ensure that the robot avoids other areas. The user may place an avoid tag 662, 662*i* on the plan view map 810 in the tagging view 660 or on the remote navigation view 612*b*. Moreover, the user may place other tags 662 on the remote navigation view 612*b*. The telepresence software application 601 may resolve a distortion between the remote navigation view 612*b* and the plan view map 810 and/or robot map 820 and then update the robot map 820 accordingly.

For example, determining a distortion between a plan view map and a video feed may comprise creating a transformation mapping between coordinate points in any of the navigation view 612*b*, the plan view map 810, and/or the robot map 820. Similar to overlaying a restricted region on a ground level in a video feed, the ground level of two-dimensional maps may be effectively coordinate-mapped onto a detected ground level in a video feed provided by a robot.

Figure 11B:
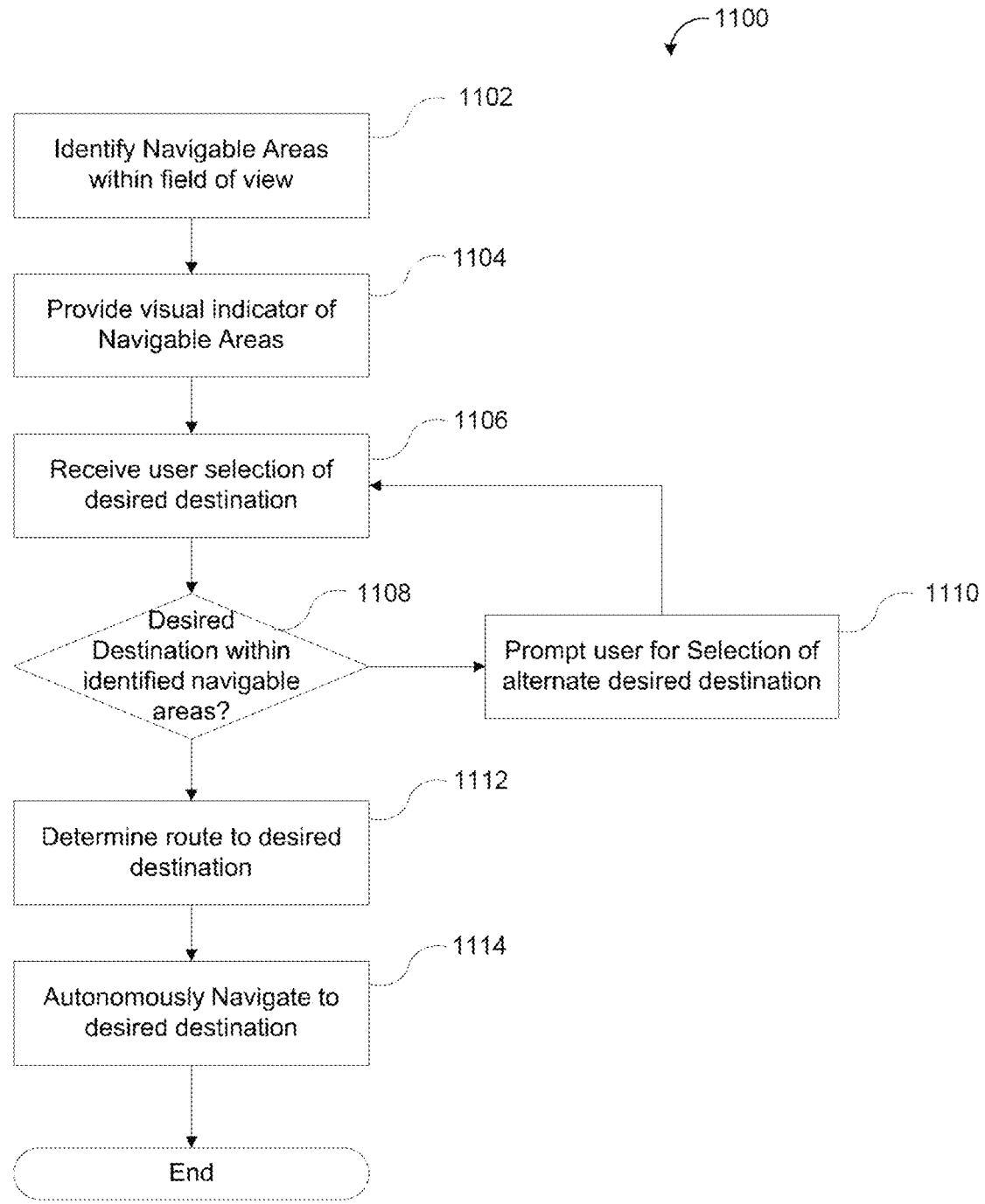
FIG. 11B provides an example arrangement of operations for a method of navigating a robot to a destination.

FIG. 11B illustrates a flow chart of an example arrangement 1100 of operations for a method of robot navigation (e.g., semi-autonomous) to a selected robot destination 618. The method includes identifying 1102 a navigable area 616 within a field of view 322, 442, 452 of the robot 100. Identification of navigable areas 616 may be accomplished using the sensor system 400 of the robot 100. The method also includes visually indicating 1104 the navigable areas 616 on the user interface 605, for example by displaying a bounded area (e.g., highlighted boundaries, filled with a color or pattern) on the remote navigation view 612*b*. The method may include receiving 1106 a user selection of a robot destination 618 and determining 1108 whether the robot destination 618 is within the identified navigable areas 616. If the robot destination is outside of identified navigable areas 616, the method includes prompting 1110 the user for a valid robot destination 618 within the navigable area(s) 616. If the robot destination 618 is within identified navigable areas 616, the method may include determining 1112 a route to the robot destination 618. This may entail determining a distortion between the remote navigation view 612*b* and the robot map 820 and then resolving a robot map location 824 corresponding to the selected robot destination 618. The method includes allowing 1114 the robot 100 to navigate (autonomously or semi-autonomously) to the robot destination 618.

Figure 11C:
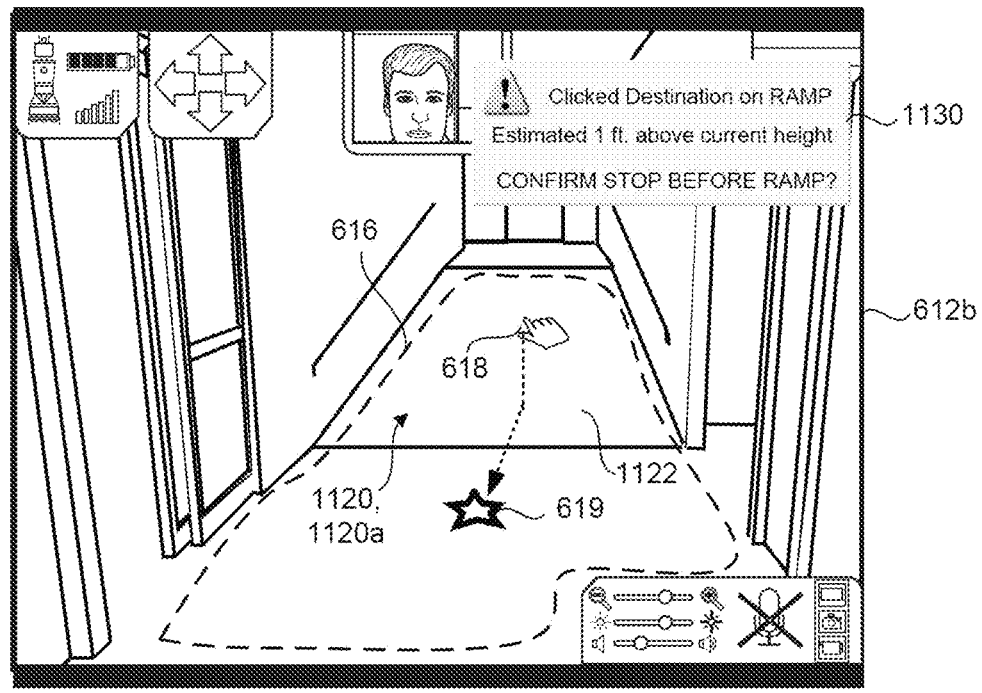
FIG. 11C is a schematic view of an example user interface prompting a user that a ramp was selected as a robot destination.
Figure 11D:
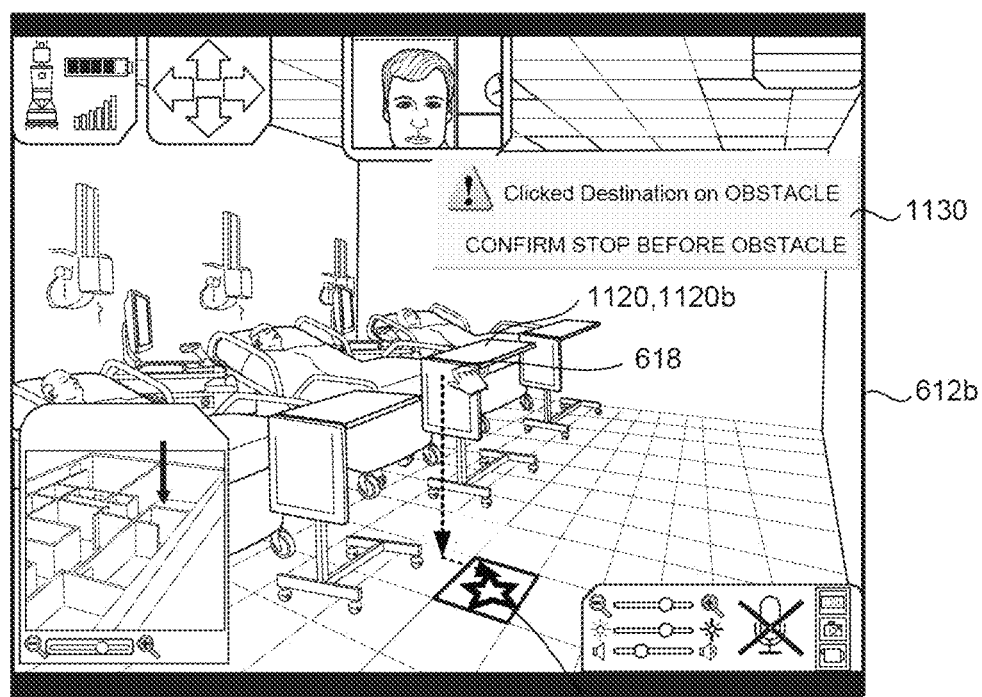
FIG. 11D is a schematic view of an example user interface prompting a user that an obstacle was selected as a robot destination.

FIGS. 11C and 11D illustrate example remote navigation views 612*b* where the user selected a robot destination 618 either beyond a navigable area 616 or on an obstacle 1120 (either actual or perceived by the robot 100). In the example shown in FIG. 11C, the user selected a robot destination 618 on a perceived obstacle 1120*a*, a ramp 1122. From a distance, the robot sensor system 400 may discern the ramp 1122 as an obstacle, because from a distance the ramp 1122 may have a perceived height above a threshold traversal height of the robot 100. Moreover, the robot behavior system 510*a* may execute an ODOA behavior 512*c* in response to sensor events raised due to sensor signals of the sensor system 400 indicating an obstacle having a height greater than the threshold traversal height. Using the plan view map 810 and/or the robot map 820, the robot 100 may determine that its local perception of the environment may be inaccurate, and that the ramp 1122 is not an actual obstacle, but is rather a perceived obstacle 1120*a*.

Although the ramp 1122 is within the navigable area 616, the telepresence software application 601 may determine the robot destination 618 on the ramp 1122 is an unsafe location to stop. The telepresence software application 601 may display an alert dialog box 1130, noting that the selected robot destination is an unsafe location to stop. In the example shown, the alert dialog box 1130 indicates that the user selected a ramp 1122 for the robot destination 618 and offers an alternative robot destination 619 just before the ramp 1122. Stopping the robot 100 on the ramp 1122 may be hazardous for people near the robot 100 and for the robot 100 itself, if the robot 100 tips or rolls down the ramp 1122. By determining that the robot destination 618 is on the ramp 1122, the telepresence software application 601 can either prohibit such a robot destination 618 and/or offer a safe alternative destination 619, in this case before the ramp 1122.

Referring to FIG. 11D, when the user selects an actual obstacle 1120*b*, the telepresence software application 601 may display an alert dialog box 1130, noting that the selected robot destination 618 is outside of the navigable area 616 or an obstacle 1120. In the example shown, the alert dialog box 1130 indicates that the user selected an obstacle 1120*b* for the robot destination 618 and offers an alternative robot destination 619 just before the obstacle 1120*b*.

Figure 12:
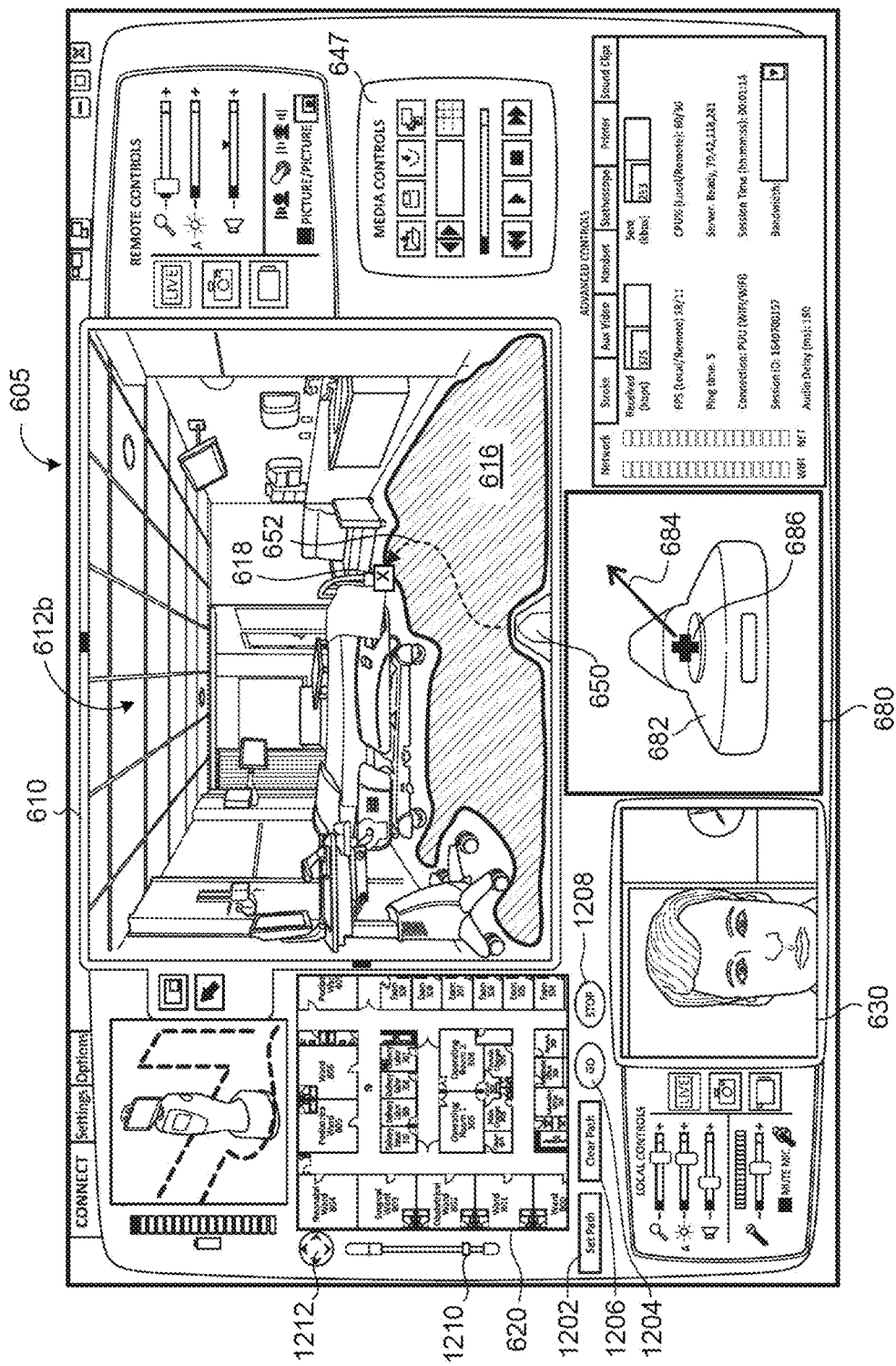
FIG. 12 is a schematic view of an example user interface that allows a user to specify a robot drive path within an identified navigable area.

Referring to FIG. 12, in some implementations, the remote navigation view 612*b* displayed by the user interface 605 of the telepresence software application 601 allows a user to specify a robot path 652 to a selected robot destination 618 in the navigable area 616. The user may specify the robot path 652 using a variety of input devices. For example, on a touch screen display, the user may drag his/her finger or a stylus from the robot icon 650, denoting the current robot position, to the robot destination 618. In additional examples, the user may drag the robot icon 650 (e.g., using a mouse or touch gesture) along the prescribed robot path 652 to the robot destination 618. In the example shown, the user may select a set path button 1202 on the user interface 605 allowing the user to indicate that a gesture performed within the navigable area 616 should be interpreted as the robot path 652. The user may trace the robot path 652 within the remote video feed window 610. Similarly, the user may select the robot path 652 on the plan view map 810 displayed as the two-dimensional map 622a in the map window 620. After setting the robot path 652, the user may press a go button 1204 to set the robot 100 into motion. Similarly, a stop button 1208 may be used to stop the motion of the robot 100. A clear path button 1206 may remove or clear the set robot path 652 from the remote navigation view 612b.

A display window may include a fly-out icon panel that is revealed by a mouse-over. For example, the icon panel may "fly" out from the top left of the window. The icon panel may allow a user to select a manual drive, a click-to-drive, and a head motion icon. In one embodiment, a user may toggle through the icons using the space bar. Manual drive may allow a user to click-to-destination and/or click-and-drag a path. After drawing a path on the map, the user may right-click and select "Save Path" from the popup menu. They can give a name to the path. Later the user may "Load Path", and the robot will navigate to the starting point of the path, and then navigate along the prescribed path to the destination. The path may be stored as a tag data structure, including tag coordinates and tag information. The tag path may include multiple stops along the way. When drawing the path, the user may indicate way points along the path. In some embodiments, the way points may be represented by tag annotations that include stop signs. Later, when traversing the path, upon reaching a way point, the robot may flashes the "stop" button and the path may become lighter and/or translucent. At this point the user may perform a consult and do local driving, then click "go" to resume the path. Accordingly, a physician can save a path for his evening rounds, hitting all the rooms and stations in a preferred order and with a pre-planned route.

In head mode, a user may draw a box or outline on a portion of a video feed in order to center the head (upper portion) of the robot on the center of the box or an object within the box. Additionally, a user may click a location in order to change the heading of the head (upper portion) of the robot and/or the entire robot. Various button and peripheral control toggles may be used to independently control the base (lower portion) and head (upper portion) of the robot. For example, holding the shift key while in the head mode may make the curser a hand icon on the screen and allow the user to grab and drag the viewpoint of the head.

In some embodiments, a star icon may be used to control the navigation of the robot. The star icon may be displayed in any of the various views and may be selectively moved by the user to change the direction and/or velocity of the robot. Alternative icons in addition to a star icon may be used.

Returning to FIG. 12, a virtual joystick window 680 may provide another input device for specifying the desired path 652 or to manually control of the robot 100. The virtual joystick window 680 may display a robot orientation indicator 682 and a navigation vector 684. A user may control the direction and speed of the robot 100 using the navigation vector 684. A virtual joystick may facilitate control of the robot 100 by the user of a device that may not typically have a mouse or conventional joystick, such as a tablet computer.

A "stitched" video image may be displayed in the virtual joystick window 680. The "stitch" video and image may be generated using a live downward pointing camera 320, 450 on the front of the robot 100 and using a live downward pointing camera on the rear of the robot 100. A user may grab (e.g., using a mouse or touch gesture) and drag on robot motion indicator 686 in order to specify a direction of robot movement and a drive velocity. Driving the robot 100 from the virtual joystick window 680 has advantages over using the remote video feed window 610 for mouse-based or virtual joystick driving. Specifically, this view may reduce lens distortion, lack of depth information, and perception issues based on the rotation of the robot head 160 that a user may experience while driving the robot 100 using the video feed displayed in remote video feed window 610.

In addition to allowing the user to specify a desired path within the remote video feed window 610, the user may specify the robot path 652 on the map 622 displayed in the map window 620. Specifying the robot path 652 in the plan view map window 620 may allow the robot 100 to navigate over longer distances, and thus may free the user to perform other tasks while the robot 100 is in transit. Various controls may also be provided in order to manipulate the zoom and displayed area of the map 622 shown in the map window 620. A desired zoom may be specified using slider 1210, and a desired area may be displayed using an area pan control 1212.

Accordingly, a non-technical user may be able to navigate from one location to another using any combination of the various navigation methods and controls. For example, in long-distance travel, a user may click a destination on a plan view map and the robot may autonomously navigate to the selected location. In mid-range travel, the user may select a destination in a video window of a location within the field of view of the robot. In close range travel, the user may manually control the robot's navigation path, rotations, head movements, and the like using a mouse, joystick, virtual joystick, or meta joystick.

Figure 13:
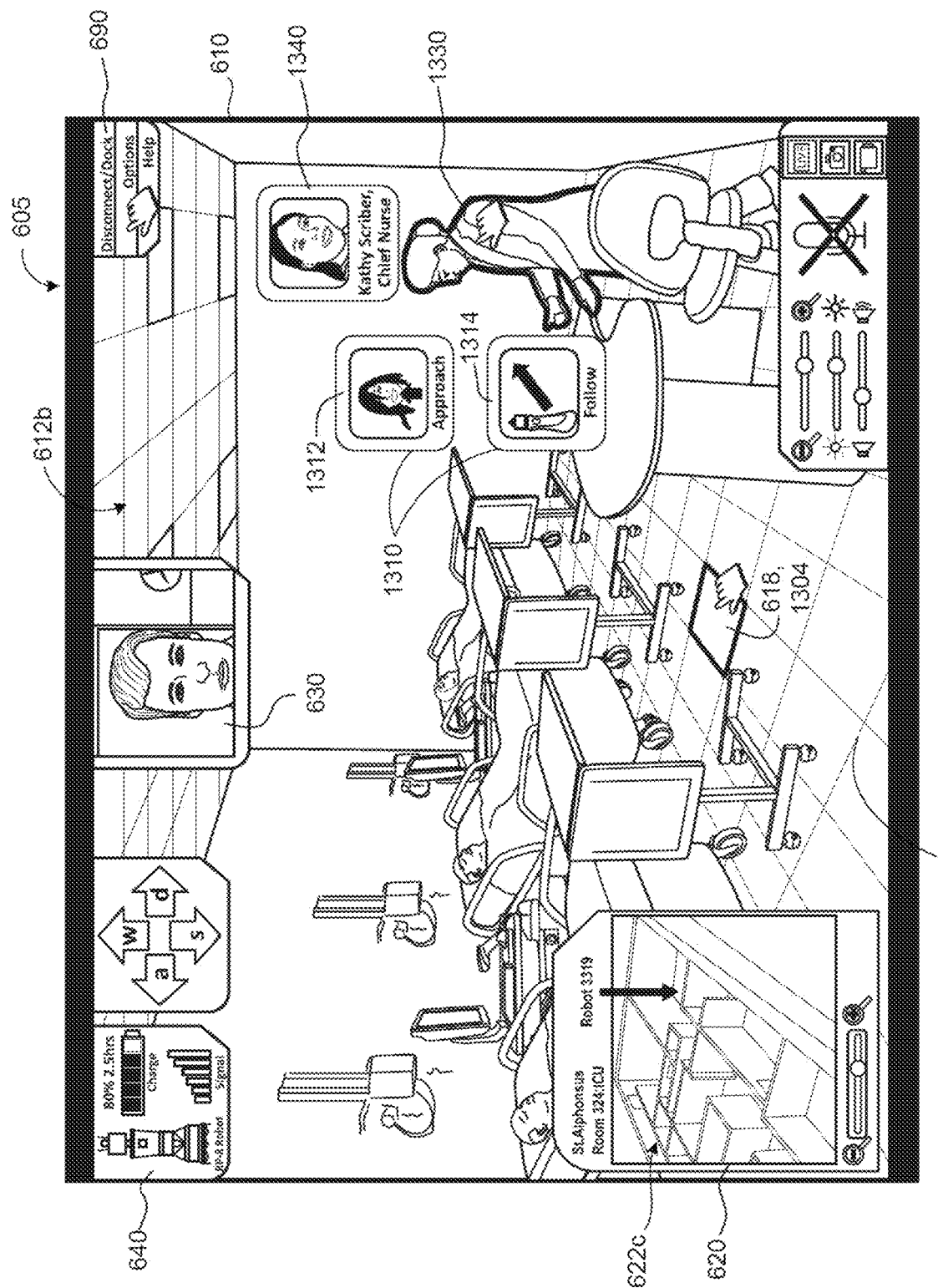
FIG. 13 is a schematic view of an example user interface that incorporates hyper-tags and context sensitive commands.

FIG. 13 illustrates an example user interface 605 of the telepresence software application 601 having a maximized remote video feed window 610 displaying a remote navigation view 612b that accepts hyper-tags 1310 and/or context sensitive commands selectable by the user. The user interface 605 includes the local video window 630 and the plan view map window 620 overlaid on the remote video feed window 610. In the example shown, the plan view map window 620 displays a three-dimensional (three-dimensional) map 622c. The three-dimensional map 622c may be utilized by the user to cause the robot 100 to navigate semi-autonomously to a selected robot destination 618 on the three-dimensional map 612c. In some implementations, a virtual three-dimensional grid 1302 is displayed in the remote navigation view 612b. Using a determined distortion between the plan view map 810 and the robot map 820, the telepresence software application 601 can determine the location of the floor surface 5 in the live video feed to overlay the three-dimensional map 622c. The user may select a grid square 1304 as a robot destination 618 on the virtual grid 1302 in order to cause the robot 100 to autonomously navigate to the selected grid square 1304. The virtual three-dimensional grid 1302 may allow for improved precision in the positioning of the robot 100.

In the example shown, a variety of hyper-tags (tags) 1310 providing context-sensitive actions are displayed and made available to a user. The context-sensitive actions include an approach command 1312 and a follow command 1314. These context-sensitive actions may be generated upon the identification of a person 1330 within the field of view 322, 442, 452 of the robot 100. The user may invoke the approach command 1312 in order to position the robot 100 in front of the person 1330. The approach command 1312 may cause the execution of an approach behavior 512a (FIG. 5) by the robot behavior system 510a, whereby the robot 100 identifies the person 1330 using its sensor system 400 (e.g., using facial recognition) and drives to face the identified person 1330. The user may invoke the follow command 1314 to drive the robot 100 behind the person 1330 and follow at a three-foot distance. The follow command 1314 may cause the execution of a person follow behavior 512b (FIG. 5) by the robot behavior system 510a, whereby the robot 100 identifies the person 1330 using its sensor system 400 (e.g., using facial recognition) and drives to follow the identified person 1330. In some examples, the robot 100 may detect individuals within its field of view 322, 442, 452 using a facial recognition routine. A label 1340 may be displayed that identifies the individual. For example, the information may include name, title, occupation, address, business address, email address, web-page address, user notes, etc.

The telepresence software application 601 may determine a distortion between the displayed two-dimensional map 622a and the first-person video feed captured by the robot camera 320. Determining such a distortion may include determining a coordinate transformation between the two-dimensional map and the three-dimensional "map." When the user places a tag 662 and/or hyper-tag (which may comprise a tag) 1310 either on the remote view 612 of the remote video feed window 610 or on the two-dimensional map 622a of the map window 620, the telepresence software application 601 may apply the distortion to tag map coordinates associated with the tag 662 and/or the hyper-tag 1310 to determine corresponding video coordinates or plan view map coordinates, respectively, and overlay a tag annotation associated with the tag 662 or hyper-tag 1310 on the displayed remote view 612 (i.e., first-person video feed) or the map 622, respectively, using the determined video or map view coordinates. In various embodiments, the three-dimensional rendition of the tag annotation may be dynamically re-rendered based on the current position of the remote telepresence robot and a perspective of the tag relative to the video feed. Accordingly, as the location of the robot and/or the perspective of the live video feed changes, such as when the head (upper portion) of the robot pans or tilts, the tag annotation may be dynamically re-rendered. For example, a tag annotation corresponding to a ramp may be overlaid in the video feed with respect to the floor. Similarly, a tag annotation associated with an object on a wall may be overlaid with respect to the object or the wall.

As described herein, the tag may include tag information comprising a robot action modifier. The tag may be interpreted by a robot operator, a local terminal, or the remote telepresence robot and cause the robot to execute a predetermined action. For example, the robot action modifier may direct a robot to not enter a specific area, to travel slowly through a certain area, to travel fast through a certain area, to use extra caution, and/or to perform other actions. Tags in general may include any of a wide variety of information, such as an availability of a wireless communication signal, a speed the remote telepresence robot should travel, a location of a point of interest, a location of a person, a location of a docking station, a location of a rest area, a location of a glass wall, a location of a ramp, a location of an object, an optimal route to navigate a tight area, an optimal rout to navigate a congested area, and an action a remote telepresence robot should execute. The tag may be created by a user, automatically by a terminal, automatically by a robot, and/or in response to historical data collected by the terminal and/or robot.

The robot may include a tag identification system configured to identify tags having tag coordinates encountered along a navigation path. A robot may "encounter" a tag when the tag coordinates are within the local perceptual space of the robot and/or the tag coordinates are relevant to an objective, planned navigation path, or the planning of a navigation path. Accordingly, a tag identification system may "encounter" a tag along a navigation path, even if the robot is not yet in proximity and/or may never be in proximity to the tag coordinates of the tag.

A robot and/or remote terminal determining a navigation path for a robot may take into account tags or potential tags that could influence the navigation path. Accordingly, the tag identification system may be used to identify tags having tag coordinates projected to be along potential navigation paths during the determination of a navigation path. For instance, several potential navigation paths may be used to reach a desired destination and the selection of which navigation path will be used may depend on the tags relevant to each of the potential navigation paths. A robot selecting between multiple potential navigation paths may identify relevant tags in order to determine which navigation path would provide the best wireless connectivity. Other factors, such as ramps, elevators, distance, congestion, objects, In the example user interface 605 shown, the dashboard window 640 provides a battery charge status, a wireless signal strength indicator, and a robot outline having portions that may light up when service is required. An options window 690 allows the user to disconnect or dock the robot with a docking station and set software and/or robot options.

Figure 14:
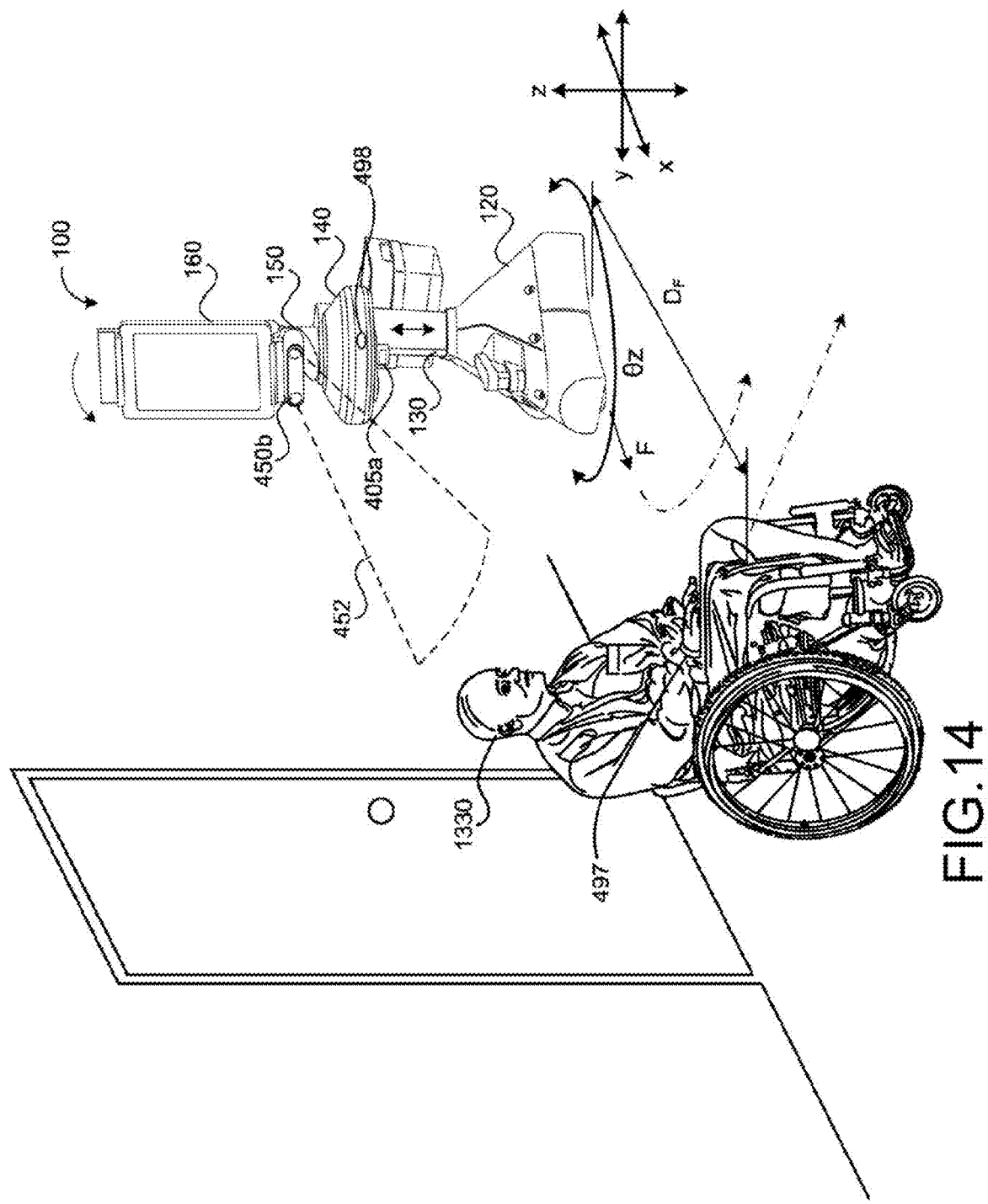
FIG. 14 is a perspective view of an example telepresence robot maintaining a sensor field of view on a person.

Referring to FIG. 14, in some implementations, while executing the person follow behavior 512b, the robot 100 may detect, track, and follow a person 1330. Since the robot 100 can pan and tilt the head 160 using the neck 150, the robot 100 can orient the second three-dimensional image sensor 450b to maintain a corresponding field of view 452 on the person 1330. Moreover, since the head 160 can move relatively more quickly than the base 120 (e.g., using the drive system 200), the head 160 (and the associated second three-dimensional image sensor 450b) can track the person 1330 more quickly than by turning the robot 100 in place. The robot 100 can drive toward the person 1330 to keep the person 1330 within a threshold follow distance range $D_F$ (e.g., corresponding to a sensor field of view). In some examples, the robot 100 turns to face forward toward the person/user 1330 while tracking the person 1330. The robot 100 may use velocity commands and/or waypoint commands to follow the person 1330.

Additional details and features concerning person recognition and person following can be found in PCT application serial number PCT/US11/35488, filed on May 6, 2011, which is hereby incorporated by reference in its entirety.

Figure 15B:
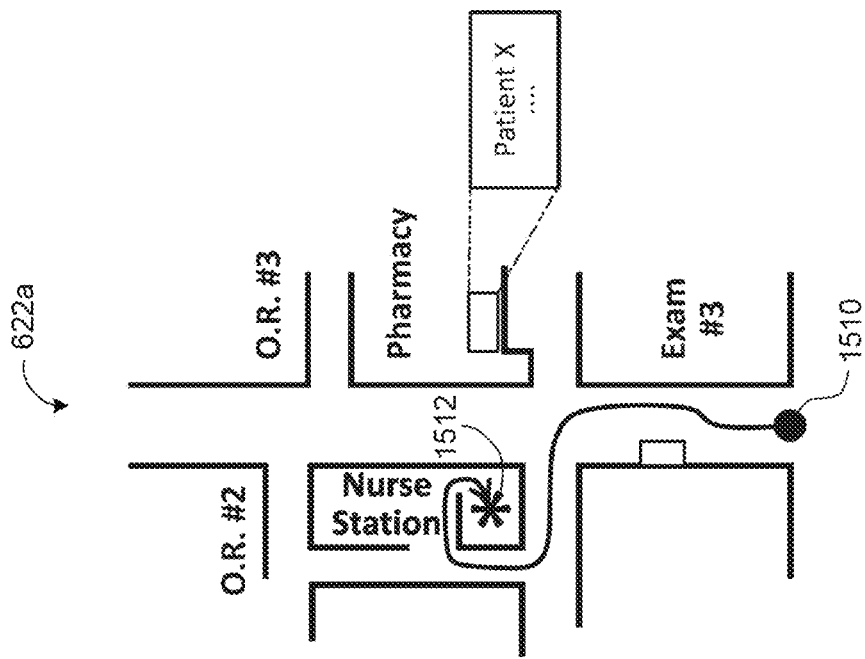
FIG. 15B is a schematic view of an example two-dimensional map view that include hyper-tags.
Figure 15A:
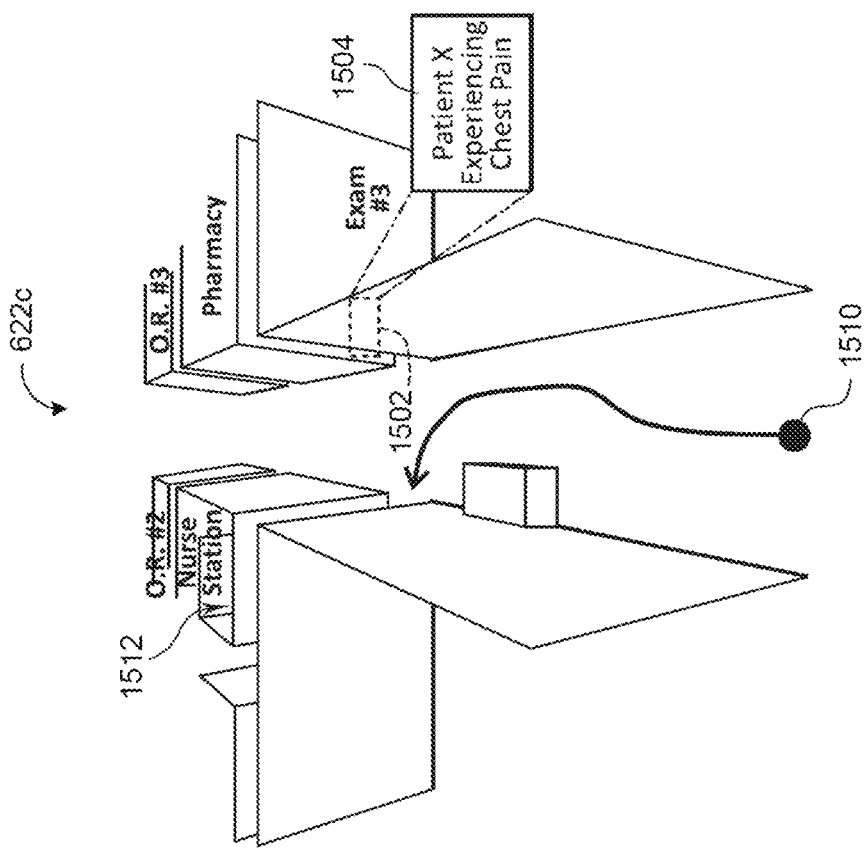
FIG. 15A is a schematic view of an example three-dimensional map view that includes hyper-tags.
Figure 16A:
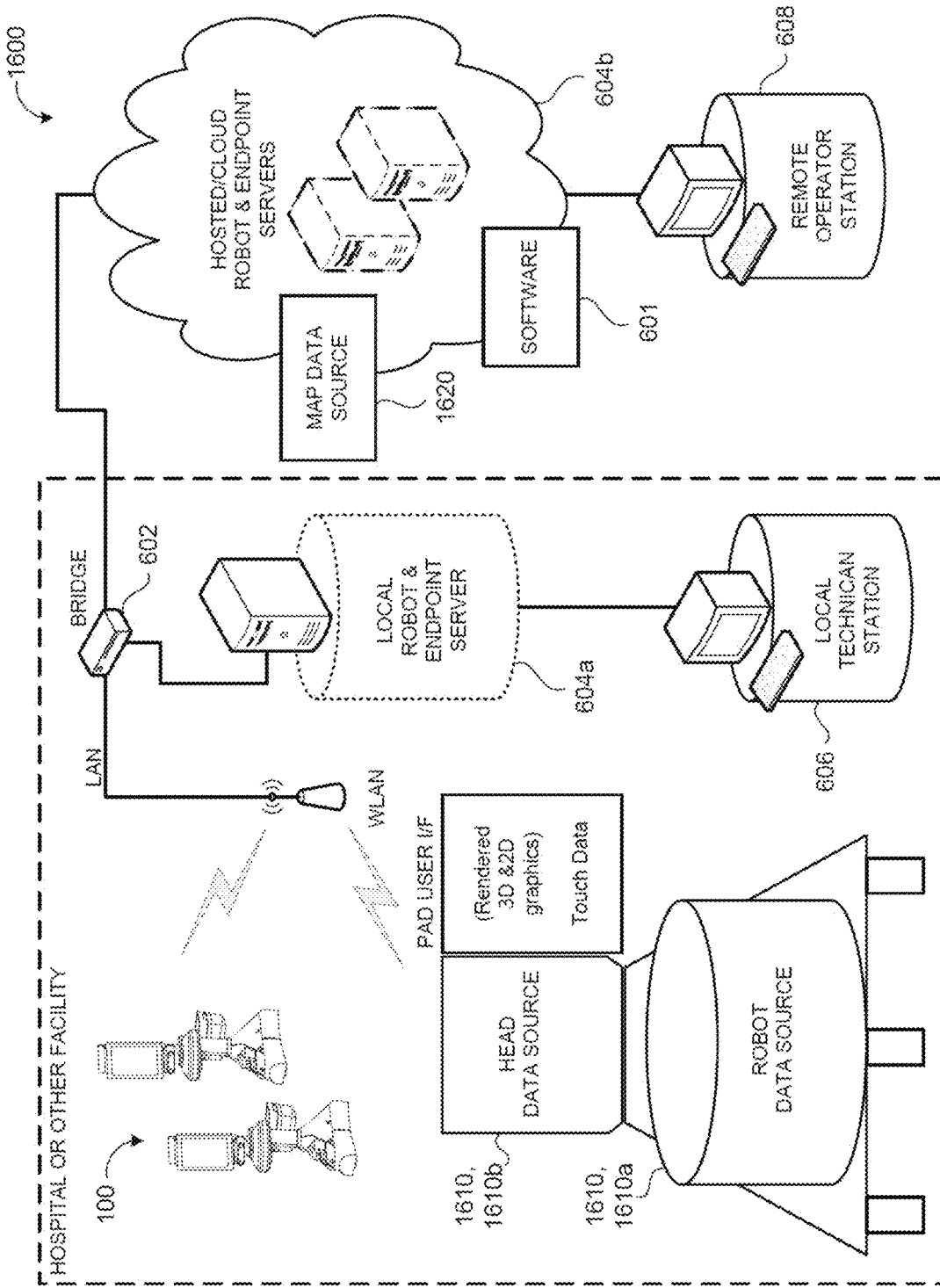
FIG. 16A is a schematic view of an example robot system.
Figure 16B:
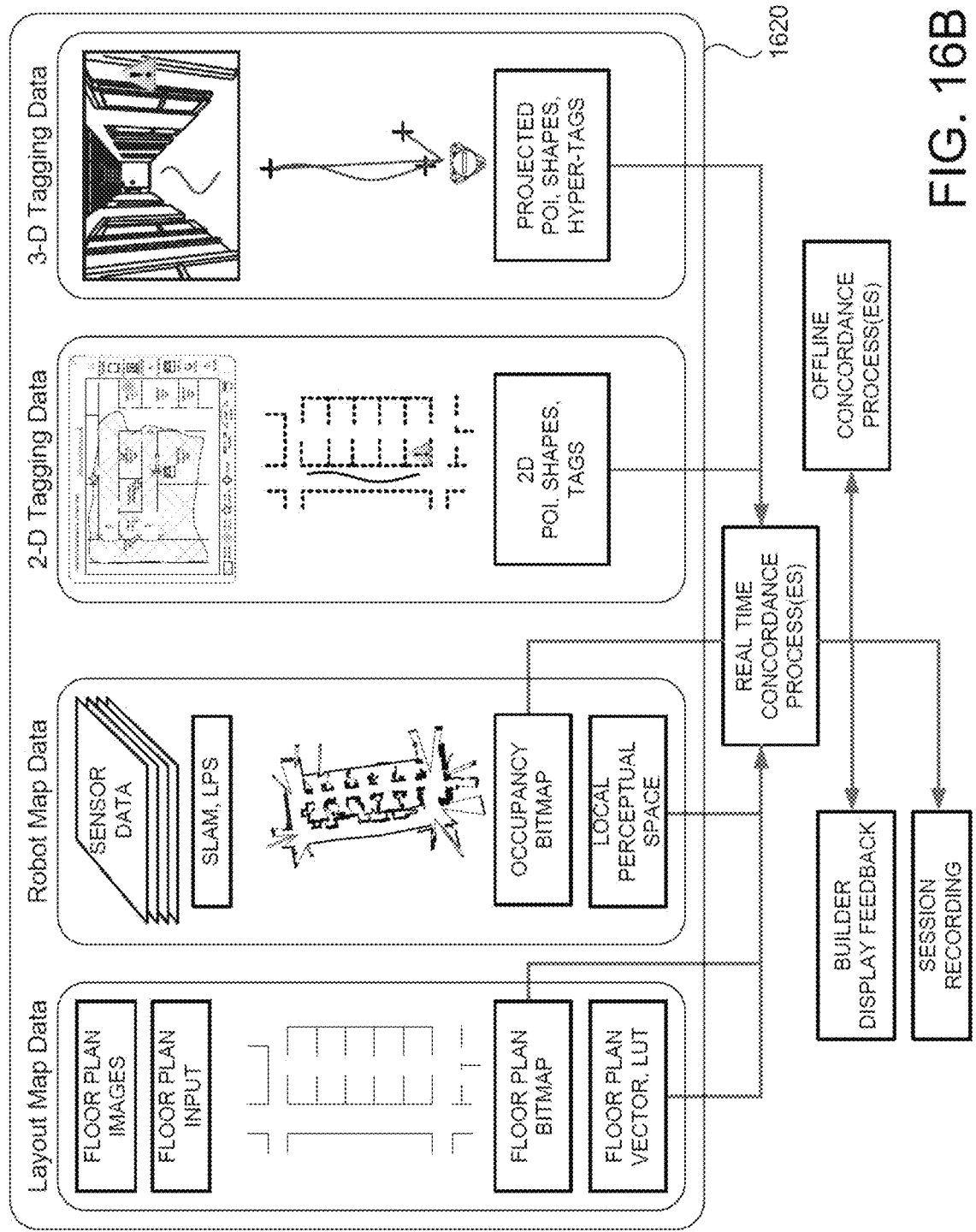
FIG. 16B is a schematic view of example interactions with a map data source.
Figure 16C:
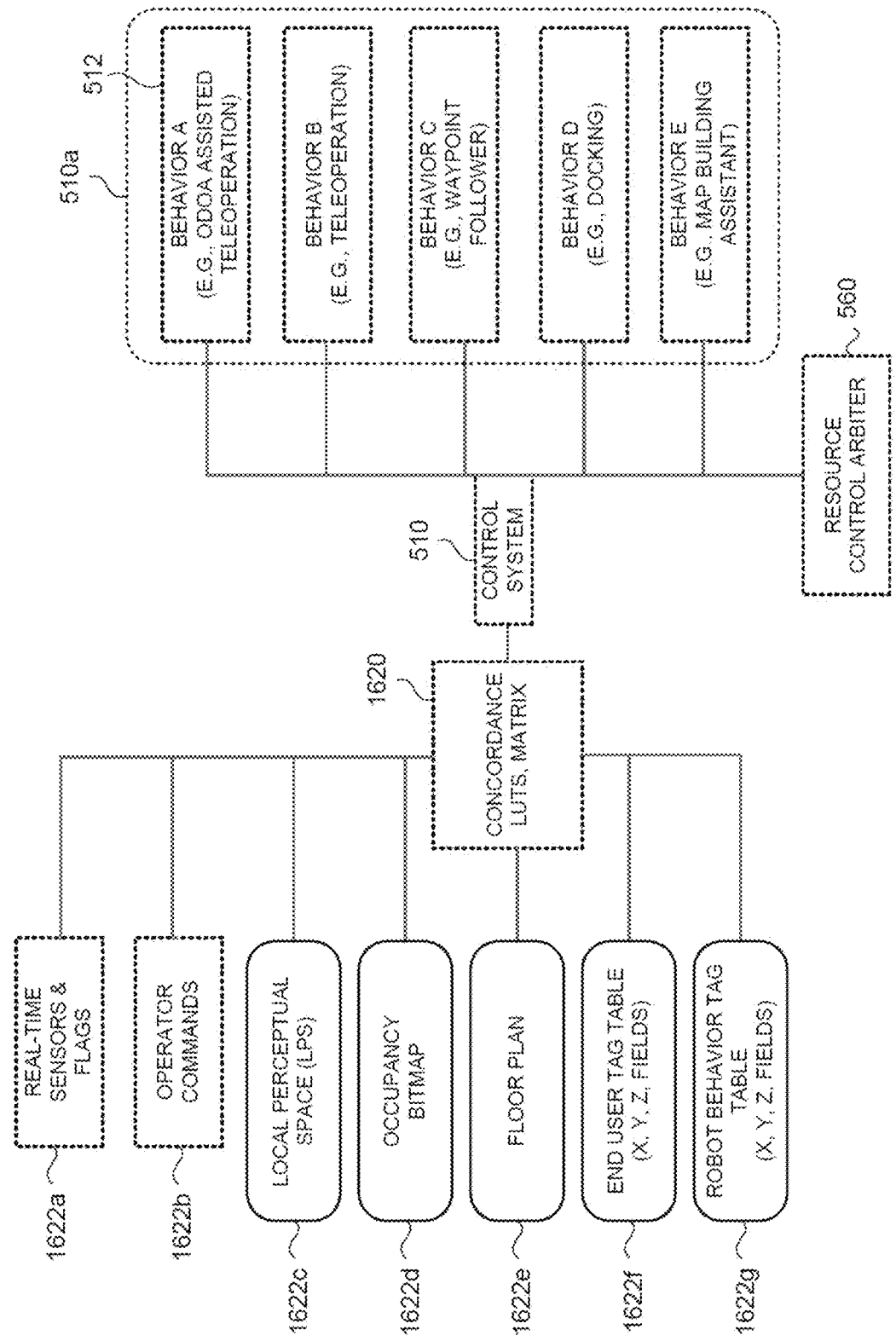
FIG. 16C is a schematic view of example interactions between a robot control system and a map data source.
Figure 16D:
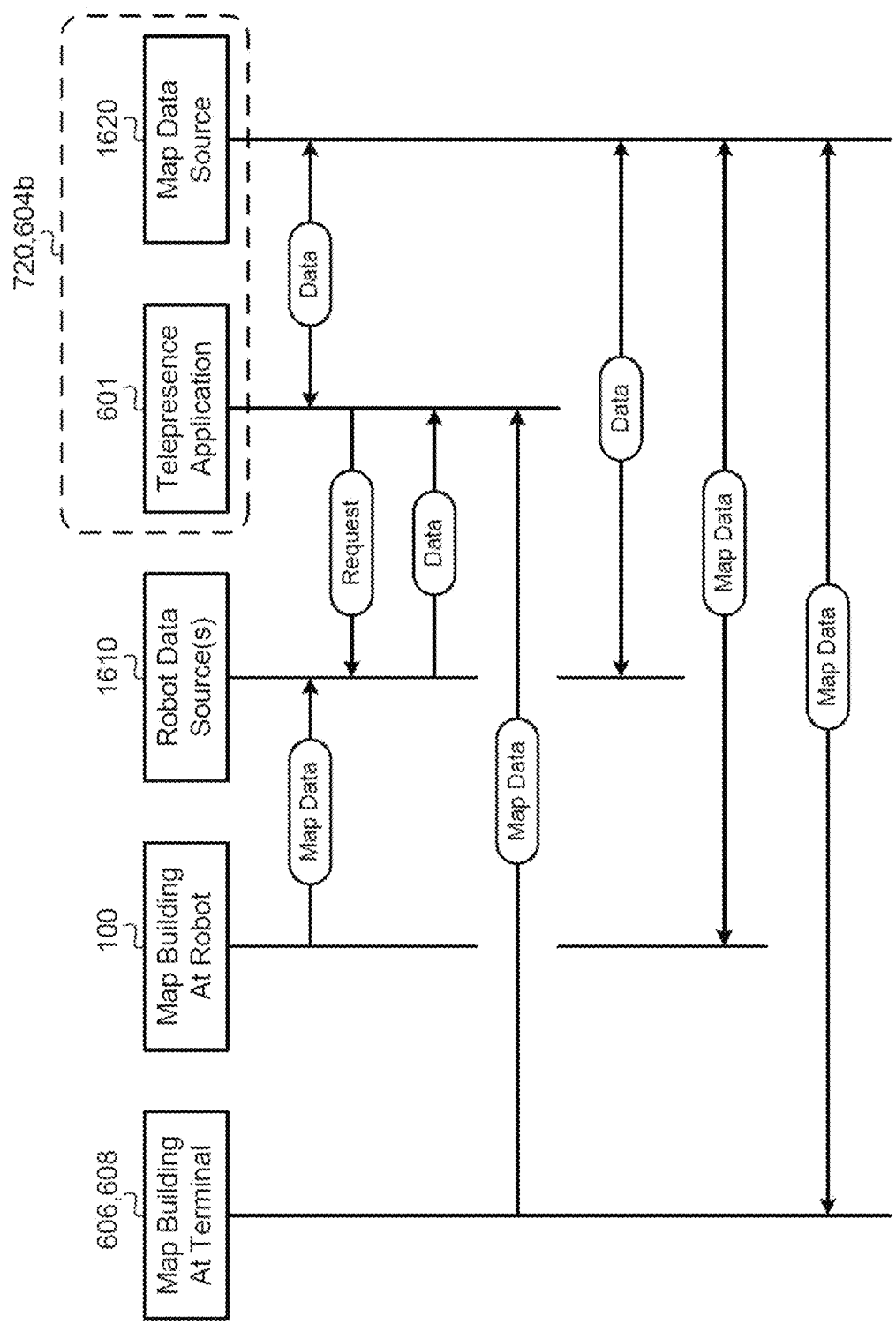
FIG. 16D is a schematic view of an example robot system.

FIGS. 15A and 15B illustrate alternative three-dimensional maps 622c and two-dimensional maps 622a displayable in the plan view map window 620 that include hyper-tags 1310 associated with various information and that may be used to cause the robot to navigate autonomously to a particular destination. The hyper-tags 1310 may include information about various locations or information related to patients. A user may add labels 1502 or mark-ups 1504, such as personal notes, shared notes, sketches, drawings, etc. A robot location 1510 may also be identified. A user may specify a robot destination 1512, such as a nurse's station. The robot 100 may navigate autonomously to the specified robot destination 1512.

The telepresence software application 601 may display information on the remote video view 612 and/or a map 622, indicating physical areas of interest. For example, a small arrow with an attached bubble reading "Pharma" may indicate the location of the pharmacy room. Such a bubble could comprise a tag. For example, the tag could include tag coordinates indicating where the word "Pharma" should be displayed; tag information, such as relevant information related to the pharmacy; and a tag annotation, such as a graphical representation in two-dimensional and/or three-dimensional of the word "Pharma." In some examples, the user can determine what information is available about nearby rooms by placing the mouse over or gesturing over that area, causing the display of any corresponding available information. With this information, the user can quickly choose to go to a destination (e.g., the pharmacy room) by selecting a robot destination 618 in the remote navigation view 612b (FIG. 12).

For example, according to one example a robot or remote terminal could retrieve tag coordinates that correspond to tags associated with a robot map. Using the robot position, tags that are in close proximity to the robot may be identified. Tags within the field of view of the robot may be identified using the orientation of the robot's head (upper portion). The robot and/or remote terminal could then calculate a set of coordinates for all of the pixels on the video screen and render a tag annotation associated with each tag within the line of sight based on the position of the robot and the perspective provided by the robot's current head orientation (pan and/or tilt). According to some embodiments, Denavit-Hartenberg parameters (DH parameters) may be used as a standard coordinate system for spatial linkages between the video feed and the map plan view.

Referring again to FIG. 8E, the tagging view 660 of the user interface 605 allows the user to place tags 662 on a plan view map 810 to designate locations of interest and/or mark the plan view map 810 with information, such as obstacles, preferred robot travel routes, etc. Referring also to FIG. 13, the user may place hyper-tags 1310 on the remote navigation view 612b to mark locations with context-sensitive information. The map data source 1620 may store the tagging and hyper-tag information (e.g., locations, tag identifiers, tag content) along with layout map and/or robot map information. As used herein, hyper-tags may be embodied as tags and use a similar data structure to tags, as described herein.

In addition or alternatively to allowing the user to place tags 662 and hyper-tags 1310 in the user interface 605, the user may enter user-specific hyper-tags 1310 during operation of the robot 100. The user may invoke a command that allows for the insertion of a hyper-tag 1310 at a current robot location. Another command may allow for the removal of the hyper-tag 1310. Further, other users (e.g., nurses) may be allowed to add hyper-tags 1310 that may be shown to a user of the robot 100. A "nurse map application" may display a top-down map or a tagging view 660 that allows placement of temporary hyper-tags 1310, for example, to identify rooms of interest to a doctor who may soon be logging in. Moreover, some hyper-tags 1310 may be user-specific and/or time-specific. For example, a stroke patient in a room may be showing signs of deterioration. The nurse can call up the "nurse map application," find that room on the map and enter a hyper-tag 1310. The nurse may fill in a hyper-tag as follows: hyper-tag_name="Stroke patient deteriorating," user_specific="Dr. Reynolds," duration=1 hour. Thus, if Dr. Reynolds logs in within the next hour, he would see a hyper-tag 1310 associated with the patient's room on the map additionally indicating "Stroke patient deteriorating." On approaching that wing, he may also see a hyper-tag 1310 pop up pointing to that room in the video stream, labeled "Stroke patient deteriorating." No other doctor would see those labels, and Dr. Reynolds would only see them during that first hour.

A doctor may also set up temporary bookmark and reminder hyper-tags 1310, directly at a local or remote station interface 606, 608, to assist with his/her work plan. In some examples, the doctor may assign numbers to several patient rooms at the start of the session. Then during the session, he/she may see the numbers on the displayed map 622 and in popup hyper-tags 1310 to remind him/her of the order in which to visit the patients 614. The doctor may add notes which can be viewed through the remainder of the session or upon next returning, for example, "come back at end of session" on one patient, or "write prescription" or "check in again at 4 pm."

Additionally, "smart" hyper-tags 1310 may be displayed automatically. For example, a nurse may enter photos of incoming patients 614 into a database (e.g., stored locally and/or on cloud storage 722) cross-referenced with their electronic medical record. The telepresence software application 601 may execute a face recognition algorithm on a video stream captured by the robot camera 320 to identify the patients 614, 1330, which can be cross-referenced to the database. Upon recognition of a patient's face, the telepresence software application 601 may automatically pull up and display the patient's electronic medical record.

Referring again to FIG. 14, in some implementations, each patient 614, 1330 receives a radio frequency identification (RFID) chip 497, such as on a wristband. The robot 100 may have an RFID reader 498 in communication with the controller 500 as part of its sensor system 400 to recognize nearby patients via the RFID chip. The telepresence software application 601 may display a corresponding hyper-tag when the patient comes within RFID range (e.g., six feet) of the robot 100. The hyper-tag 1310 may appear to be floating in the air, since RFID is not direction-specific. An alternative hybrid approach may use computer vision techniques to identify the existence of a patient 614, 1330 in the field of view 322 of the robot 100 by identifying a human face, and then assuming that the RFID match belongs to that patient and localizing the hyper-tag 1310 on the patient 614, 1330.

Referring to FIGS. 16A-16D, in some implementations, a robot system 1600 includes one or more telepresence robots 100 in communication with a bridge 602, which communicates with a local robot endpoint server 604a and a remote endpoint server 604b (e.g., such as the cloud computing service 720 (FIG. 7)). The local robot endpoint server 604a communicates with a local technician computing device 606 and the remote endpoint server 604b communicates with a remote operator computing device 608. The robot system 1600 also includes one or more data sources 1610 for storing sensor data received from the robot sensor system 400 and/or user interaction data, such as information obtained from the user through the web pad 310 and/or the user interface 605. In the example shown, the robot system 1600 includes at least one robot sensor data source 1610a for storing sensor data and at least one head data source 1610b for storing user interaction data. The data sources 1610 may reside on the robot 100, cloud storage 722 (FIG. 7), the local robot endpoint server 604a and/or the remote endpoint server 604b.

A map data source 1620, such as a database stored on the robot 100, cloud storage 722, the local robot endpoint server 604a and/or the remote endpoint server 604b, can store information for the plan view map 810, the robot map 820, tag 662 information, and/or hyper-tag 1310 information. The map data source 1620 may be a single database or combination of data sources 1610, such as the robot sensor data source 1610a and the head data source 1610b. The telepresence software application 601 and/or the robot 100 (e.g., the controller 500) may access the map data source 1620 to execute real-time or off-line concordance processing, provide user interface feedback, perform navigation routines, render maps 622, etc.

In some implementations, the control system 510 executing on the controller 500 of the robot 100 accesses one or more of the data sources 1610, such as the robot sensor data source 1610a, the head data source 1610b, and/or the map data source 1620 to issue events recognizable by the behavior system 510a. In response to raised events, the behavior system 510a may execute one or more behaviors 512 that affect the selection of a command executed by the resource control arbiter 560 on the robot resources 530 (FIG. 5). In the example shown in FIG. 16C, the robot control system 510 communicates with the map data source 1620 to access a concordance matrix/database, which may store concordance process information, such as real-time sensor/flag data 1622a, operator commands 1622b, local perceptual space data 1622c (e.g., volumetric point cloud data received from a three-dimensional image sensor 450), occupancy bitmap data 1622d (e.g., the robot map 820), floor plan data 1622e (e.g., the plan view map 810), and an end-user tag table 1622f (e.g., storing x, y, z coordinates and tag fields), and/or a robot behavior tag table 1622g (e.g., storing x, y, z coordinates and tag fields). Referring also to FIG. 5, behaviors 512 of the behavior system 510a may evaluate possible outcomes of robot actions based on raised events, such as sensor events from the sensor system 400 and tag events (e.g., which may mimic a sensor event) raised by placed tags 662, 1310 stored in the tag tables 1622f, 1622g. Accordingly, the action selection engine 580 may select a feasible robot action having the best outcome based on behavior evaluations. As a result, the robot 100 may autonomously operate in a manner that takes into account the tags 662, 1310 received by the telepresence software application 601.

Referring again to the ramp example shown in FIG. 11C, when the robot 100 approaches a ramp 1122, the robot control system 510 may perceive the ramp 1122 as an obstacle 1120, based on sensor signals received from the sensor system 400. In order to discern between a perceived obstacle 1120a and an actual obstacle 1120b, the control system 510 may need to access a common database, such as the map data source 1620, storing robot data and user data. Using the map data source 1620, the control system 510 can determine that the detected ramp 1122 is a perceived obstacle 1120a, rather than an actual obstacle 1220b. Moreover, the control system 510 may communicate with the telepresence software application 601 to receive a user input as to whether the user perceives the ramp 1122 as an actual obstacle 1120b and/or to receive an alternative robot path 652 and/or an alternative robot destination 619. The telepresence software application 601 can use the map data source 1620 to resolve distortions between two-dimensional maps 622a, 810 and three-dimensional maps 622c, between live video feeds in the remote view 612 and two-dimensional and/or three-dimensional maps 622a, 622c to provide hybrid maps 622b (FIG. 9B). Moreover, the telepresence software application 601 can use the map data source 1620 to render the look-ahead view 612a in the plan view map window 620 (FIG. 10C).

Referring again to FIG. 12, in additional implementations, when the user selects a robot path 652 on one of the two-dimensional map 622a, hybrid map 622b, three-dimensional map 622c, and the remote view 610, the telepresence software application 601 can use the map data source 1620 to resolve distortions between any of the maps 622 and the remote view 612 and apply the distortion to the selected robot path to determine a corresponding sequence of robot path map coordinates on the robot map 820 for use by the robot controller 500 when executing a drive command to the destination 618. Moreover, the telepresence software application 601 may apply the determined distortion(s) to resolve corresponding sequences of robot path coordinates for displaying the robot path 652 on any of the maps 622 and the remote view 612. The map data source 1620 may store the determined distortions and/or the sequences of robot path coordinates for displaying the robot path 652 on any of the maps 622 and the remote view 612.

Accordingly, it should be broadly understood that the term "distortion" as used herein relates to resolving spatial coordinate errors, differences of transformation from one coordinate system to another, including between coordinates systems of different dimensions. For example, a robot and/or remote terminal may determine a distortion between a two-dimensional plan view map and a two-dimensional map generated, at least in part, by a robot, such as those generated using various robot sensor or laser scans. Additionally, a robot and/or remote terminal may determine a distortion between a three-dimensional map or video feed and a two-dimensional plan view map. Moreover, determining a distortion may relate to transforming coordinates between first person views, third person views, plan view map views, hybrid map views, and/or between any two different coordinate systems or perspectives within the same coordinate system.

Referring again to FIG. 13, in some implementations, when the user places a tag 662 or hyper-tag 1310 on the plan view map 810 displayed as the map 622 in the map window, the telepresence software application 601 determines a user selected location on an electronic display displaying the map 622 and overlays an annotation associated with the tag 662, 1310 on the map 622. The telepresence software application 601 may also determine a distortion between the plan view map 810 and the remote view 610 (i.e., first-person video captured by the robot camera 320) and apply the distortion to coordinates of the tag 662, 1310 on the plan view map 810 to determine corresponding video coordinates of the remove view 610. A tag annotation associate with the tag 662, 1310 and stored by the map data source 1620 can be displayed by the telepresence software application 601 on the remote view 610 using the determined video coordinates.

Referring to FIG. 17, in some implementations, the user interface 605 provides an augmented overlay 1710, for example, in the remote video feed window 610 and/or the map window 620, that allows the user to visualize a position of the robot head 160 with respect to the robot base 120. The augmented overlay 1710 may allow the user to appreciate a current field of view 322, 442, 452, denoted by an arc 1720 in the example shown, of the robot sensor system 400 relative to a full 360 degrees field of view. This allows the user to make selections for rotation (e.g., of the head 160 and/or base 120) which are outside the current field of view 322, 442, 452.

The user may click within the zone defined by first and second rings 1722 and 1724 in order to rotate a virtual head 1728 to that point. As the user rotates the virtual had 1728, the robot head 160 may move in real time with the telepresence software application 601 updating the live video feed from the robot camera 320 displayed in the remote view 612 of the remote video feed window 610 in real-time as well. In the example shown, the augmented overlay 1710 has a virtual base 1726 corresponding to the robot base 120 and a virtual head 1728 corresponding to the robot head 160 arranged at an angle/orientation with respect to the virtual base 1726 that corresponds to a current pose of the robot 100. In some examples, one of the virtual base 1726 and the virtual head 1728 is shown static while the other is free to move relative to the static one.

If the user clicks within the zone defined by the first and second rings 1722 and 1724 to rotate the head 1728 outside of the current field of view 1720, the robot 100 may rotate the head 160 and/or the base 120 in order to accomplish the user's command. In some examples, after rotating the head 160 according to the user command, the base 120 may rotate and the head 160 may then move to a center position. Such changes in position may be problematic if the user then attempts to reposition the robot 100 based on the previous rotation. To mitigate this, certain implementations may employ a system to reduce the requirement of base rotations in order to accommodate head rotations. For example, a counter may be initiated when the virtual head 1728 is turned to an angle. If the robot head 160 remains at that angle for a specified interval, the system may slowly rotate the base 120 in order to center the head 160 with respect to the base 120 while simultaneously rotating the head 160 in the opposite direction at the same speed. This keeps the current subject in view, while also ensuring that the head 160 and the base 120 are now in alignment and the forward frame of reference is dictated by where the user is looking. Further, if the user wishes to continue looking farther in that direction, the full panning range of motion of the head 160 is available.

Figure 18:
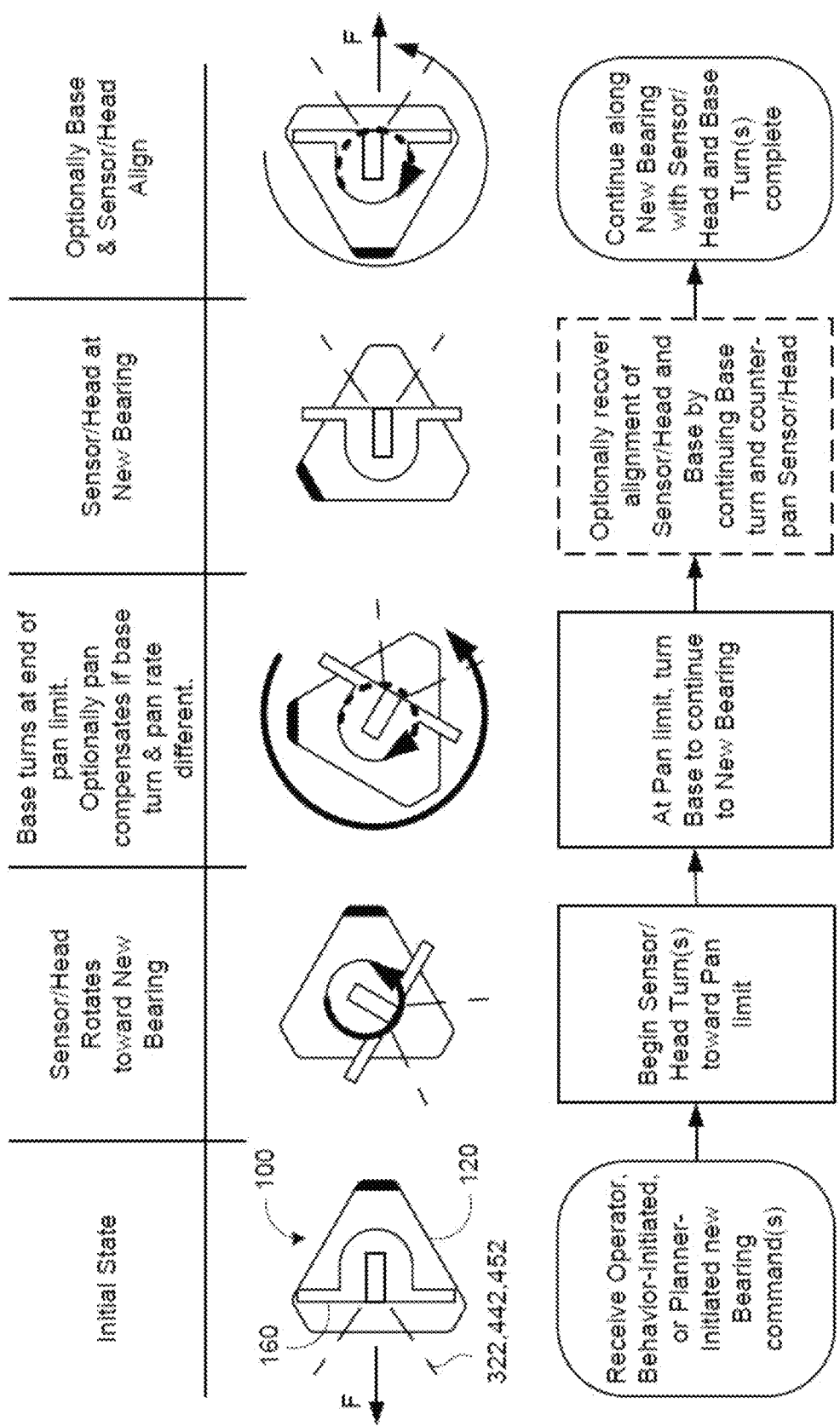
FIG. 18 is a schematic view of an example sequence of robot actions.

FIG. 18 illustrates an example sequence of robot events for responding to a user command, for example, in the telepresence software application 601. In an initial state, the robot 100 may receive a drive command to move from one location to another. The command may be operator-initiated, behavior-initiated (e.g., of a behavior executing on a control system of the controller), or planner-initiated (e.g., a pre-planned task or routine). In this example, the command includes a new heading for moving in an opposite direction to a new destination. In response to the command, the robot 100 may turn its head 160 (left or right) toward a panning limit. After reaching the panning limit, the robot 100 may rotate the base 120 (e.g., holonomically in place), to allow movement of the head 160 in order for the head to turn toward the new heading. The term "panning limit" may refer to a point when the upper portion of the robot cannot physically rotate anymore with respect to the lower portion of the robot, a point where the upper portion is misaligned with respect to the lower portion a predefined number of rotational degrees, and/or the term panning limit" may be a function of the number of degrees the upper portion is misaligned with respect to the lower portion and the length of time the upper portion has been misaligned with respect to the lower portion.

In some examples, the robot 100 continues to rotate the base 120, so that the forward drive direction F coincides with the new heading, thus providing the head 160 relatively equal left/right panning ability. As the robot 100 rotates the base, it may simultaneously rotate the head 160 so as to face the heading and optionally so that a field of view 322, 452 of a sensor 320, 450, 450b on the head 160 can point along the new heading. In some implementations, the robot 100 turns the base 120 and the head 160 together, so as to allow the head 160 to face the new heading relatively quicker. If the base 120 over-rotates, the head 160 can counter-pan to recover alignment.

Figure 19:
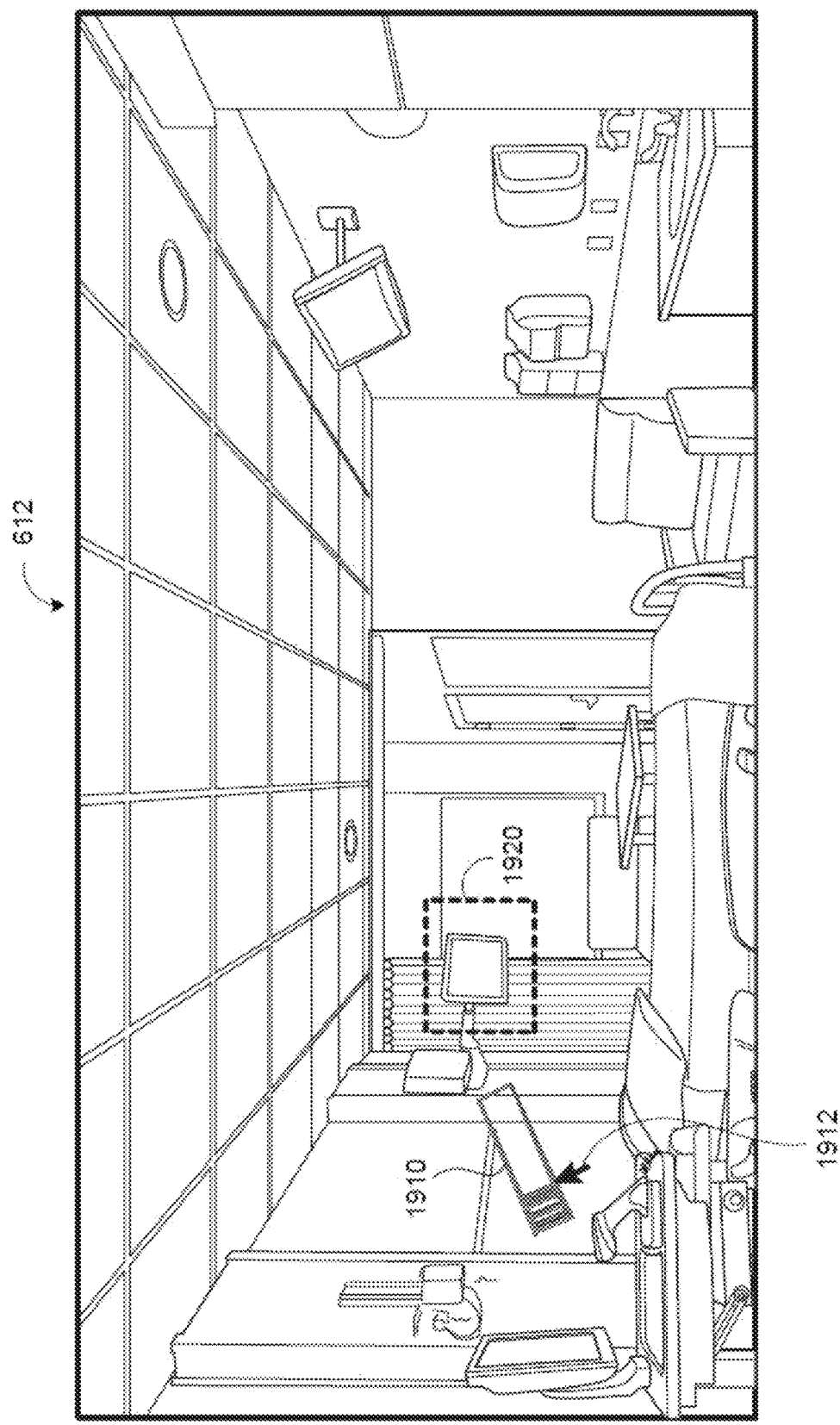
FIG. 19 is a schematic view of an example user interface having a screen indicator overlaid on a remote video feed received from a telepresence robot.

FIG. 19 illustrates an example remote view 612 where the telepresence software application 601 overlays a screen indicator 1910 on the remote video feed received from the robot 100. The screen indicator 1910 may be displayed near a mouse cursor 1912 and may represent a current head range of motion. As the user moves the mouse cursor 1912 toward the left or right side of the remote video view 612 (with the probable intention of clicking to move the head to point there), the on screen indicator 1910 may be displayed above the cursor 1912 to indicate how much head motion remains in that direction (e.g., how much remaining range of motion of the head 160 is available).

A highlight box 1920 may highlight an area of interest within the remote video view 612. The user may create the highlight box 1920 around an area of interest on a portion of the remote video view 612, for example, by dragging and dropping a box onto the screen and/or by clicking and dragging open a box around the area of interest. In response, the telepresence software application 601 may cause the robot head 160 to move to center on the highlight box 1920. Moreover, the camera 320 may zoom in to match the dimensions of the highlight box 1920.

Figure 20A:
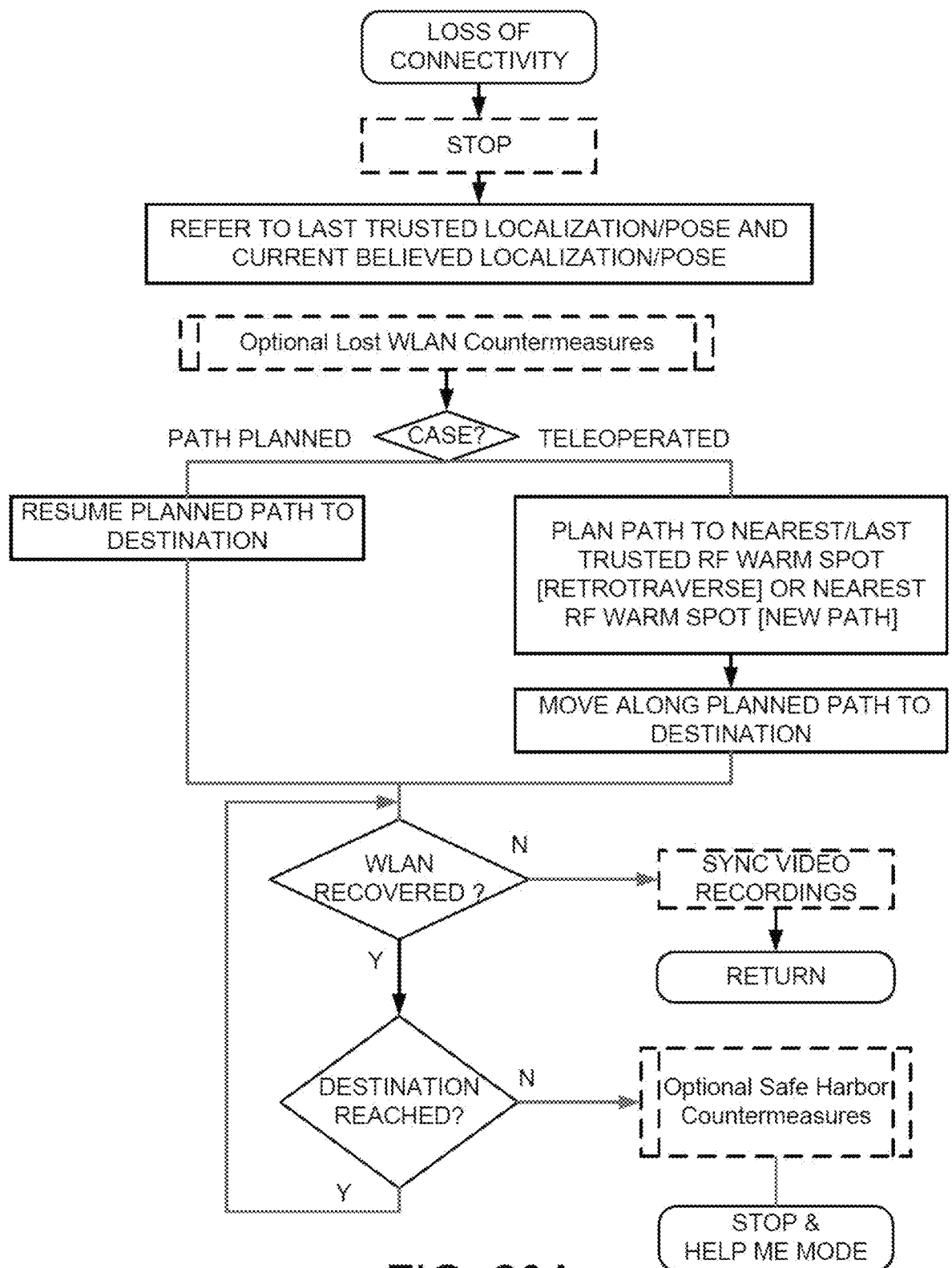
FIGS. 20A-20C provide an example arrangement of operations for recovering from a loss of robot communications.
Figure 20B:
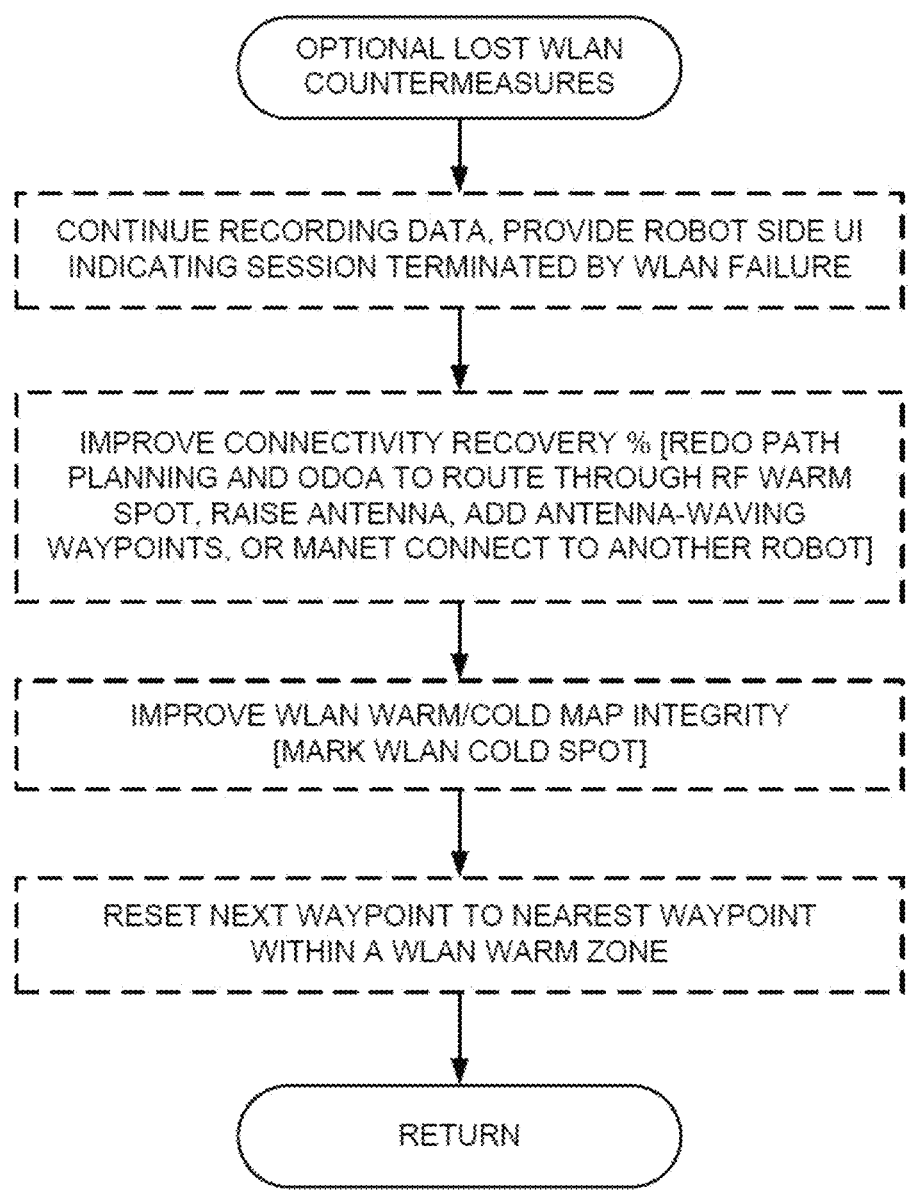
Figure 20C:
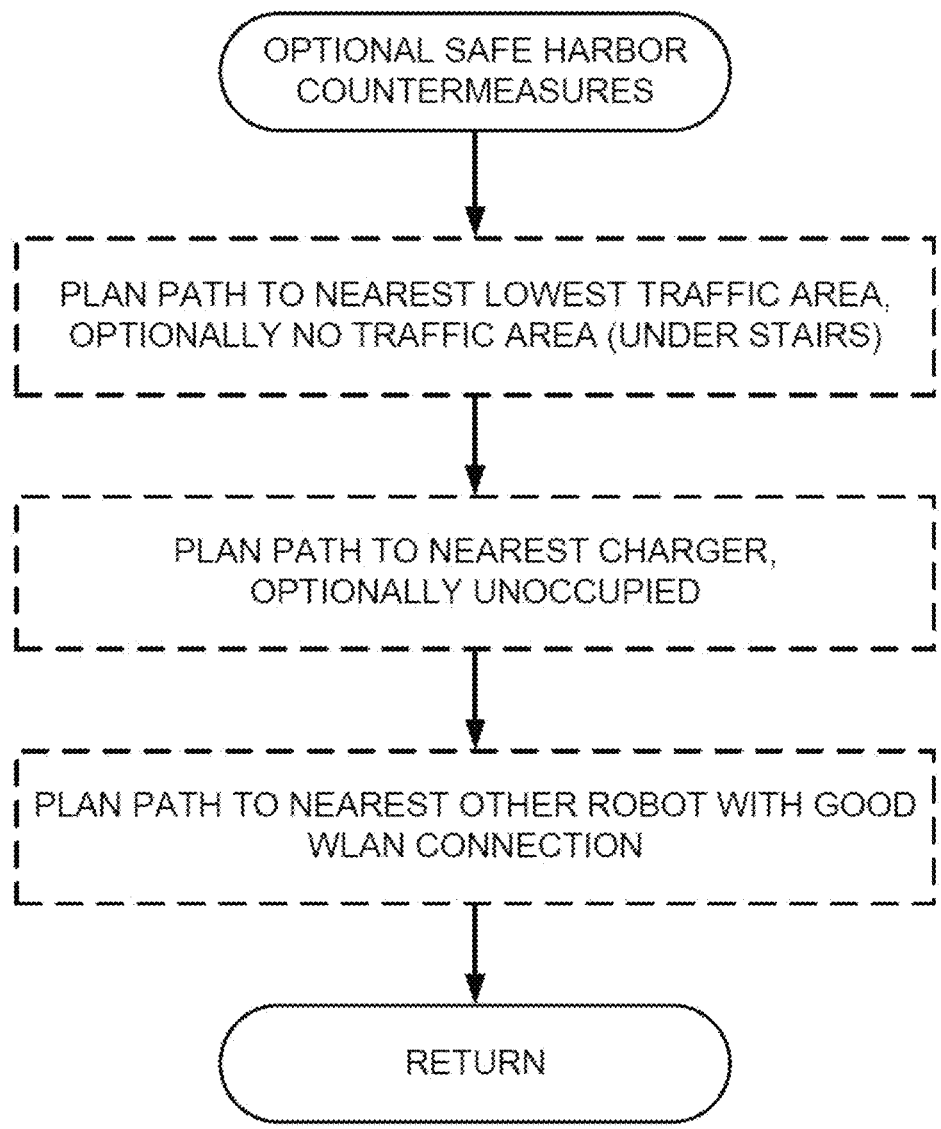

Referring to FIGS. 20A-20B, in some implementations, if the robot 100 unexpectedly loses communication connectivity (e.g., a loss of the wireless signal), the robot 100 may stop or continue driving to its destination. As a telepresence robot moves throughout an environment, communication may be disrupted, for example, as the robot 100 transitions between various wireless access points and/or encounters disruptions in the data transmission as a result of poor signal strength. By continuing to navigate autonomously, communication may be restored by the time the robot arrives at a desired destination.

When the robot 100 experiences a loss of communication connectivity, the robot 100 may refer to a last trusted localization/pose (e.g., stored locally by the controller 500) and/or a current determined localization/pose (e.g., based on the robot sensor system 400) to continue navigating to the destination. If the robot path is a planned path, the robot 100 may resume the planned path to the destination. On the other hand, if the user was teleoperating the robot 100 to the destination, the robot 100 may follow a planned path to a nearest/last trusted location having communication connectivity (e.g., radiofrequency and/or wireless). Alternatively, the robot 100 may drive along a shortest path (i.e., a new path) to a nearest/last trusted location having communication connectivity.

After reaching the nearest/last trusted location, the robot 100 may determine if communication connectivity has been reestablished and if so, whether the destination has been reached. If communication connectivity was not reestablished, the robot 100 may synchronize its video recordings (and any other sensor data of the sensor system 400) to move to a next trusted location stored by the controller 500. Moreover, if the destination has not been reached, but communication connectivity was reestablished, the controller 500 may execute safe harbor countermeasures, which may entail continuing recording sensor data and displaying a new robot-side user interface (e.g., on the web pad 310) indicating that the session was terminated due to loss of communication connectivity. The robot 100 may improve its connectivity recovery percentage by reassessing and/or executing path planning to move to the last trusted location (using ODOA). The robot 100 may also move its antennas 490a, 490b (FIGS. 2 and 4C) to possibly gain better communication reception. The robot 100 may use a mobile ad-hoc network (MANET), which is a self-configuring infrastructureless network of mobile devices connected by wireless links.

In some examples, the robot 100 may improve the integrity/accuracy of the robot map 820 by marking the location of lost communications and any location of reestablished communications. The robot 100 may use waypoint navigation to move to an area having known connectivity (e.g., a WLAN warm zone or high signal zone). Waypoints are sets of coordinates that identify a point in physical space. The robot 100 may use waypoints established on the robot map 820 to maneuver to the destination.

Additional safe harbor countermeasures may include planning a path to a nearest lowest traffic area or moving to a nearest charging/docking station based on the robot map 820. In some examples, the robot 100 may move toward another nearest robot 100, which may use multiple antennas 490*a*, 490*b* for multiple-input and multiple-output (MIMO) to act as a Wi-Fi bridge 602.

Various implementations of the systems and techniques described here can be realized in digital electronic circuitry, integrated circuitry, specially designed application specific integrated circuits (ASICs), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer-readable medium for execution by, or to control the operation of, data processing apparatus. The computer-readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a standalone program or as a module, a component, a subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., a field programmable gate array (FPGA) or an ASIC.

Processors suitable for the execution of a computer program include, by way of example, both general and special purpose microprocessors, and any one or more processors of any kind of a digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic disks, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Implementations of the subject matter described in this specification can be implemented in a computing system that includes a back end component, e.g., as a data server; that includes a middleware component, e.g., an application server; or that includes a front end component, e.g., a client computer having a graphical user interface or a web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of a client and server arises by virtue of computer programs running on the respective computers and having a client-server relationship to each other.

While this specification contains many specifics, these should not be construed as limitations on the scope of the invention or of what may be claimed, but rather as descriptions of features specific to particular implementations of the invention. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A telepresence robot, comprising:
    a plurality of drive wheels;
    at least one drive motor to rotate one or more of the plurality of drive wheels;
    a processor to control the at least one drive motor to move the telepresence robot along a navigation path including a location in a robot environment; and
    a memory to store a map of the robot environment including a schedule of at least one time-dependent navigation tag, the at least one time-dependent navigation tag comprising:
        an indication of the location within the robot environment;
        an indication of a triggering time of day; and
        at least one instruction to be performed when the telepresence robot is at the location at the triggering time of day;
    wherein the processor accesses the map and the schedule of the at least one time-dependent navigation tag during movement of the telepresence robot along at least a portion of the navigation path and, when the telepresence robot is at the location and a current time of day coinciding with the triggering time of day, the processor performs the at least one instruction specified in the at least one time-dependent navigation tag according to the schedule, wherein the at least one instruction causes the processor to change a movement speed of the telepresence robot while the telepresence robot is at the location at the triggering time of day.

2. The telepresence robot of claim 1, wherein the at least one instruction is configured to cause the processor to decrease the movement speed of the telepresence robot along the at least a portion of the navigation path.

3. The telepresence robot of claim 1, wherein the at least one instruction is configured to cause the processor to increase the movement speed of the telepresence robot along the at least a portion of the navigation path.

4. The telepresence robot of claim 1, wherein the at least one instruction is configured to cause the processor to move the telepresence robot at a particular movement speed along the at least a portion of the navigation path.

5. The telepresence robot of claim 1, further comprising a plurality of sensors monitoring at least one of time-dependent obstacles, time-dependent environmental conditions and time-dependent occupancy conditions, wherein the plurality of sensors are mounted on the telepresence robot and in remote communication with the telepresence robot.

6. The telepresence robot of claim 5, wherein the telepresence robot is configured to create the at least one time-dependent navigation tag based on information from the plurality of sensors and time of day information.

7. The telepresence robot of claim 1, wherein the map is stored remotely, such that the processor is configured to access the map via a communication system.

8. The telepresence robot of claim 1, wherein the map is stored within the telepresence robot.

9. The telepresence robot of claim 8, wherein the map stored within the telepresence robot is synced with a remotely stored map.

10. A method comprising:
    obtaining a navigation path for moving a telepresence robot about a robot environment on a schedule;
    accessing a map of the robot environment including a location of at least one time-dependent navigation tag, the at least one time-dependent navigation tag including:
        an indication of a location within the robot environment;
        an indication of a triggering time of day; and
        at least one instruction to be performed when the telepresence robot is at the location at the triggering time of day, the at least one instruction configured to cause a processor to control a drive motor to change a movement speed of the telepresence robot while the telepresence robot is at the location at the triggering time of day; and
    while the telepresence robot moves along at least a portion of the navigation path and reaches the location according to the schedule:
        determining a current time of day; and
        when the current time of day coinciding with the triggering time of day, changing the movement speed of the telepresence robot according to the at least one instruction while the telepresence robot is at the location.

11. The method of claim 10, wherein the at least one instruction is configured to cause the processor to decrease the movement speed of the telepresence robot along the at least a portion of the navigation path.

12. The method of claim 10, wherein the at least one instruction is configured to cause the processor to increase the movement speed of the telepresence robot along the at least a portion of the navigation path.

13. The method of claim 10, wherein the at least one instruction is configured to cause the processor to move the telepresence robot at a particular movement speed along the at least a portion of the navigation path.

14. The method of claim 10, wherein the telepresence robot includes a plurality of sensors for monitoring at least one of time-dependent obstacles, time-dependent environmental conditions and time-dependent occupancy conditions, the method further comprising:
creating at least one time-dependent navigation tag based on information from the plurality of sensors and time of day information.

15. The method of claim 10, wherein the map is stored remotely, and wherein accessing comprises accessing the map via a communication system.

16. The method of claim 10, wherein the map is stored within the telepresence robot.

17. The method of claim 16, further comprising:
synching the map stored within the telepresence robot with a remotely stored map.

18. A non-transitory computer-readable medium comprising program code that, when executed by a processor, causes the processor to perform a method comprising:
obtaining a navigation path for moving a telepresence robot about a robot environment on a schedule;
accessing a map of the robot environment including a location of at least one time-dependent navigation tag, the at least one time-dependent navigation tag including:
an indication of a location within the robot environment;
an indication of a triggering time of day; and
at least one instruction to be performed when the telepresence robot is at the location at the triggering time of day, the at least one instruction configured to cause the processor to control a drive motor to change a movement speed of the telepresence robot while the telepresence robot is at the location at the triggering time of day; and
while the telepresence robot moves along the at least a portion of the navigation path and reaches the location according to the schedule:
determining a current time of day; and
when the current time of day coinciding with the triggering time of day, changing the movement speed of the telepresence robot according to the at least one instruction while the telepresence robot is at the location.

* * * * *